US008084250B2

(12) United States Patent
Kwak et al.

(10) Patent No.: US 8,084,250 B2
(45) Date of Patent: *Dec. 27, 2011

(54) DEFENSIN-ANTIGEN FUSION PROTEINS

(75) Inventors: Larry W. Kwak, Frederick, MD (US); Bira Arya, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/019,160

(22) Filed: Feb. 1, 2011

(65) Prior Publication Data

US 2011/0135715 A1    Jun. 9, 2011

Related U.S. Application Data

(60) Continuation of application No. 12/786,334, filed on May 24, 2010, now Pat. No. 7,915,040, which is a division of application No. 10/380,926, filed as application No. PCT/US01/29074 on Sep. 17, 2001, now Pat. No. 7,754,676.

(60) Provisional application No. 60/233,074, filed on Sep. 15, 2000.

(51) Int. Cl.
  *C12N 15/00* (2006.01)
  *C07H 17/00* (2006.01)
  *C07K 14/00* (2006.01)
(52) U.S. Cl. ......... 435/320.1; 536/23.1; 514/1; 530/350
(58) Field of Classification Search ............... 435/320.1; 536/23.1; 514/1; 530/350
  See application file for complete search history.

(56) References Cited

U.S. PATENT DOCUMENTS

| 3,710,795 | A | 1/1973 | Higuchi et al. |
| 4,704,362 | A | 11/1987 | Itakura et al. |
| 5,989,552 | A | 11/1999 | McKenzie et al. |
| 6,001,649 | A | 12/1999 | Caput et al. |
| 6,562,347 | B1 | 5/2003 | Kwak et al. |
| 2003/0138452 | A1 | 7/2003 | Kwak et al. |
| 2004/0110165 | A1 | 6/2004 | Kwak et al. |

FOREIGN PATENT DOCUMENTS

| EP | 0706799 A2 | 4/1996 |
| WO | WO 88/09344 | 12/1988 |
| WO | WO 97/35008 | 9/1997 |
| WO | WO 98/01564 | 1/1998 |
| WO | WO 98/07833 | 2/1998 |
| WO | WO 99/46392 | 9/1999 |
| WO | WO 00/78334 A | 12/2000 |

OTHER PUBLICATIONS

International Search Report from prior PCT Application No. PCT/US2001/029074, 5 pp, (mailed Jul. 29, 2002).
Lofthouse et al., "Induction of T1 (cytotoxic lymphocyte) and/or T2 (antibody) responses to a mucin-1 tumor antigen," *Vaccine* 15(14): 1586-1593 (1997).
Biragyn et al. "*E. coli* Expressed Lymphoma IG Idiotype Antigen Fusion Proteins and Chimeric, HBcAG Particles Bearing Tumor Epitopes" *Cancer Biotherapy* 10(1):85 (Mar. 3, 1995).
Boon, "Toward a genetic analysis of tumor rejection antigens," *Advances in Cancer Res.* 58:177-210, 1992.
Cocchi et al. "The V3 Domain of the HIV-1 gp120 Envelope Glycoprotein Is Critical for Chemokine-Mediated Blockade of Infection" *Nature Medicine* 2(11):1244-7 (Nov. 1996).
Hellstrom et al, "Can co-stimulated tumor immunity be therapeutically efficacious?" *Immunol. Rev.* 145:123-145(1995).
Kwak et al. "Idiotypes as Vaccines for the Treatment of B-Cell Malignancies" *Immunotechnology* 2(4):268 (Nov. 1, 1996).
U.S. Appl. No. 09/646,028, Kwak et al., filed Mar. 12, 1999, Preliminary Amendment, Mar. 12, 2000.
U.S. Appl. No. 09/646,028, Kwak et al., filed Mar. 12, 1999, Restriction Requirement, Jan. 10, 2001.
U.S. Appl. No. 09/646,028, Kwak et al., filed Mar. 12, 1999, Restriction Requirement, Feb. 2, 2001.
U.S. Appl. No. 09/646,028, Kwak et al., filed Mar. 12, 1999, Response to Restriction Requirement, Mar. 2, 2001.
U.S. Appl. No. 09/646,028, Kwak et al., filed Mar. 12, 1999, Non-final Office Action, May 11, 2001.
U.S. Appl. No. 09/646,028, Kwak et al., filed Mar. 12, 1999, Response to Non-Final Office Action, Sep. 12, 2001.
U.S. Appl. No. 09/646,028, Kwak et al., filed Mar. 12, 1999, Final Office Action, Nov. 30, 2001.
U.S. Appl. No. 09/646,028, Kwak et al., filed Mar. 12, 1999, Response to Final Office Action, Apr. 1, 2002.
U.S. Appl. No. 09/646,028, Kwak et al., filed Mar. 12, 1999, Advisory Action, Apr. 25, 2002.
U.S. Appl. No. 09/646,028, Kwak et al., filed Mar. 12, 1999, Response to Advisory Action and Request for Continued Examination, Apr. 30, 2002.
U.S. Appl. No. 09/646,028, Kwak et al., filed Mar. 12, 1999, Final Office Action Jul. 3, 2002.
U.S. Appl. No. 09/646,028, Kwak et al., filed Mar. 12, 1999, Response to Final Office Action, Oct. 30, 2002.
U.S. Appl. No. 09/646,028, Kwak et al., filed Mar. 12, 1999, Advisory Action, Nov. 12, 2002.
U.S. Appl. No. 09/646,028, Kwak et al., filed Mar. 12, 1999, Response to Advisory Action, Dec. 3, 2002.
U.S. Appl. No. 09/646,028, Kwak et al., filed Mar. 12, 1999, Notice of Allowance, Dec. 19, 2002.
U.S. Appl. No. 10/335,394, Kwak et al., filed Dec. 31, 2002, Preliminary Amendment, Dec. 31, 2002.
U.S. Appl. No. 10/335,394, Kwak et al., filed Dec. 31, 2002, Restriction Requirement, Feb. 10, 2005.
U.S. Appl. No. 10/335,394, Kwak et al., filed Dec. 31, 2002, Response to Restriction Requirement, Apr. 11, 2005.

(Continued)

*Primary Examiner* — Karen Carlson
(74) *Attorney, Agent, or Firm* — Klarquist Sparkman, LLP

(57) ABSTRACT

The present invention relates to a vaccine for increasing the immunogenicity of a tumor antigen thus allowing treatment of cancer, as well as a vaccine that increases the immunogenicity of a viral antigen, thus allowing treatment of viral infection, including immunodeficiency virus (HIV) infection. In particular, the present invention provides a fusion protein comprising a defensin fused to either a tumor antigen or viral antigen which is administered as either a protein or nucleic acid vaccine to elicit an immune response effective in treating cancer or effective in treating or preventing viral infection.

30 Claims, 1 Drawing Sheet

OTHER PUBLICATIONS

U.S. Appl. No. 10/335,394, Kwak et al., filed Dec. 31, 2002, Non-final Office Action, Jun. 7, 2005.
U.S. Appl. No. 10/335,394, Kwak et al., filed Dec. 31, 2002, Response to Non-final Office Action, Dec. 7, 2005.
U.S. Appl. No. 10/335,394, Kwak et al., filed Dec. 31, 2002, Final Office Action, Mar. 2, 2006.
U.S. Appl. No. 10/335,394, Kwak et al., filed Dec. 31, 2002, Response to Final Office Action, Jun. 2, 2006.
U.S. Appl. No. 10/335,394, Kwak et al., filed Dec. 31, 2002, Advisory Action, Jun. 9, 2006.
U.S. Appl. No. 10/335,394, Kwak et al., filed Dec. 31, 2002, Communication RE; Appeal/Notice of Abandonement, Apr. 26, 2007.
U.S. Appl. No. 10/380,927, Kwak et al., filed Mar. 17, 2003, Preliminary Amendment, Mar. 17, 2003.
U.S. Appl. No. 10/380,927, Kwak et al., filed Mar. 17, 2003, Restriction Requirement, Jun. 15, 2004.
U.S. Appl. No. 10/380,927, Kwak et al., filed Mar. 17, 2003, Response to Restriction Requirement, Jul. 28, 2004.
U.S. Appl. No. 10/380,927, Kwak et al., filed Mar. 17, 2003, Non-Final Office Action, Oct. 19, 2004.
U.S. Appl. No. 10/380,927, Kwak et al., filed Mar. 17, 2003, Response to Non-Final Office Action, Feb. 22, 2005.
U.S. Appl. No. 10/380,927, Kwak et al., filed Mar. 17, 2003, Final Office Action, Dec. 14, 2005.
U.S. Appl. No. 10/380,927, Kwak et al., filed Mar. 17, 2003, Interview Summary, Dec. 22, 2005.
U.S. Appl. No. 10/380,927, Kwak et al., filed Mar. 17, 2003, Response to Final Office Action, May 15, 2006.
U.S. Appl. No. 10/380,927, Kwak et al., filed Mar. 17, 2003, Non-Final Office Action, Aug. 8, 2006.
U.S. Appl. No. 10/380,927, Kwak et al., filed Mar. 17, 2003, Response to Non-Final Office Action, Dec. 7, 2006.
U.S. Appl. No. 10/380,927, Kwak et al., filed Mar. 17, 2003, Final Office Action, Mar. 8, 2007.
U.S. Appl. No. 10/380,927, Kwak et al., filed Mar. 17, 2003, Response to Final Office Action and Request for Continued Examination, Sep. 10, 2007.
U.S. Appl. No. 10/380,927, Kwak et al., filed Mar. 17, 2003, Final Office Action, Nov. 28, 2007.
U.S. Appl. No. 10/380,927, Kwak et al., filed Mar. 17, 2003, Response to Final Office Action, Apr. 15, 2008.
U.S. Appl. No. 10/380,927, Kwak et al., filed Mar. 17, 2003, Advisory Action, Apr. 29, 2008.
U.S. Appl. No. 10/380,927, Kwak et al., filed Mar. 17, 2003, Request for Continued Examination, May 28, 2008.
U.S. Appl. No. 10/380,927, Kwak et al., filed Mar. 17, 2003, Non-Final Office Action, Aug. 19, 2008.
U.S. Appl. No. 10/380,927, Kwak et al., filed Mar. 17, 2003, Response to Non-Final Office Action, Nov. 19, 2008.
U.S. Appl. No. 10/380,927, Kwak et al., filed Mar. 17, 2003, Final Office Action, Feb. 13, 2009.
U.S. Appl. No. 10/380,927, Kwak et al., filed Mar. 17, 2003, Response to Final Office Action, Apr. 13, 2009.
U.S. Appl. No. 10/380,927, Kwak et al., filed Mar. 17, 2003, Interview Summary, Apr. 16, 2009.
U.S. Appl. No. 10/380,927, Kwak et al., filed Mar. 17, 2003, Advisory Action, May 13, 2009.
U.S. Appl. No. 10/380,927, Kwak et al., filed Mar. 17, 2003, Response to Final Office Action and Request for Continued Examination, Jun. 15, 2009.
PCT/US99/05345, filed Mar. 12, 1999, Kwak et al., Application with International Search Report, Jul. 15, 1999.
PCT/US01/29075, filed Sep. 17, 2001, Kwak et al., International Search Report, Sep. 25, 2002.
PCT/US01/29075, filed Sep. 17, 2001, Kwak et al., International Preliminary Examination Report, Sep. 15, 2004.
Biragyn et al., "B-Cell Malignancies as a Model for Cancer Vaccines: From Prototype Protein to Next Generation Genetic Chemokine Fusions," *Immunological Reviews, Munksgaard*, vol. 170, Aug. 1999, pp. 115-126.
Biragyn et al., "Genetic Fusion of Chemokines to a Self Tumor Antigen Induces Protective, T-Cell Dependent Antitumor Immunity-" *Nature Biotechnology*, Nature Publishing, U.S., vol. 17, No. 3, Mar. 1, 1999, pp. 253-258.
Agrawal et al. Cell-cycle kinetics and VSV-G pseudotyped retrovirus-mediated gene transfer in blood-derived $CD34^+$ cells. *Exp. Hematol.* 24:738-747 (1996).
Alvarez et al. A phase I study of recombinant adenovirus vector-mediated delivery of an anti-erbB-2 single chain (sFv) antibody gene for previously treated ovarian and extraovarian cancer patients. *Hum. Gene Ther.* 8:229-242 (1997).
Arnon, ed. *Synthetic Vaccines* I:83-92 CRC Press, Inc., Boca Raton, FL (1987).
Baggiolini et al. Interleukin-8 and related chemotactic cytokines-CXC and CC chemokines. *Adv. Immunol.* 55:97-179 (1994).
Barbas et al. Semisynthetic combinatorial antibody libraries: a chemical solution to the diversity problem. *PNAS* 89:4457-4461 (1992).
Belyakov et al. Mucosal immunization with HIV-1 peptide vaccine induces mucosal and systemic cytotoxic T lymphocytes and protective immunity in mice against intrarectal recombinant HIV-vaccinia challenge. *Proc Natl Acad Sci USA*. 95:1709-1714 (1998).
Belyakov et al. Induction of a mucosal cytotoxic T-lymphocyte response by intrarectal immunization with a replication-deficient recombinant vaccinia virus expressing human immunodeficiency virus 89.6 envelope protein. *J Virol.* 72(10):8264-8272 (1998).
Ben-Baruch et al. The differential ability of IL-8 and neutrophil-activating peptide-2 to induce attenuation of chemotaxis is mediated by their divergent capabilities to phosphorylate CXCR2 (IL-8 receptor B). *J Immunol.* 158:5927-5933 (1997).
Bergman et al. Characterization of a carcinogen-induced murine B lymphocyte cell line of C3H/eB origin. *Eur. J. Immunol.* 7:413-417 (1977).
Biragyn et al. Mediators of innate immunity that target immature, but not mature, dendritic cells induce antitumor immunity when genetically fused with nonimmunogenic tumor antigens. *J Immun* 167(11):6644-6653 (2001).
Blasi et al. Selective immortalization of murine macrophages from fresh bone marrow by a *raf/myc* recombinant murine retrovirus. *Nature* 318:667-670 (1985).
Bonecchi et al. Differential expression of chemokine receptors and chemotactic responsiveness of type 1 T helper cells (Th1s) and Th2s. *J. Exp. Med.* 187(1):129-134 (1998).
Brake et al. α-factor-directed synthesis and secretion of mature foreign proteins in *Saccharomyces cerevisiae*. *PNAS* 81:4642-4646 (1984).
Bridges. Participation of the humoral immune system in the myeloma-specific transplantation resistance. *J. Immunol.* 121(2):479-483 (1978).
Buchner et al. A method for increasing the yield of properly folded recombinant fusion proteins: single-chain immunotoxins from renaturation of bacterial inclusion bodies. *Analytical Biochem.* 205:263-270 (1992).
Butcher. Leukocyte-endothelial cell recognition: three (or more) steps to specificity and diversity. *Cell* 67:1033-1036 (1991).
Bystryn. Immunogenicity and clinical activity of a polyvalent melanoma antigen vaccine prepared from shed antigens. *Annals New York Academy of Sciences* 690:190-203 (1993).
Campbell et al. Development of a new therapeutic approach to B cell malignancy. The induction of immunity by the host against cell surface receptor on the tumor, *Int. Rev. Immunol.* 4:251-270 (1989).
Campbell et al. Idiotype vaccination against murine B cell lymphoma. Humoral and cellular requirements for the full expression of antitumor immunity. *J. Immunol.* 145(3):1029-1036 (1998).
Campbell et al. Idiotype vaccination against murine B cell lymphoma. Humoral and cellular responses elicited by tumor-derived immunoglobulin M and its molecular subunits. *J. Immunol.* 139(8):2825-2833 (1987).
Clark-Lewis et al. Structure-activity relationships of Interleukin-8 determined using chemically synthesized analogs: critical role of $NH_2$-terminal residues and evidence for uncoupling neutrophil chemotaxis, exocytosis, and receptor binding activities. *J. Biol. Chem.* 266(34):23128-23134 (1991).
Crystal. Clinical protocol: Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985-1001 (1997).

Daley et al. Idiotype-specific transplantation resistance to MOPC-315: abrogation by post-immunization thymectomy. *J. Immunol.* 120(5):1620-1624 (1978).

Damon et al. Broad spectrum chemokine antagonistic activity of a human poxvirus chemokine homolog. *Proc Natl Acad Sci USA.* 95:6403-6407 (1998).

Davis et al. DNA-based immunization against hepatitis B surface antigen (HBsAg) in normal and HBsAg-transgenic mice. *Vaccine* 15(8):849-852 (1997).

Dieu et al. Selective recruitment of immature and mature dendritic cells by distinct chemokines expressed in different anatomic sites. *J Exp Med.* 188(2):373-386 (1998).

Dilloo et al. Combined chemokine and cytokine gene transfer enhances antitumor immunity. *Nature Medicine* 2(10):1090-1095 (1996).

Dyke et al. Idiotypic vaccination against B-cell lymphoma leads to dormant tumour. *Cell Immunol.* 132:70-83 (1991).

Emini et al. Prevention of HIV-1 infection in chimpanzees by gp120 V3 domain-specific monoclonal antibody. *Nature* 355:728-730 (1992).

Endres et al. The Kaposi's sarcoma-related herpesvirus (KSHV)-encoded chemokine vMIP-I is a specific agonist for the CC chemokine receptor (CCR)8. *J Exp Med.* 189(12):1993-1998 (1999).

Fairbrother et al. Chapter 3: Three-dimensional structures of the chemokine family. *Chemoattractant ligands and their receptors.* R. Horuk, Ed. (CRC, Boca Raton, NY, London, Tokyo) p. 55 (1996).

Falk et al. A 48-well micro chemotaxis assembly for rapid and accurate measurement of leukocyte migration. *J. Immunol. Methods.* 33:239-247 (1980).

Feltquate et al. Different T helper cell types and antibody isotypes generated by saline and gene gun DNA immunization. *J. Immunol.* 158:2278-2284 (1997).

Fields et al. Comparative analysis of murine dendritic cells derived from spleen and bone marrow. *J Immunother.* 21(5):323-339 (1998).

Finn et al. MUC-1 epithelial tumor mucin-based immunity and cancer vaccines. *Immunological Reviews* 145:61-89 (1995).

Freedman et al. Tumor immunity induced by preimmunization with BALB/c mouse myeloma protein. *J. Natl. Cancer Inst.* 56(4):735-740 (1976).

Garcia-Zepeda et al. Human monocyte chemoattractant protein (MCP)-4 is a novel cc chemokine with activities on monocytes, eosinophils and basophils induced in allergic and nonallergic inflammation that signals through the CC chemokine receptors (CCR)—2 and—3. *J. Immunol.* 157:5613-5626 (1996).

George et al. Anti-idiotypic mechanisms involved in the suppression of a mouse B cell lymphoma, $BCL_1$. *J. Immunol.* 138(2):628-634 (1987).

Gong et al. RANTES and MCP-3 antagonists bind multiple chemokine receptors. *J. Biol. Chem.* 271(18):10521-10527(1996).

Goodman et al. Recombinant adeno-associated virus-mediated gene transfer into hematopoietic progenitor cells. *Blood* 84(5):1492-1500 (1994).

Gribben et al. Immunologic purging of marrow assessed by PCR before autologous bone marrow transplantation for B-cell lymphoma. *N. Engl. J. Med.* 325(22):1525-1533 (1991).

Haelens et al. Leukocyte migration and activation by murine chemokines, *Immunobiology* 195:499-521 (1996).

Hakim et al. A nine-amino acid peptide from IL-1β augments antitumor immune responses induced by protein and DNA vaccines. *J. Immunol.* 157:5503-5511 (1996).

Hersey. Evaluaution of vaccinia viral lysates as therapeutic vaccines in the treatment of melanoma. *Annals New York Academy of Sciences* 167-177 (1993).

Ho et al. Quantitation of human immunodeficiency virus type 1 in the blood of infected persons *N. Eng. J. Med.* 321(24):1621-1625 (1988).

Huston et al. Protein engineering of antibody binding sites: recovery of specific activity in an anti-digoxin single-chain Fv analogue produced in *Escherichia coli. Proc. Natl. Acad. Sci. USA* 85:5879-5883 (1988).

Jellis et al. Defining critical residues in the epitope for a HIV-neutralizing monoclonal antibody using phage display and peptide array technologies. *Gene* 137:63-68 (1993).

Jørgensen et al. Immunization with the light chain and the $V_L$ domain of the isologous myeloma protein 315 inhibits growth of mouse plasmacytoma MOPC315. *Scand. J. Immunol.* 11:29-35 (1980).

Kageyama et al. An improved method for the detection of HIV antigen in the blood of carriers. *J. Virol. Meth.* 22:125-131 (1988).

Kaminski et al. Idiotype vaccination against murine B cell lymphoma, inhibition of tumor immunity by free idiotype protein. *J. Immunol.* 138(4):1289-1296 (1987).

Kim et al. Establishment and characterization of BALB/c lymphoma lines with B cell properties. *J. Immunol.* 122(2):549-554 (1979).

Kwak et al. Vaccination with syngeneic, lymphoma-derived immunoglobulin idiotype combined with granulocyte/macrophage colony-stimulating factor primes mice for a protective T-cell response. *Proc. Natl. Acad. Sci. USA* 93:10972-10977 (1996).

Kwak et al. Combined syngeneic bone marrow transplantation and immunotherapy of a murine B-cell lymphoma: active immunization with tumor-derived idiotypic immunoglobulin. *Blood* 76(11):2411-2417 (1990).

Kwak et al. Induction of immune responses in patients with B cell lymphoma against the surface-immunoglobulin idiotype expressed by their tumors. *N. Engl. J. Med.* 327(17):1209-1215 (1992).

Kwak et al, Transfer of myeloma idiotype-specific immunity from an actively immunized marrow donor. *Lancet* 345:1016-1020 (1995).

Kwak et al. Transfer of specific immunity to B-cell lymphoma with syngeneic bone marrow in mice: a strategy for using autologous marrow as an anti-tumor therapy. *Blood* 78(10):2768-2772 (1991).

Loetscher et al. Activation of NK cells by cc chemokines: chemotaxis, $Ca^{2+}$ mobilization and enzyme release. *J. Immunol.* 156:322-327 (1996).

Loetscher et al, Chemokine receptor specific for IP10 and Mig: structure, function and expression in activated T-lymphocytes. *J. Exp. Med.* 184:963-969 (1995).

Longo et al. What is so good about the "good prognosis" lymphoma? In Williams CG, Whithouse JMA (eds): *Recent Advances in Clinical Oncol* Edinburgh, Churchill-Livingstone, pp. 223-231 (1982).

Luster et al. IP-10, a—C-X-C- chemokine, elicits a potent thymus-dependent antitumor response in vivo. *J. Exp. Med.* 178:1057-1065 (1993).

Luster. Chemokines-chemotactic cytokines that mediate inflammation. *N. Eng. J. Med.* 338(7):436-445 (1998).

Lüttichau et al. A highly selective CC chemokine receptor (CCR)8 antagonist encoded by the poxvirus molluscum contagiosum. *J Exp Med.* 191(1):171-179 (2000).

Miller et al. Redesign of retrovirus packaging cell lines to avoid recombination leading to helper virus production. *Mol. Cell Biol.* 6(8):2895-2902 (1986).

Miller et al. Treatment of B cell lymphoma with monoclonal anti-idiotype antibody. *N. Engl. J. Med.* 306(9)517-522 (1982).

Mitani et al. Transduction of human bone marrow by adenoviral vector. *Human Gene Therapy* 5:941-948 (1994).

Mitchell et al. Active specific immunotherapy of melanoma with allogeneic cell lysates. *Annals New York Academy of Sciences* 153-166 (1993).

Morton et al. Polyvalent melanoma vaccine improves survival of patients with metastatic melanoma. *Annals New York Academy of Sciences* 120-134 (1993).

Mulder et al. Rapid and simple PCR assay for quantitation of human immunodeficiency virus type 1 RNA in plasma: application to acute retroviral infection. *J. Clin. Microbiol.* 32(2):292-300 (1994).

Naldini et al. In vivo gene delivery and stable transduction of nondividing cells by a lentiviral vector. *Science* 272:263-267 (1996).

Nicholas et at. Kaposi's sarcoma-associated human herpesvirus-8 encodes homologues of macrophage inflammatory protein-1 and interleukin-6. *Nat Med* 3(3):287-292 (1997).

Old, Cancer immunology: the search for specificity. GHA Clowes Memorial Lecture. *Cancer Res.* 41:361-375 (1981).

Orentas et al. Induction of CD4+ human cytolytic T cells specific for HIV-infected cells by a gp160 subunit vaccine. *Science* 248:1234-1236 (1990).

Pastan et al. A retrovirus carrying an *MDR1* cDNA confers multidrug resistance and polarized expression of P-glycoprotein in MDCK cells, *Proc. Nat. Acad. Sci.* 85:4486-4490 (1988).

Pelchen-Matthews et al. Chemokine receptor trafficking and viral replication. *Immunol. Rev.* 168:33-49 (1999).

Piatak at al. High levels of HIV-1 in plasma during all stages of infection determined by competitive PCR. *Science* 259:1749-1754 (1993).

Portlock. "Good risk" non-Hodgkin's lymphomas: approaches to management. *Stem Hematol.* 20(1):25-34 (1983).

Rollins. Chemokines. *Blood* 90(3):909-928 (1997).

Sallusto et al. Distinct patterns and kinetics of chemokine production regulate dendritic cell function. *Eur J Immunol.* 29:1617-1625 (1999).

Sato et al. Immunostimulatory DNA sequences necessary for effective intradermal gene immunization. *Science* 273:352-354 (1996).

Schröder. Cytokine networks in the skin. *J. Invest. Dermatol.* 105:20S-24S (1995).

Schwartzentruber et al. Tumor-infiltrating lymphocytes derived from select B-cell lymphomas secrete granulocyte-macrophage colony-stimulating factor and tumor necrosis factor-α in response to autologous tumor stimulation. *Blood* 82(4):1204-1211 (1993).

Schwarzenberger et al. Targeted gene transfer to human hematopoietic progenitor cell lines through the c-kit receptor. *Blood* 87(2):472-478 (1996).

Sirisinha et al. Autoimmune-like antibodies to the ligand-binding sites of myeloma proteins. *Proc. Natl. Acad. Sci. USA* 68(12):3130-3135 (1971).

Solari et al. Receptor-mediated endocytosis of CC-chemokines. *J. Biol. Chem.* 272(15):9617-9620 (1997).

Spellerberg et al. DNA vaccines against lymphoma: promotion of anti-idiotypic antibody responses induced by single chain Fv genes by fusion to tetanus toxin fragment C. *J. Immunol.* 159:1885-1892 (1997).

Stevenson et al. Antibody to a molecularly-defined antigen confined to a tumour cell surface. *Nature* 254:714-716 (1975).

Stevenson et al. Idiotypic determinants on the surface Immunoglobulin of neoplastic lymphocytes: a therapeutic target. *Fed. Proc.* 36(9):2268-2271 (1977).

Stevenson et al. Immunization with idiotypic immunoglobulin protects against development of B lymphocytic leukemia, but emerging tumor cells can evade antibody attack by modulation. *J. Immunol.* 130(2):970-973 (1983).

Stevenson et al. Idiotypic DNA vaccines against B-cell lymphoma. *Immunol. Rev.* 145:211-228 (1996).

Strieter et al. The functional role of the ELR motif in CXC chemokine-mediated angiogenesis. *J. Biol. Chem.* 270(45):27348-27357 (1995).

Sugai et al. Protective and cellular immune responses to idiotypic determinants on cells from a spontaneous lymphoma of NZB/NZW $F_1$ mice. *J. Exp. Med.* 140:1547-1558 (1974).

Talpas et al. H-NMR studies of bovine platelet factor 4: histidine assignments and interactions with heparin. *Biochim. Biophys. Acta.* 1078:208-218 (1991).

Tanaka et al. Proteoglycans on endothelial cells present adhesion-inducing cytokines to leukocytes. *Immunol. Today* 14(3):111-115 (1993).

Tani et al. Defensins act as potent adjuvants that promote cellular and humoral immune responses in mice to a lymphoma idiotype and carrier antigens. *International Immunology* 12(5):691-700 (2000).

Wallack. Clinical trials with VMO for melanoma. *Annals New York Academy of Sciences* 178-189 (1993).

Weber et al. Deletion of the $NH_2$-terminal residue converts monocyte chemotactic protein 1 from an activator of basophil mediator release to an eosinophil chemoattractant. *J. Exp. Med.* 183:681-685 (1996).

Weiner et al. Immunostimulatory oligodeoxynucleotides containing the CpG motif are effective as immune adjuvants in tumor antigen immunization. *Proc. Nat. Acad. Sci. USA* 94:10833-10837 (1997).

Willis et al. Immunological properties of foreign peptides in multiple display on a filamentous bacteriophage. *Gene* 128:79-83 (1993).

Winkler et al. Genetic restriction of AIDS pathogenesis by an SDF-1 chemokine gene variant. *Science* 279:389-393 (1998).

Xu et al. Monocyte chemotactic protein-3 (MCP3) interacts with multiple leukocyte receptors: binding and signaling of MCP3 through shared as well as unique receptors on monocytes and neutrophils. *Eur. J. Immunol.* 25:2612-2617 (1995).

Yamamoto et al. Highly sensitive qualitative and quantitative detection of reverse transcriptase activity. optimization, validation and comparative analysis of other detection systems. *J. Virol. Meth.* 61:135-143 (1996).

Yang et al. β-defensins: linking innate and adaptive immunity through dendritic and T cell CCR6. *Science.* 286:525-528 (1999).

Yang et al. Cutting edge: immature dendritic cells generated from monocytes in the presence of TGF-β1 express functional C-C chemokine receptor 6. *J Immunol.* 163:1737-1741 (1999).

Yang et al. Differential regulation of responsiveness to fMLP and C5a upon dendritic cell maturation: correlation with receptor expression. *J Immunol.* 165:2694-2702 (2000).

Yarchoan et al. The National Cancer institute Phase I Study of 2',3'-dideoxyinosine administration in adults with AIDS or AIDS-related complex: analysis of activity and toxicity profiles. *Reviews of Infectious Diseases* 12(5):S522-S533 (1990).

Yokoyama et al. DNA immunization can stimulate florid local inflammation, and the antiviral immunity induced varies depending on injection site. *Vaccine* 15(5):553-560 (1997).

FIGURE 1

SEQUENCE LISTING

<160> NUMBER OF SEQ ID NOS: 61

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence; Note = Synthetic Construct

<400> SEQUENCE: 1

Pro Asp Thr Arg Pro Ala Pro Gly Ser Thr Ala Pro Pro Ala His Gly
 1               5                  10                  15

Val Thr Ser Ala
            20

```
<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 2

Glu Phe Asn Asp Ala Gln Ala Pro Lys Ser Leu Glu
 1               5                  10

<210> SEQ ID NO 3
<211> LENGTH: 40
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 3

Asn Cys Thr Arg Pro Asn Asn Asn Thr Arg Lys Arg Ile Arg Ile Gln
 1               5                  10                  15

Arg Gly Pro Gly Arg Ala Phe Val Thr Ile Gly Lys Ile Gly Asn Met
            20                  25                  30

Arg Gln Ala His Cys Asn Ile Ser
        35                  40

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 4
ctcgaggtga agctggtgga gtctgga                                         27

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 5
agaggagact gtgagagtgg tgcctt                                          26

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 6
gacatccaga tgacacagtc tcca                                            24

<210> SEQ ID NO 7
<211> LENGTH: 36
<212> TYPE: DNA
<213> ORGANISM: Artificial Sequence
<220> FEATURE:
```

<223> OTHER INFORMATION: Description of Artificial Sequence; Note =
     Synthetic Construct

<400> SEQUENCE: 7 ggatccttttt atttccagct tggtcccccc tccgaa                              36

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence; Note =
     Synthetic Construct

<400> SEQUENCE: 8
ccatggtcca actgcagcag tcagggcctg ac                                  32

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence; Note =
     Synthetic Construct

<400> SEQUENCE: 9
tgaggagact gtgagttcgg taccttggcc                                     30

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence; Note =
     Synthetic Construct

<400> SEQUENCE: 10
gatgttgtga tgacgcagac tccactc                                        27

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence; Note =
     Synthetic Construct

<400> SEQUENCE: 11
ggatcctttg acttccagct ttgtgcctcc a                                   31

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence; Note =
     Synthetic Construct

<400> SEQUENCE: 12
ggggsggggs ggggsgs                                                   17

<210> SEQ ID NO 13
<211> LENGTH: 72
<212> TYPE: DNA
<213> ORGANISM: Artificial Sequence
<220> FEATURE:
<223> OTHER INFORMATION: Description of Artificial Sequence; Note =
     Synthetic Construct

<400> SEQUENCE: 13
ggatccgcag aagaacagaa actgatctca gaagaggatc tggcccacca ccatcaccat    60
cactaacccg gg    72

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 14
gaattcaacg acgctcaggc gccgaagagt ctcgag    36

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence; Note = Synthetic Construct

<400> SEQUENCE: 15

Glu Phe Asn Asp Gln Ala Pro Lys Ser Leu Glu
 1               5                  10

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 16
accatggaac ttgaccactg ccacacc    27

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 17
tgaattcaag atctttcatg tacttgcaac aggggttgtt    40

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence; Note = Synthetic Construct

<400> SEQUENCE: 18
accatggaaa aaatcaacaa tcagtaagtt gtttgagg    38

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence; Note =

-continued

Synthetic Construct

<400> SEQUENCE: 19
aaagcttcca ccatgaggac tctctgctct                           30

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 20
ctctagacac catgaacgcc aaggtcgtgg tcgtgctg                   38

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 21
tgaattccat cttgaacctc ttgtttaaag cttt                       34

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 22
accatggcaa gcaactacga ctgttgcctc                           30

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 23
atagaattcc atcttcttga ctcttaggct ga                         32

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 24
accatggatg gagggggaca ggactgct                             28

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence; Note =
      Synthetic Construct -continued

<400> SEQUENCE: 25
atagaattct cctcttgagg gctgtgtctg t                          31

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 26
aaagtcgaca aagaaaaaac gtgggtcaca atct                       34

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 27
attcccgggt tattttttctc tttgcactgt tcttctc                   37

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 28
ctctagacac catggctcgc ctacagactg cact                       34

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 29
tgaattcttg gctcagctta ttgagaatca                            30

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 30
accatggaac ttgaccactg ccacacc                               27

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 31

```
tgaattcaag atctttcatg tacttgcaac aggggttgtt                             40
```

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 32

```
accatggaaa aaatcaacaa tcagtaagtt gtttgagg                               38
```

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 33

```
ctcgagctag aattcttttc tcttgcagca tttgaggaaa                             40
```

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 34

```
aaagcttcca ccatgaggac tctctgctct                                        30
```

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 35

Asn Asp Ala Gln Ala Pro Lys Ser
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 36

Ile Gly Pro Gly Arg Ala Phe Tyr Ala
 1               5

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 37

```
ctctagacac catggctcgc ctacagactg cact                                    34
```

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 38

```
tgaattcttg gctcagctta ttgagaatca                                         30
```

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 39

```
ctctagacac catgaacgcc aaggtcgtgg tcgtgctg                                38
```

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 40

```
tgaattccat cttgaacctc ttgtttaaag cttt                                    34
```

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 41

```
accatggaac ttgaccactg ccacacc                                            27
```

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 42

```
tgaattcaag atctttcatg tacttgcaac aggggttgtt                              40
```

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 43

```
accatggaaa aaatcaacaa tcagtaagtt gtttgagg                                38
```

```
<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 44
ctcgagctag aattcttttc tcttgcagca tttgaggaaa                              40

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 45
aaagcttcca ccatgaggac tctctgctct                                        30

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 46
accatggctg ttggaagttt aaaaagtatt gga                                    33

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 47
taagcttcca ccatggcccc cgtccacgtt ttatgct                                37

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 48
tgaattcagc tatggcaggc agccgctgca tcagctgcct                             40

<210> SEQ ID NO 49
<211> LENGTH: 37
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 49
taagcttcac catggacacc aagggcatcc tgctcgt                                37

<210> SEQ ID NO 50
```

```
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 50
tgaattcgcg agcagtgact ggtaattgct gcat                                  34

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 51
accatggcgg ggtcactcgt gtcgtaca                                         28

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 52
accatgggag cgtcctggca taga                                             24

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 53
aaagctagca ccatgagggg cggagacgtc ttc                                   33

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 54
agaattccag agactcgcac ccggaccata t                                     31

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 55
accatggcac tcgcgagacg gaaatgttgt ttgaat                                36

<210> SEQ ID NO 56
<211> LENGTH: 13
<212> TYPE: PRT
```

```
<213> ORGANISM: Artificial Sequence
<220> FEATURE:
<223> OTHER INFORMATION: Description of Artificial Sequence; Note =
      Synthetic Construct

<400> SEQUENCE: 56

Ala Glu Glu Gln Lys Leu Ile Ser Glu Glu Asp Leu Ala
 1               5                  10

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 57

Asn Asp Ala Gln Ala Pro Lys Ser
 1               5

<210> SEQ ID NO 58
<211> LENGTH: 34
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 58
aaagtcgaca aagaaaaaac gtgggtcaca atct                              34

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 59
attcccgggt tattttctc tttgcactgt tcttctc                            37

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 60

Ile Gly Pro Gly Arg Ala Phe Tyr Ala
 1               5

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 61
ctcgagctag aattcttttc tcttgcagca tttgaggaaa                        40
```

DEFENSIN-ANTIGEN FUSION PROTEINS

PRIORITY CLAIM

This is a continuation of U.S. patent application Ser. No. 12/786,334, filed May 24, 2010 now U.S. Pat. No. 7,915,040, which is a divisional of U.S. patent application Ser. No. 10/380,926, filed Nov. 20, 2003, now U.S. Pat. No. 7,754,676, which is a §371 national phase of PCT Application No. PCT/US2001/029074, filed Sep. 17, 2001, which was published in English under PCT Article 2(2), and which claims the benefit of U.S. Provisional Application No. 60/233,074, filed Sep. 15, 2000. The prior Applications are incorporated herein by reference in their entirety.

FIELD OF THE INVENTION

The present invention relates to a vaccine for increasing the immunogenicity of a tumor antigen thus allowing treatment of cancer, as well as a vaccine that increases the immunogenicity of a viral antigen, thus allowing treatment of viral infection, including immunodeficiency virus (HIV) infection. In particular, the present invention provides a fusion protein comprising a defensin fused to either a tumor antigen or viral antigen which is administered as either a protein or nucleic acid vaccine to elicit an immune response effective in treating cancer or effective in treating or preventing viral infection.

BACKGROUND OF THE INVENTION

Tumor cells are known to express tumor-specific antigens on the cell surface. These antigens are believed to be poorly immunogenic, largely because they represent gene products of oncogenes or other cellular genes which are normally present in the host and are therefore not clearly recognized as nonself. Although numerous investigators have tried to target immune responses against epitopes from various tumor specific antigens, none have been successful in eliciting adequate tumor immunity in vivo (71).

Humans are particularly vulnerable to cancer as a result of an ineffective immunogenic response (72). In fact, the poor immunogenicity of relevant cancer antigens has proven to be the single greatest obstacle to successful immunotherapy with tumor vaccines (73). Over the past 30 years, literally thousands of patients have been administered tumor cell antigens as vaccine preparations, but the results of these trials have demonstrated that tumor cell immunization has failed to provide a rational basis for the design or construction of effective vaccines. Even where patients express tumor-specific antibodies or cytotoxic T-cells, this immune response does not correlate with a suppression of the associated disease. This failure of the immune system to protect the host may be due to expression of tumor antigens that are poorly immunogenic or to heterologous expression of specific antigens by various tumor cells. The appropriate presentation of tumor antigens in order to elicit an immune response effective in inhibiting tumor growth remains a central issue in the development of an effective cancer vaccine.

Anti-microbial peptides such as defensins have been identified as key elements in the innate immunity against infection. Originally identified on the basis of their anti-microbial activity, defensins are expressed within tissues and cells that frequently encounter microorganisms, and are divided into the alpha- and beta-defensin subfamilies, distinguished by cysteine residue pairing. Defensins have been suggested to play a role also in inflammation, wound repair, and regulation of the specific immune response. They induce expression of cytokines and chemokines, production of histamine and modulation of antibody responses, and they have been found to be associated with HLA-DR molecules and with lipoprotein (a) (130).

There remains a great need for a method of presenting tumor antigens, which are known to be poorly immunogenic, "self" antigens to a subject's immune system in a manner that elicits an immune response powerful enough to inhibit the growth of tumor cells in the subject. This invention overcomes the previous limitations and shortcomings in the art by providing a fusion protein comprising a defensin and a tumor antigen which can produce an in vivo immune response, resulting in the inhibition of tumor cells. There is also a continuing need for a method of presenting poorly antigenic viral antigens to a subject's immune system, particularly as relates to viral antigens such as HIV antigens. This invention also overcomes previous shortcomings in the field of viral vaccine development by providing a fusion protein comprising a defensin and a viral antigen which is effective as a vaccine for treating or preventing viral infection.

SUMMARY OF THE INVENTION

The present invention provides a fusion polypeptide comprising a defensin and a tumor antigen. In a preferred embodiment, the tumor antigen can be a B cell tumor antigen or MUC-1. The defensin of this invention can be an alpha defensin (α-def) such as human neutrophil peptide-1 (HNP-1), human neutrophil peptide-2 (HNP-2), and/or human neutrophil peptide-3 (HNP-3) (128), and/or a beta defensin (β-def), such as human β-defensin-1 (HBD1), human β-defensin-2 (HBD2) (129), murine β-defensin-2 (Def2) and/or murine β-defensin-3 (Def3).

The present invention also provides a fusion polypeptide comprising a defensin and a viral antigen. In one embodiment, the defensin can be an alpha defensin (α-def) such as human neutrophil peptide-1 (HNP-1), human neutrophil peptide-2 (HNP-2), and/or human neutrophil peptide-3 (HNP-3) (128), and/or a beta defensin (β-def), such as human β-defensin-1 (HBD1), human β-defensin-2 (HBD2) (129), Def2, and/or Def3, and the viral antigen can, for example, be an HIV antigen, such as gp120, gp160, gp41, an active fragment of gp120, an active fragment of gp160 and/or an active fragment of gp41.

In addition, the present invention provides a method of producing an immune response in a subject, comprising administering to the subject any of the fusion polypeptides of this invention, comprising a defensin and viral antigen, or a defensin and a tumor antigen, either as a protein or a nucleic acid encoding the fusion polypeptide.

Also provided is a method of treating a cancer in a subject comprising administering to the subject any of the fusion polypeptides of this invention, comprising a defensin and a tumor antigen, either as a protein or a nucleic acid encoding the fusion polypeptide.

The invention also provides a method of treating or preventing a viral infection in a subject, comprising administering to the subject any of the fusion polypeptides of this invention, comprising a defensin and a viral antigen, either as a protein or a nucleic acid encoding the fusion polypeptide.

Further provided is a method of treating or preventing HIV infection in a subject, comprising administering to the subject any of the fusion polypeptides of this invention, comprising a defensin and a human immunodeficiency virus (HIV) antigen, either as a protein or a nucleic acid encoding the fusion polypeptide.

A method of treating a B cell tumor in a subject is also provided, comprising administering to the subject any of the fusion polypeptides of this invention, comprising a defensin and a B cell tumor antigen, either as a protein or a nucleic acid encoding the fusion polypeptide.

Various other objectives and advantages of the present invention will become apparent from the following detailed description.

BRIEF DESCRIPTION OF THE DRAWING

FIG. 1 depicts the primary amino acid and consensus sequences for the α- and β-defensins. Boxes indicate the highly conserved cysteines that are numbered 1 to 6. The disulfide linkages of these bridges for α-defensins are established as 1-6, 2-4, and 3-5, whereas the disulfide linkages of the bridges for β-defensins are 1-5, 2-4, and 3-6. The amino acid sequences of the α-defensins HD-5 and HD-6 are not shown.

SEQUENCE LISTING

The Sequence Listing is submitted as an ASCII text file 4239-83275-06_Sequence_Listing, Feb. 1, 2011, 14.8 KB, which is incorporated by reference herein.

DESCRIPTION OF THE PREFERRED EMBODIMENTS

As used in the claims, "a" can include multiples. For example, "a cell" can mean a single cell or more than one cell.

The present invention is based on the unexpected discovery that the administration of a fusion protein comprising a defensin and a tumor antigen or administration of a nucleic acid encoding a fusion protein comprising a defensin and a tumor antigen yields an effective and specific anti-tumor immune response by converting a "self" tumor antigen into a potent immunogen by fusing it to a defensin moiety.

Thus, the present invention provides a fusion polypeptide comprising a defensin and a tumor antigen. The fusion polypeptide can be present in a purified form and can induce an immune response against the tumor antigen and inhibit the growth of tumor cells expressing the tumor antigen. "Purified" as used herein means the polypeptide is sufficiently free of contaminants or cell components with which proteins normally occur to allow the peptide to be used therapeutically. It is not contemplated that "purified" necessitates having a preparation that is technically totally pure (homogeneous), but purified as used herein means the fusion polypeptide is sufficiently pure to provide the polypeptide in a state where it can be used therapeutically. As used herein, "fusion polypeptide" means a polypeptide made up of two or more amino acid sequences representing peptides or polypeptides from different sources. Also as used herein, "epitope" refers to a specific amino acid sequence of limited length which, when present in the proper conformation, provides a reactive site for an antibody or T cell receptor. The identification of epitopes on antigens can be carried out by immunology protocols that are standard in the art (74). As further used herein, "tumor antigen" describes a polypeptide expressed on the cell surface of specific tumor cells and which can serve to identify the type of tumor. An epitope of the tumor antigen can be any site on the antigen that is reactive with an antibody or T cell receptor.

As used herein, "defensin" means an anti-microbial peptide with three to four intramolecular cysteine disulfide bonds which induces leukocyte migration in vitro, and/or enhances concavalin A-stimulated murine spleen cell proliferation and IFN-γ production (128). As used herein, a defensin may be either a naturally occurring defensin, i.e., a peptide which is produced by, e.g., neutrophils, intestinal Paneth cells, or epithelial cells such as those of the skin, kidney, and tracheabronchial lining, or a synthetic defensin, such as a variant of a naturally occurring defensin, which may be chemically synthesized or produced by expressing a modified cDNA encoding a naturally occurring defensin. While any mammalian or synthetic defensins may be used in the compositions and methods of the invention, naturally occurring human defensins or variants thereof are preferred.

Figure 1:
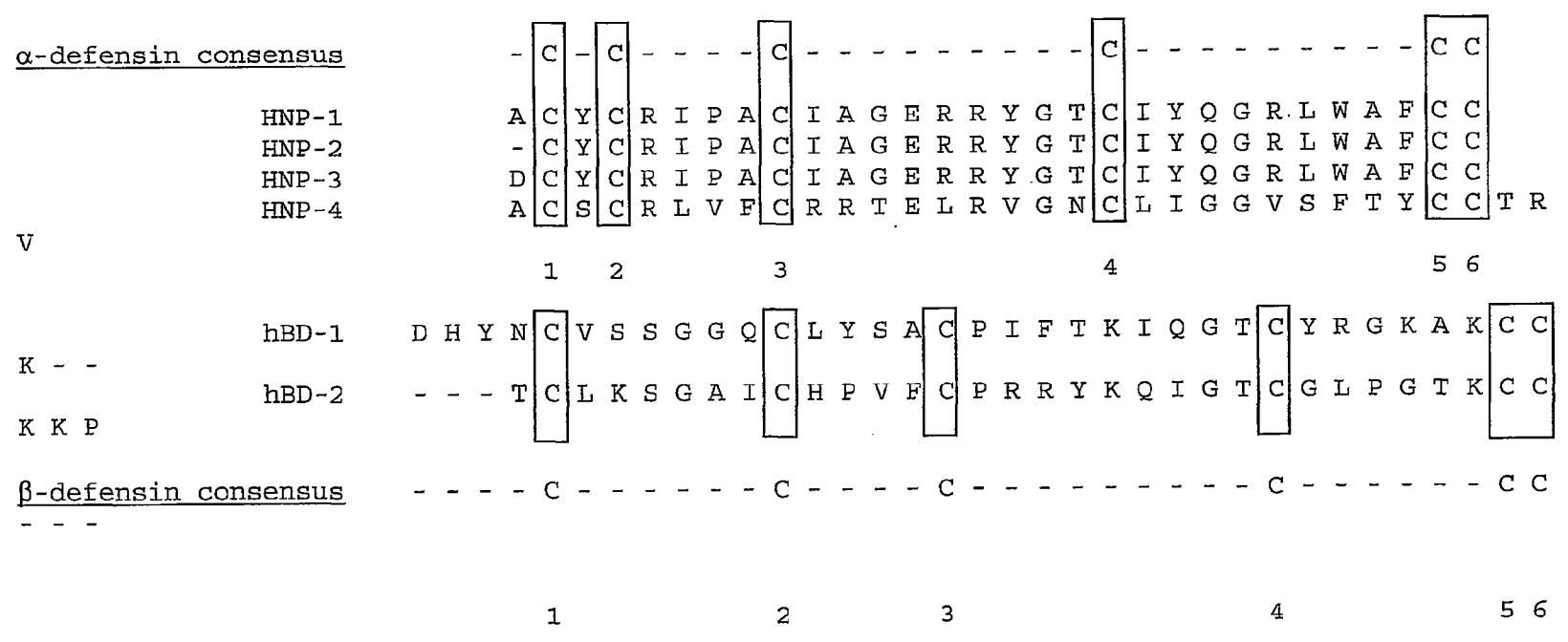

The defensins of this invention can include, but are not limited to, alpha defensins (α-defs, such as human neutrophil peptide-1 (HNP-1), human neutrophil peptide-2 (HNP-2), human neutrophil peptide-3 (HNP-3) (128, 130), human neutrophil peptide-4 (HNP-4), human defensin-5 (HD-5), and human defensin-6 (HD-6), and beta defensins (β-defs, such as human β-defensin-1 (HBD1), human β-defensin-2 (HBD2) (129, 130). Human neutrophil defensins (HNPs 1-4) are small, cationic, and arginine rich peptides that lack enzymatic activity. The peptides contain six conserved cysteine residues that participate in 3 characteristic intramolecular disulfide bridges (130, the entire contents of this reference is incorporated herein in its entirety). Cysteine pairing distinguishes β-defensins from α-defensins, wherein the former are connected 1-5, 2-4 and 3-6 and the latter are linked 1-6, 2-4 and 3-5 (FIG. 1) (130). Other examples of defensins include murine β-defensin-2 (Def2) and murine β-defensin-3 (Def3), as well as any other defensin now known or later identified.

It will be appreciated by one of skill in the art that the defensins of this invention can further include active fragments of defensins which retain the activity, including chemotaxis and inhibition of chemotaxis, of the intact molecule. The production of an active fragments of a defensin and identification of defensin fragments which retain the activity of the intact molecule are carried out according to protocols well known in the art.

To produce a nucleic acid encoding a fusion polypeptide of this invention, the defensin gene can be fragmented as desired according to standard methods and the fragments can be fused to a specific gene or gene fragment encoding an antigen to which an immune response is to be elicited (e.g., Muc-1 VNT, lymphoma scFv, gp120 etc.). The fusion polypeptide comprising the defensin fragment and the tumor or viral antigen can be produced and purified as described herein and tested for immunogenicity according to the methods provided herein. By producing several fusion polypeptides having defensin fragments of varying size, the minimal size defensin fragment which imparts an immunological effect can be identified through routine experimentation.

The tumor antigen moiety of the fusion polypeptide of this invention can be any tumor antigen now known or later identified as a tumor antigen. The appropriate tumor antigen used in the fusion polypeptide depends on the tumor type being treated. For example, the tumor antigen can be, but is not limited to human epithelial cell mucin (Muc-1; a 20 amino acid core repeat for Muc-1 glycoprotein, present on breast cancer cells and pancreatic cancer cells), the Ha-ras oncogene product, p53, carcino-embryonic antigen (CEA), the raf oncogene product, GD2, GD3, GM2, TF, sTn, MAGE-1, MAGE-3, tyrosinase, gp75, Melan-A/Mart-1, gp100, HER2/neu, EBV-LMP 1 & 2, HPV-F4, 6, 7, prostatic serum antigen (PSA), alpha-fetoprotein (AFP), CO17-1A, GA733, gp72, p53, the ras oncogene product, HPV E7 and melanoma gangliosides, as well as any other tumor antigens now known or identified in the future. Tumor antigens can be obtained following known procedures or are commercially available (79). The effectiveness of the fusion protein in eliciting an immune response against a particular tumor antigen can be determined according to methods standard in the art for determining the efficacy of vaccines and according to the methods set forth in the Examples.

Additionally, the tumor antigen of the present invention can be an antibody which can be produced by a B cell tumor (e.g., B cell lymphoma; B cell leukemia; myeloma) or the tumor antigen can be a fragment of such an antibody, which contains an epitope of the idiotype of the antibody. The epitope fragment can comprise as few as nine amino acids. For example, the tumor antigen of this invention can be a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR.

In a preferred embodiment, the tumor antigen of this invention can be a single chain antibody (scFv), comprising linked $V_H$ and $V_L$ domains and which retains the conformation and specific binding activity of the native idiotype of the antibody (27). Such single chain antibodies are well known in the art and can be produced by standard methods and as described in the Examples herein.

In addition, the tumor antigen of the present invention can be an epitope of the idiotype of a T cell receptor, which can be produced by a T cell tumor (e.g., T cell lymphoma; T cell leukemia; myeloma). The epitope can comprise as few as nine amino acids.

As will be appreciated by those skilled in the art, the invention also includes peptides and polypeptides having slight variations in amino acid sequences or other properties which do not alter the functional identity of the peptide or polypeptide. Such variations may arise naturally as allelic variations (e.g., due to genetic polymorphism) or may be produced synthetically (e.g., by mutagenesis of cloned DNA sequences), such as induced point, deletion, insertion and substitution mutations. Minor changes in amino acid sequence are generally preferred, such as conservative amino acid replacements, small internal deletions or insertions, and additions or deletions at the ends of the molecules. Substitutions may be designed based on, for example, the model of Dayhoff et al. (80). These modifications can result in changes in the amino acid sequence, provide silent mutations, modify a restriction site, or provide other specific mutations while allowing for the presentation of the functional activity of peptides and polypeptides of this invention.

The fusion polypeptides can comprise one or more selected epitopes on the same tumor antigen, one or more selected epitopes on different tumor antigens, as well as repeats of the same epitope, either in tandem or interspersed along the amino acid sequence of the fusion polypeptide. The tumor antigen can be positioned in the fusion polypeptide at the carboxy terminus of the defensin, the amino terminus of the defensin and/or at one or more internal sites within the defensin amino acid sequence. Additionally, the fusion polypeptide can comprise more than one defensin or active fragment thereof in any combination and in any order with the various tumor antigens described above.

It would be routine for an artisan to produce a fusion protein comprising any defensin moiety and any human tumor antigen (e.g., human single chain antibody) moiety according to the methods described herein, on the basis of the availability in the art of the nucleic acid and/or amino acid sequence of the defensin of interest and the human tumor antigen of interest.

The present invention further provides a fusion polypeptide comprising a first region comprising a defensin selected from the group consisting of HNP-1, HNP-2, HNP-3, HBD1, and HBD2, and a second region comprising a tumor antigen selected from the group consisting of human epithelial cell mucin (Muc-1), the Ha-ras oncogene product, p53, carcinoembryonic antigen (CEA), the raf oncogene product, GD2, GD3, GM2, TF, sTn, MAGE-1, MAGE-3, tyrosinase, gp75, Melan-A/Mart-1, gp100, HER2/neu, EBV-LMP 1 & 2, HPV-F4, 6, 7, prostatic serum antigen (PSA), alpha-fetoprotein (AFP), CO17-1A, GA733, gp72, p53, the ras oncogene product, HPV E7, proteinase 3, Wilm's tumor antigen-1, telomerase, melanoma gangliosides, an antibody produced by a B cell tumor (e.g., B cell lymphoma; B cell leukemia; myeloma), a fragment of such an antibody, which contains an epitope of the idiotype of the antibody, a malignant B cell antigen receptor, a malignant B cell immunoglobulin idiotype, a variable region of an immunoglobulin, a hypervariable region or CDR of a variable region of an immunoglobulin, a malignant T cell receptor (TCR), a variable region of a TCR and/or a hypervariable region of a TCR.

For example, the present invention provides a fusion polypeptide comprising an scFv cloned from a human subject's biopsy tumor material or from a hybridoma cell line producing a lymphoma antibody and a defensin moiety (e.g. HNP-1, HNP-2, HNP-3, HBD1, HBD2, etc.). In addition, the present invention provides a defensin fused with the Muc-1 core epitope of human breast cancer or human pancreatic cancer. Muc-1 is a glycoprotein (Mr>200,000) abundantly expressed on breast cancer cells and pancreatic tumor cells. A variable number of tandem (VNT) repeats of a 20 amino acid peptide (PDTRPAPGSTAPPAHGVTSA; SEQ ID NO:1) include B and T cell epitopes. Thus, the present invention provides a fusion protein comprising HNP-1 and Muc-1 VNT, HNP-2 and Muc-1VNT, HNP-3 and Muc-1VNT, HBD1 and Muc-1VNT, and HBD2 and Muc-1VNT. The expression vector is designed so that a VNT can be changed by routine cloning methods to produce a fusion polypeptide comprising HNP-1, HNP-2, HNP-3, HBD1, or HBD2 fused with a Muc-1 VNT dimer, trimer, tetramer, pentamer, hexamer, etc.

In specific embodiments, the present invention also provides a fusion polypeptide comprising HNP-1 and human Muc-1, HNP-2 and human Muc-1, HNP-3 and human Muc-1, HBD1 and human Muc-1, and HBD2 and human Muc-1.

The present invention further provides a fusion polypeptide comprising a defensin (e.g., HNP-1, HNP-2, HNP-3, HBD1, HBD2, etc.) and a scFv which recognizes tumor antigens, such as idiotype-specific scFv, Muc-1, etc. Such a fusion polypeptide would allow migration, recruitment and activation of specialized cells of the immune system, such as natural killer (NK) cells, macrophages, dendritic cells (DC), polymorphonuclear (PMN) leukocytes, cytotoxic lymphocytes (CTL), etc., which would destroy the target cell.

The fusion polypeptide of this invention can further comprise a spacer sequence between the defensin and the tumor antigen or viral antigen, which can have the amino acid sequence EFNDAQAPKSLE (SEQ ID NO:2), or an amino acid sequence with conservative substitutions such that it has the same functional activity as the amino acid sequence of SEQ ID NO:2, which allows for retention of the correct folding of the tumor antigen region of the polypeptide.

In addition, the present invention provides a composition comprising the fusion polypeptide of this invention and a suitable adjuvant. Such a composition can be in a pharmaceutically acceptable carrier, as described herein. As used herein, "suitable adjuvant" describes a substance capable of being combined with the fusion polypeptide to enhance an immune response in a subject without deleterious effect on the subject. A suitable adjuvant can be, but is not limited to, for example, an immunostimulatory cytokine, SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), -acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

The adjuvant, such as an immunostimulatory cytokine can be administered before the administration of the fusion protein or nucleic acid encoding the fusion protein, concurrent with the administration of the fusion protein or nucleic acid or up to five days after the administration of the fusion polypeptide or nucleic acid to a subject. QS-21, similarly to alum, complete Freund's adjuvant, SAF, etc., can be administered within hours of administration of the fusion protein or nucleic acid.

Furthermore, combinations of adjuvants, such as immunostimulatory cytokines can be co-administered to the subject before, after, or concurrent with the administration of the fusion polypeptide or nucleic acid. For example, combinations of adjuvants, such as immunostimulatory cytokines, can consist of two or more of immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants may be determined by measuring the immune response directed against the fusion polypeptide with and without the adjuvant or combination of adjuvants, using standard procedures, as described herein.

Furthermore, the present invention provides a composition comprising the fusion polypeptide of this invention or a nucleic acid encoding the fusion polypeptide of this invention and an adjuvant, such as an immunostimulatory cytokine or a nucleic acid encoding an adjuvant, such as an immunostimulatory cytokine. Such a composition can be in a pharmaceutically acceptable carrier, as described herein. The immunostimulatory cytokine used in this invention can be, but is not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules.

The present invention further contemplates a fusion polypeptide comprising a defensin, or active fragment thereof, as described herein and a viral antigen, which can be, for example, an antigen of human immunodeficiency virus (HIV). An HIV antigen of this invention can be, but is not limited to, the envelope glycoprotein gp120, the third hypervariable region of the envelope glycoprotein, gp120 of HIV-1 (the disulfate loop V3), having the amino acid sequence: NCTRPNNNTRKRIRIQRG-PGRAFVTIGKIGNMRQAHCNIS (SEQ ID NO:3), any other antigenic fragment of gp120, the envelope glycoprotein gp160, an antigenic fragment of gp160, the envelope glycoprotein gp41 and/or an antigenic fragment of gp41. For example, the nucleic acid encoding the V3 loop can be fused to the 3' end of the nucleic acid encoding a defensin (e.g., HNP-1, HNP-2, HNP-3, HBD1, or HBD2) directly or separated by nucleic acid encoding a spacer sequence. The defensin-V3 loop fusion polypeptide can be produced in an expression system as described herein and purified as also described herein.

In specific embodiments, the present invention provides a fusion polypeptide comprising a defensin and a human immunodeficiency virus (HIV) antigen, wherein the defensin can be HNP-1, HNP-2, HNP-3, HBD1, HBD2, or any other defensin, and wherein the HIV antigen can be gp120, gp160, gp41, an active (i.e., antigenic) fragment of gp120, an active (i.e., antigenic) fragment of gp160 and an active (i.e., antigenic) fragment of gp41.

Further provided in this invention is fusion polypeptide comprising any of HNP-1 and HIV gp120, HNP-2 and HIV gp120, HNP-3 and HIV gp120, HBD1 and HIV gp120, or HBD2 and HIV gp120.

An isolated nucleic acid encoding the fusion polypeptides of this invention as described above is also provided. By "isolated nucleic acid" is meant a nucleic acid molecule that is substantially free of the other nucleic acids and other components commonly found in association with nucleic acid in a cellular environment. Separation techniques for isolating nucleic acids from cells are well known in the art and include phenol extraction followed by ethanol precipitation and rapid solubilization of cells by organic solvent or detergents (81).

The nucleic acid encoding the fusion polypeptide can be any nucleic acid that functionally encodes the fusion polypeptide. To functionally encode the polypeptide (i.e., allow the nucleic acid to be expressed), the nucleic acid can include, for example, expression control sequences, such as an origin of replication, a promoter, an enhancer and necessary information processing sites, such as ribosome binding sites, RNA splice sites, polyadenylation sites and transcriptional terminator sequences. Preferred expression control sequences are promoters derived from metallothionine genes, actin genes, immunoglobulin genes, CMV, SV40, adenovirus, bovine papilloma virus, etc. A nucleic acid encoding a selected fusion polypeptide can readily be determined based upon the genetic code for the amino acid sequence of the selected fusion polypeptide and many nucleic acids will encode any selected fusion polypeptide. Modifications in the nucleic acid sequence encoding the fusion polypeptide are also contemplated. Modifications that can be useful are modifications to the sequences controlling expression of the fusion polypeptide to make production of the fusion polypeptide inducible or repressible as controlled by the appropriate inducer or repressor. Such means are standard in the art (81). The nucleic acids can be generated by means standard in the art, such as by recombinant nucleic acid techniques, as exemplified in the examples herein and by synthetic nucleic acid synthesis or in vitro enzymatic synthesis.

A vector comprising any of the nucleic acids of the present invention and a cell comprising any of the vectors of the present invention are also provided. The vectors of the invention can be in a host (e.g., cell line or transgenic animal) that can express the fusion polypeptide contemplated by the present invention.

There are numerous *E. coli* (*Escherichia coli*) expression vectors known to one of ordinary skill in the art useful for the expression of nucleic acid encoding proteins such as fusion proteins. Other microbial hosts suitable for use include bacilli, such as *Bacillus subtilis*, and other enterobacteria, such as *Salmonella, Serratia*, as well as various *Pseudomonas* species. These prokaryotic hosts can support expression vectors which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the protein. Also, the carboxy-terminal extension of the protein can be removed using standard oligonucleotide mutagenesis procedures.

Additionally, yeast expression can be used. There are several advantages to yeast expression systems. First, evidence exists that proteins produced in a yeast secretion system exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (82). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage-signal sequence. The polypeptide coding sequence can be fused in-frame to the pre-pro-alpha-factor leader region. This construct is then put under the control of a strong transcription promoter, such as the alcohol dehydrogenase I promoter or a glycolytic promoter. The protein coding sequence is followed by a translation termination codon which is followed by transcription termination signals. Alternatively, the polypeptide coding sequence of interest can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Efficient post-translational glycosylation and expression of recombinant proteins can also be achieved in Baculovirus systems in insect cells.

Mammalian cells permit the expression of proteins in an environment that favors important post-translational modifications such as folding and cysteine pairing, addition of complex carbohydrate structures and secretion of active protein. Vectors useful for the expression of proteins in mammalian cells are characterized by insertion of the protein coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary (CHO) cell line using a methotrexate resistance-encoding vector. Presence of the vector RNA in transformed cells can be confirmed by Northern blot analysis and production of a cDNA or opposite strand RNA corresponding to the protein coding sequence can be confirmed by Southern and Northern blot analysis, respectively. A number of other suitable host cell lines capable of secreting intact proteins have been developed in the art and include the CHO cell lines, HeLa cells, myeloma cell lines, Jurkat cells and the like. Expression vectors for these cells can include expression control sequences, as described above.

The vectors containing the nucleic acid sequences of interest can be transferred into the host cell by well-known methods, which vary depending on the type of cell host. For example, calcium chloride transfection is commonly utilized for prokaryotic cells, whereas calcium phosphate treatment, lipofection or electroporation may be used for other cell hosts.

Alternative vectors for the expression of protein in mammalian cells, similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been positioned to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (83).

Additionally, the fusion polypeptides and/or nucleic acids of the present invention can be used in in vitro diagnostic assays, as well as in screening assays for identifying unknown tumor antigen epitopes and fine mapping of tumor antigen epitopes.

Also provided is a method for producing a fusion polypeptide comprising a defensin, or an active fragment thereof and a tumor antigen or viral antigen, comprising cloning into an expression vector a first DNA fragment encoding a defensin or active fragment thereof and a second DNA fragment encoding a tumor antigen or viral antigen; and expressing the DNA of the expression vector in an expression system under conditions whereby the fusion polypeptide is produced. The expression vector and expression system can be of any of the types as described herein. The cloning of the first and second DNA segments into the expression vector and expression of the DNA under conditions which allow for the production of the fusion protein of this invention can be carried out as described in the Examples section included herein. The method of this invention can further comprise the step of isolating and purifying the fusion polypeptide, according to methods well known in the art and as described herein.

Any of the fusion polypeptides, the nucleic acids and the vectors of the present invention can be in a pharmaceutically acceptable carrier and in addition, can include other medicinal agents, pharmaceutical agents, carriers, diluents, adjuvants (e.g., immunostimulatory cytokines), etc. By "pharmaceutically acceptable" is meant a material that is not biologically or otherwise undesirable, i.e., the material may be administered to an individual along with the selected antigen without causing substantial deleterious biological effects or interacting in a deleterious manner with any of the other components of the composition in which it is contained. Actual methods of preparing such dosage forms are known, or will be apparent, to those skilled in this art (84).

Thus, the present invention further provides a method for inducing an immune response in a subject capable of induction of an immune response and preferably human, comprising administering to the subject an immune response-inducing amount of the fusion polypeptide of this invention. As used herein, "an immune response-inducing amount" is that amount of fusion polypeptide which is capable of producing in a subject a humoral and/or cellular immune response capable of being detected by standard methods of measurement, such as, for example, as described herein. For example, the antigenic polypeptide region can induce an antibody response. The antibodies can treat or prevent a pathological or harmful condition in the subject in which the antibodies are produced or the antibodies can be removed from the subject and administered to another subject to treat or prevent a pathological or harmful condition. The fusion polypeptide can also induce an effector T cell (cellular) immune response which is effective in treating or preventing a pathological or harmful conditions in the subject.

In an embodiment wherein the antigen moiety of the fusion polypeptide comprises an immunoglobulin light or heavy chain or a single chain antibody, the immune response can be the production in the subject of anti-idiotype antibodies, which represent the image of the original antigen and can function in a vaccine preparation to induce an immune response to a pathogenic antigen, thereby avoiding immunization with the antigen itself (85). The anti-idiotype antibodies can treat or prevent a pathological or harmful condition in the subject in which the anti-idiotype antibodies are produced or the anti-idiotype antibodies can be removed from the subject and administered to another subject to treat or prevent a pathological or harmful condition.

Further provided is a method for inhibiting the growth of tumor cells in a subject, comprising administering to the subject a tumor cell growth-inhibiting amount of the fusion polypeptide of this invention. The subject of this method can be any subject in which a humoral and/or cellular immune response to a tumor can be induced, which is preferably an animal and most preferably a human. As used herein, "inhibiting the growth of tumor cells" means that, following administration of the fusion polypeptide, a measurable humoral and/or cellular immune response against the tumor cell epitope is elicited in the subject, resulting in the inhibition of growth of tumor cells present in the subject. The humoral immune response can be measured by detection, in the serum of the subject, of antibodies reactive with the epitope of the tumor antigen present on the fusion polypeptide, according to protocols standard in the art, such as enzyme linked immunosorbent immunoassay (ELISA) and Western blotting protocols. The cellular immune response can be measured by, for example, footpad swelling in laboratory animals, peripheral blood lymphocyte (PBL) proliferation assays and PBL cytotoxicity assays, as would be known to one of ordinary skill in the art of immunology and particularly as set forth in the available handbooks and texts of immunology protocols (86).

The present invention also provides a method of treating cancer in a subject diagnosed with cancer, comprising administering to the subject an effective amount of the fusion polypeptide of the present invention. The cancer can be, but is not limited to B cell lymphoma, T cell lymphoma, myeloma, leukemia, breast cancer, pancreatic cancer, colon cancer, lung cancer, renal cancer, liver cancer, prostate cancer, melanoma and cervical cancer.

Further provided is a method of treating a B cell tumor in a subject diagnosed with a B cell tumor, comprising administering an effective amount of the fusion polypeptide of this invention, which comprises an antibody or a fragment thereof, as described herein, in a pharmaceutically acceptable carrier, to the subject.

In specific embodiments, the present invention also provides a method of producing an immune response in a subject, comprising administering to the subject a composition comprising a fusion polypeptide of this invention and a pharmaceutically acceptable carrier and wherein the fusion polypeptide can be a fusion polypeptide comprising any of HNP-1 and human Muc-1, HNP-2 and human Muc-1, HNP-3 and human Muc-1, HBD1 and human Muc-1, HBD2 and human Muc-1, Def2 and human Muc-1, and Def3 and human Muc-1.

Also provided is a method of producing an immune response in a subject, comprising administering to the subject a composition comprising a nucleic acid encoding a fusion polypeptide of this invention and a pharmaceutically acceptable carrier and wherein the fusion polypeptide is a fusion polypeptide comprising any of HNP-1 and human Muc-1, HNP-2 and human Muc-1, HNP-3 and human Muc-1, HBD1 and human Muc-1, HBD2 and human Muc-1, Def2 and human Muc-1, and Def3 and human Muc-1, under conditions whereby the nucleic acid of the composition can be expressed, thereby producing an immune response in the subject.

In further embodiments, the present invention also provides a method of producing an immune response in a subject, comprising administering to the subject a composition comprising a fusion polypeptide of this invention and a pharmaceutically acceptable carrier and wherein the fusion polypeptide can be a fusion polypeptide comprising any of HNP-1 and HIV gp120, HNP-2 and HIV gp120, HNP-3 and HIV gp120, HBD1 and HIV gp120, HBD2 and HIV gp120, Def2 and HIV gp120, or Def3 and HIV gp120, thereby producing an immune response in the subject.

Also provided is a method of producing an immune response in a subject, comprising administering to the subject a composition comprising a nucleic acid encoding a fusion polypeptide of this invention and a pharmaceutically acceptable carrier and wherein the fusion polypeptide is a fusion polypeptide comprising any of HNP-1 and HIV gp120, HNP-2 and HIV gp120, HNP-3 and HIV gp120, HBD1 and HIV gp120, HBD2 and HIV gp120, Def2 and HIV gp120, or Def3 and HIV gp120, under conditions whereby the nucleic acid of the composition can be expressed, thereby producing an immune response in the subject.

Also provided is a method of producing an immune response in a subject, comprising administering to the subject a composition comprising a fusion polypeptide and a pharmaceutically acceptable carrier and wherein the fusion polypeptide is a fusion polypeptide comprising a defensin and a human immunodeficiency virus (HIV) antigen, wherein the defensin can be HNP-1, HNP-2, HNP-3, HBD1, HBD2, Def2, Def3, or any other defensin, and wherein the HIV antigen can be gp120, gp160, gp41, an active (i.e., antigenic) fragment of gp120, an active (i.e., antigenic) fragment of gp160 and/or an active (i.e., antigenic) fragment of gp41, thereby producing an immune response in the subject.

The present invention also provides a method of producing an immune response in a subject, comprising administering to the subject a composition comprising a nucleic acid encoding a fusion polypeptide comprising a defensin and a human immunodeficiency virus (HIV) antigen, wherein the defensin can be HNP-1, HNP-2, HNP-3, HBD1, HBD2, Def2, Def3, or any other defensin, and wherein the HIV antigen can be gp120, gp160, gp41, an active (i.e., antigenic) fragment of gp120, an active (i.e., antigenic) fragment of gp160 and/or an active (i.e., antigenic) fragment of gp41, and a pharmaceutically acceptable carrier, under conditions whereby the nucleic acid can be expressed, thereby producing an immune response in the subject.

In any of the methods provided herein which recite the production of an immune response, the immune response can be humoral and/or an effector T cell (cellular) immune response, as determined according to methods standard in the art.

In another embodiment, the present invention provides a method of treating a cancer in a subject comprising administering to the subject a composition comprising a fusion polypeptide of this invention and a pharmaceutically acceptable carrier and wherein the fusion polypeptide is a fusion polypeptide comprising any of HNP-1 and human Muc-1, HNP-2 and human Muc-1, HNP-3 and human Muc-1, HBD1 and human Muc-1, HBD2 and human Muc-1, Def2 and human Muc-1, or Def3 and human Muc-1, thereby treating a cancer in the subject.

Additionally provided is a method of treating a cancer in a subject, comprising administering to the subject a composition comprising a nucleic acid encoding a fusion polypeptide of this invention and a pharmaceutically acceptable carrier and wherein the fusion polypeptide is a fusion polypeptide comprising any of HNP-1 and human Muc-1, HNP-2 and human Muc-1, HNP-3 and human Muc-1, HBD1 and human Muc-1, HBD2 and human Muc-1, Def2 and human Muc-1, or Def3 and human Muc-1, under conditions whereby the nucleic acid of the composition can be expressed, thereby treating a cancer in the subject.

Further provided is a method of treating or preventing HIV infection in a subject, comprising administering to the subject a composition comprising a defensin and a human immunodeficiency virus (HIV) antigen, wherein the defensin can be HNP-1, HNP-2, HNP-3, HBD1, HBD2, Def2, Def3, or any other defensin, and wherein the HIV antigen can be gp120, gp160, gp41, an active (i.e., antigenic) fragment of gp120, an active (i.e., antigenic) fragment of gp160 and/or an active (i.e., antigenic) fragment of gp41, and a pharmaceutically acceptable carrier, thereby treating or preventing HIV infection in the subject.

In addition, a method of treating or preventing HIV infection in a subject is provided herein, comprising administering to the subject a composition comprising a nucleic acid encoding a fusion polypeptide comprising a defensin and a human immunodeficiency virus (HIV) antigen, wherein the defensin can be HNP-1, HNP-2, HNP-3, HBD1, HBD2, Def2, Def3, or any other defensin, and wherein the HIV antigen can be gp120, gp160, gp41, an active (i.e., antigenic) fragment of gp120, an active (i.e., antigenic) fragment of gp160 and/or an active (i.e., antigenic) fragment of gp41, and a pharmaceutically acceptable carrier, under conditions whereby the nucleic acid can be expressed, thereby treating or preventing HIV infection in the subject.

Further provided is a method of treating or preventing HIV infection in a subject, comprising administering to the subject a composition comprising a fusion polypeptide comprising any of HNP-1 and HIV gp120, HNP-2 and HIV gp120, HNP-3 and HIV gp120, HBD1 and HIV gp120, HBD2 and HIV gp120, Def2 and HIV gp120, or Def3 and HIV gp120, and a pharmaceutically acceptable carrier, thereby treating or preventing HIV infection in the subject.

In addition, a method of treating or preventing HIV infection in a subject is provided herein, comprising administering to the subject a composition comprising a nucleic acid encoding a fusion polypeptide comprising any of HNP-1 and HIV gp120, HNP-2 and HIV gp120, HNP-3 and HIV gp120, HBD1 and HIV gp120, gp120, HBD2 and HIV gp120, Def2 and HIV gp120, or Def3 and HIV gp120, and a pharmaceutically acceptable carrier, under conditions whereby the nucleic acid can be expressed, thereby treating or preventing HIV infection in the subject.

In a further embodiment, the present invention provides a method of treating a B cell tumor in a subject, comprising administering to the subject a fusion polypeptide comprising a defensin and a B cell tumor antigen, wherein the B cell tumor antigen can be an antibody, a single chain antibody or an epitope of an idiotype of an antibody, and wherein the defensin can be HNP-1, HNP-2, HNP-3, HBD1, HBD2, Def2, Def3, or any other defensin, thereby treating a B cell tumor in the subject.

Also provided is a fusion polypeptide comprising the defensin HNP-1, HNP-2, HNP-3, HBD1, HBD2, Def2, Def3, or any other defensin, and the V3 loop of HIV-1 envelope glycoprotein, gp120, as well as a fusion protein comprising HNP-1, HNP-2, HNP-3, HBD1, HBD2, Def2, Def3, or any other defensin, and gp160 of HIV-1, a fusion protein comprising HNP-1, HNP-2, HNP-3, HBD1, HBD2, deft, Def3, or any other defensin, and gp41 of HIV-1, a fusion protein comprising HNP-1, HNP-3, HBD1, HBD2, Def2, Def3, or any other defensin, and an active fragment of gp120, a fusion protein comprising HNP-1, HNP-2, HNP-3, HBD1, HBD2, Def2, Def3, or any other defensin, and an active fragment of gp160 and a fusion polypeptide comprising HNP-1, HNP-2, HBD1, HBD2, Def2, Def3, or any other defensin, and an active fragment of gp41.

The methods of this invention comprising administering the fusion protein of this invention to a subject can further comprise the step of administering one or more adjuvants, such as an immunostimulatory cytokine to the subject. The adjuvant or adjuvants can be administered to the subject prior to, concurrent with and/or after the administration of the fusion protein as described herein.

The subject of the present invention can be any animal in which cancer can be treated by eliciting an immune response to a tumor antigen. In a preferred embodiment, the animal is a mammal and most preferably is a human.

To determine the effect of the administration of the fusion polypeptide on inhibition of tumor cell growth in laboratory animals, the animals can either be pre-treated with the fusion polypeptide and then challenged with a lethal dose of tumor cells, or the lethal dose of tumor cells can be administered to the animal prior to receipt of the fusion polypeptide and survival times documented. To determine the effect of administration of the fusion polypeptide on inhibition of tumor cell growth in humans, standard clinical response parameters can be analyzed.

To determine the amount of fusion polypeptide which would be an effective tumor cell growth-inhibiting amount, animals can be treated with tumor cells as described herein and varying amounts of the fusion polypeptide can be administered to the animals. Standard clinical parameters, as described herein, can be measured and that amount of fusion polypeptide effective in inhibiting tumor cell growth can be determined. These parameters, as would be known to one of ordinary skill in the art of oncology and tumor biology, can include, but are not limited to, physical examination of the subject, measurements of tumor size, X-ray studies and biopsies.

The present invention further provides a method for treating or preventing HIV infection in a human subject, comprising administering to the subject an HIV replication-inhibiting amount of the defensin/HIV antigen fusion polypeptide of this invention. As used herein, "a replication-inhibiting amount" is that amount of fusion polypeptide which produces a measurable humoral and/or effector T cell (cellular) immune response in the subject against the viral antigen, as determined by standard immunological protocols, resulting in the inhibition of HIV replication in cells of the subject, as determined by methods well known in the art for measuring HIV replication, such as viral load measurement, which can be determined by quantitative PCR (QPCR) and branched DNA (bDNA) analysis; reverse transcriptase activity measurement, in situ hybridization, Western immunoblot, ELISA and p24 gag measurement (87,88,89,90,91). The fusion polypeptide can be administered to the subject in varying amounts and the amount of the fusion polypeptide optimally effective in inhibiting HIV replication in a given subject can be determined as described herein.

The fusion polypeptide of this invention can be administered to the subject orally or parenterally, as for example, by intramuscular injection, by intraperitoneal injection, topically, transdermally, injection directly into the tumor, or the like, although subcutaneous injection is typically preferred. Immunogenic, tumor cell growth inhibiting and HIV replication inhibiting amounts of the fusion polypeptide can be determined using standard procedures, as described. Briefly, various doses of the fusion polypeptide are prepared, administered to a subject and the immunological response to each dose is determined (92). The exact dosage of the fusion polypeptide will vary from subject to subject, depending on the species, age, weight and general condition of the subject, the severity of the cancer or HIV infection that is being treated, the particular antigen being used, the mode of administration, and the like. Thus, it is not possible to specify an exact amount. However, an appropriate amount may be determined by one of ordinary skill in the art using only routine screening given the teachings herein.

Generally, the dosage of fusion protein will approximate that which is typical for the administration of vaccines, and typically, the dosage will be in the range of about 1 to 500 µg of the fusion polypeptide per dose, and preferably in the range of 50 to 250 µg of the fusion polypeptide per dose. This amount can be administered to the subject once every other week for about eight weeks or once every other month for about six months. The effects of the administration of the fusion polypeptide can be determined starting within the first month following the initial administration and continued thereafter at regular intervals, as needed, for an indefinite period of time.

For oral administration of the fusion polypeptide of this invention, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this (84).

The present invention also provides a method for producing single chain antibodies against tumor antigens comprising producing a fusion polypeptide comprising a defensin region and a region comprising a tumor antigen; immunizing animals with an amount of the fusion polypeptide sufficient to produce a humoral immune response to the fusion polypeptide; isolating spleen cells expressing immunoglobulin specific for the fusion polypeptide; isolating the immunoglobulin variable genes from the spleen cells; cloning the immunoglobulin variable genes into an expression vector; expressing the immunoglobulin variable genes in a bacteriophage; infecting E. coli cells with the bacteriophage; isolating bacteriophage from the E. coli cells which express the immunoglobulin variable genes and isolating the immunoglobulin variable gene products for use as single chain antibodies.

The defensin-scFv fusion proteins described herein would be better targets than tumor cells or purified tumor antigen peptides for antibody selection approaches such as phage displayed scFv production. For example, there are two ways to produce specific Fv displayed on the surface of phage: (1) Immunize mice with tumor cells; isolate immunoglobulin variable fragment genes from spleen cells by RT/PCR; clone the genes into bacteriophage in frame with genes coding phage surface proteins (e.g., major coat protein subunits gp VIII or gp III of the filamentous bacteriophage) (93,94); and (2) Construct semisynthetic antibody libraries by PCR as described (95). The specific phage producing scFv are selected by several rounds of binding elution and infection in E. coli, using biotin labeled defensin-tumor antigen (e.g., Muccore). The biotin enables selection of high affinity scFv-phage through binding to streptavidin conjugated magnetic beads. This approach provides simple, fast and efficient production of specific anti-tumor epitope scFv.

As described herein, the present invention also provides a nucleic acid which encodes a fusion polypeptide of this invention and a vector comprising a nucleic acid which encodes a fusion polypeptide of this invention, either of which can be in a pharmaceutically acceptable carrier. Such nucleic acids and vectors can be used in gene therapy protocols to treat cancer as well as to treat or prevent HIV infection in a subject.

Thus, the present invention further provides a method of treating a cancer in a subject diagnosed with a cancer comprising administering the nucleic acid of this invention to a cell of the subject under conditions whereby the nucleic acid is expressed in the cell, thereby treating the cancer.

A method of treating a B cell tumor in a subject diagnosed with a B cell tumor is also provided, comprising administering the nucleic acid of this invention, encoding a defensin and an antibody or fragment thereof, in a pharmaceutically acceptable carrier, to a cell of the subject, under conditions whereby the nucleic acid is expressed in the cell, thereby treating the B cell tumor.

The methods of this invention comprising administering nucleic acid encoding the fusion protein of this invention to a subject can further comprise the step of administering a nucleic acid encoding an adjuvant such as an immunostimulatory cytokine to the subject, either before, concurrent with or after the administration of the nucleic acid encoding the fusion protein, as described herein.

The nucleic acid can be administered to the cell in a virus, which can be, for example, adenovirus, retrovirus and adeno-associated virus. Alternatively, the nucleic acid of this invention can be administered to the cell in a liposome. The cell of the subject can be either in vivo or ex vivo. Also, the cell of the subject can be any cell which can take up and express exogenous nucleic acid and produce the fusion polypeptide of this invention. Thus, the fusion polypeptide of this invention can be produced by a cell which secretes it, whereby it binds a defensin receptor and is subsequently processed by an antigen presenting cell and presented to the immune system for elicitation of an immune response. Alternatively, the fusion polypeptide of this invention can be produced in an antigen presenting cell where it is processed directly and presented to the immune system.

If ex vivo methods are employed, cells or tissues can be removed and maintained outside the body according to standard protocols well known in the art. The nucleic acids of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

For in vivo methods, the nucleic acid encoding the fusion protein can be administered to the subject in a pharmaceutically acceptable carrier as described herein.

In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid to produce the fusion protein of this invention. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

Vector delivery can also be via a viral system, such as a retroviral vector system which can package a recombinant retroviral genome (see e.g., 96,97). The recombinant retrovirus can then be used to infect and thereby deliver to the infected cells nucleic acid encoding the fusion polypeptide. The exact method of introducing the exogenous nucleic acid into mammalian cells is, of course, not limited to the use of retroviral vectors. Other techniques are widely available for this procedure including the use of adenoviral vectors (98), adeno-associated viral (AAV) vectors (99), lentiviral vectors (100), pseudotyped retroviral vectors (101). Physical transduction techniques can also be used, such as liposome delivery and receptor-mediated and other endocytosis mechanisms (see, for example, 102). This invention can be used in conjunction with any of these or other commonly used gene transfer methods.

Various adenoviruses may be used in the compositions and methods described herein. For example, a nucleic acid encoding the fusion protein can be inserted within the genome of adenovirus type 5. Similarly, other types of adenovirus may be used such as type 1, type 2, etc. For an exemplary list of the adenoviruses known to be able to infect human cells and which therefore can be used in the present invention, see Fields, et al. (103). Furthermore, it is contemplated that a recombinant nucleic acid comprising an adenoviral nucleic acid from one type adenovirus can be packaged using capsid proteins from a different type adenovirus.

The adenovirus of the present invention is preferably rendered replication deficient, depending upon the specific application of the compounds and methods described herein. Methods of rendering an adenovirus replication deficient are well known in the art. For example, mutations such as point mutations, deletions, insertions and combinations thereof, can be directed toward a specific adenoviral gene or genes, such as the E1 gene. For a specific example of the generation of a replication deficient adenovirus for use in gene therapy, see WO 94/28938 (Adenovirus Vectors for Gene Therapy Sponsorship) which is incorporated herein in its entirety.

In the present invention, the nucleic acid encoding the fusion protein can be inserted within an adenoviral genome and the fusion protein encoding sequence can be positioned such that an adenovirus promoter is operatively linked to the fusion protein nucleic acid insert such that the adenoviral promoter can then direct transcription of the nucleic acid, or the fusion protein insert may contain its own adenoviral promoter. Similarly, the fusion protein insert may be positioned such that the nucleic acid encoding the fusion protein may use other adenoviral regulatory regions or sites such as splice junctions and polyadenylation signals and/or sites. Alternatively, the nucleic acid encoding the fusion protein may contain a different enhancer/promoter (e.g., CMV or RSV-LTR enhancer/promoter sequences) or other regulatory sequences, such as splice sites and polyadenylation sequences, such that the nucleic acid encoding the fusion protein may contain those sequences necessary for expression of the fusion protein and not partially or totally require these regulatory regions and/or sites of the adenovirus genome. These regulatory sites may also be derived from another source, such as a virus other than adenovirus. For example, a polyadenylation signal from SV40 or BGH may be used rather than an adenovirus, a human, or a murine polyadenylation signal. The fusion protein nucleic acid insert may, alternatively, contain some sequences necessary for expression of the nucleic acid encoding the fusion protein and derive other sequences necessary for the expression of the fusion protein nucleic acid from the adenovirus genome, or even from the host in which the recombinant adenovirus is introduced.

As another example, for administration of nucleic acid encoding the fusion protein to an individual in an AAV vector, the AAV particle can be directly injected intravenously. The AAV has a broad host range, so the vector can be used to transduce any of several cell types, but preferably cells in those organs that are well perfused with blood vessels. To more specifically administer the vector, the AAV particle can be directly injected into a target organ, such as muscle, liver or kidney. Furthermore, the vector can be administered intraarterially, directly into a body cavity, such as intraperitoneally, or directly into the central nervous system (CNS).

An AAV vector can also be administered in gene therapy procedures in various other formulations in which the vector plasmid is administered after incorporation into other delivery systems such as liposomes or systems designed to target cells by receptor-mediated or other endocytosis procedures. The AAV vector can also be incorporated into an adenovirus, retrovirus or other virus which can be used as the delivery vehicle.

As described above, the nucleic acid or vector of the present invention can be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The mode of administration of the nucleic acid or vector of the present invention can vary predictably according to the disease being treated and the tissue being targeted. For example, for administration of the nucleic acid or vector in a liposome, catheterization of an artery upstream from the target organ is a preferred mode of delivery, because it avoids significant clearance of the liposome by the lung and liver.

The nucleic acid or vector may be administered orally as described herein for oral administration of the fusion polypeptides of this invention, parenterally (e.g., intravenously), by intramuscular injection, by intraperitoneal injection, transdermally, extracorporeally, topically or the like, although intravenous administration is typically preferred. The exact amount of the nucleic acid or vector required will vary from subject to subject, depending on the species, age, weight and general condition of the subject, the severity of the disorder being treated, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein (84).

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection (104,105). Ideally, a subject will receive a single injection. If additional injections are necessary, they can be repeated at six month intervals for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety.

The present invention is more particularly described in the following examples which are intended as illustrative only since numerous modifications and variations therein will be apparent to those skilled in the art.

EXAMPLES

Example 1

Materials and Methods

Mice and tumor. C3H/HeN female mice 6 to 12 weeks of age are obtained from the Animal Production Area of the National Cancer Institute-Frederick Cancer Research and Development Center (NCI-FCRDC, Frederick, Md.). The cell line 38c13 is a carcinogen-induced murine B cell tumor cell line (125). The 38c13 tumor cell secretes and expresses IgM(κ) on the cell surface and is MHC class I positive but class II negative. 38c13 cells from a common frozen stock are passaged in vitro 3 days before use in RPMI 1640 supplemented with 100 U/ml of penicillin and streptomycin, $2 \times 10^{-5}$ M 2-mercaptoethanol and heat inactivated 10% fetal bovine serum (BioWhitaker).

Construction of expression vectors. Two types of expression systems are used to produce scFv and scFv fusions. In one system, nucleic acid encoding the fusion protein is expressed in a modified pet11d vector (Stratagene) and purified from inclusion bodies of E. coli. In the second system, the nucleic acid encoding the fusion polypeptide is cloned into a pCMVE/AB (Arya Biragyn) vector under regulatory elements of the early promoter and enhancer of CMV and expressed in the epidermis of mice as a naked DNA vaccine.

Fv fragments are cloned from two different B cell lymphomas, 38C13 and A20, respectively (106,107) by RT/PCR and produced as recombinant fusion peptides with either IP-10, respectively designated as IP10scFv38 and IP10scFv20A, or MCP3scFv38 and MCP3scFv20A. Specifically, lymphoma specific Vh and Vl fragments are cloned by RT/PCR techniques as single chain antibody from total RNA of 38c13 and A20 tumor cells, designated scFv38 and scFv20A respectively, using the following primers.

```
PRVh-5': PRV_H38-5':
                                    (SEQ ID NO: 4)
CTCGAGG TGAAGCTGGTGGAGTCTGGA

PRVh-3': PRV_H38-3':
                                    (SEQ ID NO: 5)
AGAGGAGA CTGTGAGAGTGGTGCCTT

PRV1-5': PRV_L38-5':
                                    (SEQ ID NO: 6)
GACATCCAGATGACACAGTCTCCA

PRV1-3': PRV_L38-3':
                                    (SEQ ID NO: 7)
GGATCCTTTTATTTCCAGCTTGGTCCCCCCTCCGAA

PRV_H20A-5':
                                    (SEQ ID NO: 8)
CCATGGTCCAAC TGCAGCAGTCAGGGCCTGAC

PRV_H20A-3':
                                    (SEQ ID NO: 9)
TGAGGAGACTGTGAGTTCGGTACCTT GGCC

PRV_L20A-5':
                                    (SEQ ID NO: 10)
GATGTTGTGATGACGCAGACTCCACTC

PRV_L20A-3':
                                    (SEQ ID NO: 11)
GGATCCTT TGACTTCCAGCTTTGTGCCTCCA
```

The resulting scFv contained a $(Gly_4Ser)_3$ linker and is cloned into the expression vector pET11d, which is modified to fuse in frame with c-myc and the His tag peptide sequences, followed by an amber stop codon. The resulting scFv contains a 17 a.a. residue linker, GGGGSGGGGSGGGGSGS (Gly$_4$Ser)$_3$GlySer (SEQ ID NO:12) (108).

Constructs for the nDNA vaccination are fused in frame to the following defensins lacking the pro-sequence, as defensins are first produced as inactive pro-defensins, and are activated by proteolytic cleavage of the pro sequence. Thus, the nucleic acids encoding murine β defensin-2 (Def2), murine β defensin-3(Def3), HNP-1, HNP-2, HNP-3, HBD1, or HBD2 lacking their pro sequence are inserted into pCMVE/AB to enable secretion. The carboxy-terminus of scFv is then fused in frame with the tag sequence encoding c-myc peptide and six His residues, respectively: GGA TCC GCA GAA GAA CAG AAA CTG ATC TCA GAA GAG GAT CTG GCC CAC CAC CAT CAC CAT CAC TAA CCCGGG (SEQ ID NO:13). Genes for the mature sequence (i.e., lacking the pro-sequence) of defensins HNP-1, HNP-3, HBD1, and HBD2, are cloned by RT/PCR technique from cell lines which are known in the art, and fused in frame with sFv utilizing suitable primers to form HNP-1sFv38, HNP-2sFv38, HNP-3sFv38, HBD1sFv38, and HBD2sFv38. Murine beta defensin-2 and -3 are cloned by RT/PCR from the LPS-treated murine skin and fused in frame with model lymphoma derived sFv antigen, self tumor antigen (Def2sFv38 and Def3sFv38, respectively). As controls, sFv fusion proteins with the pro-defensin form of each of the above listed defensins are prepared.

Def2, Def3, HNP-1, HNP-2, HNP-3, HBD1, and HBD2 fusions are made by fusing them to amino-terminus of scFv through a short spacer sequence: 5' GAATTC AAC GAC GCT CAG GCG CCG AAG AGT CTCGAG 3' (SEQ ID NO:14), encoding the amino acid sequence: EFNDQAPKSLE (SEQ ID NO:15). Two unique restriction endonuclease sites are introduced at the ends of the space to facilitate cloning: EcoRI at the 5' end (underlined) and XhoI at the 3' end (underlined). All constructs are verified by DNA dideoxy-sequencing method, using T7 SEQUENASE kit (Amersham).

Def2, Def3, HNP-1, HNP-2, HNP-3, HBD1, and HBD2 defensins are cloned into the scFv38 expression vector through NcoI and XhoI restriction sites. The resulting fusion nucleic acid contains the defensin gene ligated to the 5'-end of the scFv38 gene and separated with a short spacer sequence, as described above.

Bacterial expression and scFv purification. The recombinant proteins are expressed in BL21(DE3) cells (InVitrogen) as inclusion bodies after 8 hours of induction in Super-Broth with 0.8 mM IPTG in the presence of 150 μg/ml carbenicillin and 50 μg/ml ampicillin at 30° C. HNP-1-scFv38, HNP-2-scFv38, HNP-3-scFv38, HBD1-scFv38, and HBD2-scFv38, are purified from the inclusion bodies with a modified method (110). Briefly, inclusion bodies, denatured in 6M Gu HCl, 100 mM NaH$_2$PO$_4$, 10 mM Tris-HCl, pH 8.0, are reduced in 0.3M DTE and refolded at a concentration of 80 μg/ml in the refolding solution (Tris-HCl, pH 8.0, 0.5M arginine-HCL, 4 mM GSSG and 2 mM EDTA) for 72 hours at 10° C. The refolded solution is dialyzed in 100 mM Urea and 20 mM tris-HCl, pH 7.4 and the recombinant protein is purified by binding to heparin-sepharose resins (Pharmacia, Biotech, Uppsala, Sweden). The integrity and purity of the recombinant protein is tested by PAGE gel electrophoresis in reducing conditions and by Western blot hybridization with mAb 9E10. The purification yields 2-20 mg/l of the soluble protein with greater than 90% purity.

Results

Purified fusion polypeptide is tested for the ability to inhibit binding of native IgM 38c13 (Id38), as compared to positive sera from mice immunized with Id38-KLH. ELISA plates are coated with 10 μg/ml Id38, then wells are incubated with anti-Id38 positive sera (1:500) and titrated amounts of scFv. Id38 (10 μg/ml) and either Def2, Def3, HNP-1 scFv20, HNP-2 scFv20, HNP-3 scFv20, HBD1 scFv20, or HBD2 scFv20 HNP-1, HNP-2, HNP-3, HBD1, and HBD2 defensins fused to an irrelevant scFv) are used as positive and negative control samples, respectively.

Recombinant fusion proteins purified from *E. coli* are characterized for proper idiotype folding by their ability to inhibit 38c13 IgM binding to a monoclonal (SIC5 mAb) or polyclonal anti-idiotypic sera, in order to determine if Def2, Def3, HNP-1, HNP-2, HNP-3, HBD1, and HBD2 defensin fusions interfere with the proper conformation of scFv38.

Next, defensin fusions, including controls, are tested for their ability to induce chemotaxis of different subsets of immune cells, including spenocytes and bone marrow derived immature dendritic cells. Both Def2sFv38 and Def3sFv38 induce chemotaxis of murine splenocytes and murine bone marrow derived immature DC in dose dependent manner with the maximum migration to 10 ng/ml and 100 ng/ml of Def2sFv38 and Def3sFv38, respectively. The immature phenotype of these DC has been confirmed by Facs staining and by supported by their ability to migrate to MIP3, a chemo-attractant specific for immature DC, and not react to MIP3, mature DC chemo-attractant. In contrast, no chemotaxis is detected when cells incubated with proDef2sFv38 or control protein MCP3TsFv38. Moreover, day seven bone marrow derived DC, which acquired mature phenotype as judged by Facs and by inability to migrate to MIP3 while acquiring migration to MIP3, do not respond to either of defensin fusions. Therefore, murine beta defensin-2 and -3 fusion proteins target specifically immature DC inducing their chemotaxis, and do not affect mature DC.

In vivo immunization and tumor protection. To test the ability of Def2-scFv38, Def3-scFv38, HNP-1-scFv38, HNP-2-scFv38, HNP-3-scFv38, HBD1-scFv38, and HBD2-scFv38 to render self tumor antigen, sFv38, immunogenic when immunized as genetic vaccine in mice, ten mice per group are gene-gun immunized with plasmid encoding fusions with mature defensin fusions HNP-1-scFv38, HNP-2-scFv38, HNP-3-scFv38, HBD1-scFv38, and HBD2-scFv38, in order to demonstrate whether these fusions can target APC in vitro. As a control, mice are immunized with the similar DNA constructs but encoding inactive pro-defensin fusions (designated, e.g., pproDef2sFv38). Murine defensins induce significant anti-idiotype specific antibodies compared to the prototype Ig38-KLH protein vaccine. In contrast, no anti-idiotypic antibody response is seen after immunization with pro-Defensin fusions. Thus, non immunogenic sFv is rendered immunogenic by mature defensins, and the response correlates with their ability to induce chemotaxis of immature DC and other APC.

Groups of ten mice immunized with defensin or control plasmids are challenged with 20-fold lethal dose of tumor two weeks after the last of three serial immunizations. Control mice are immunized with inactive pro-defensin-sFv38 fusions or with corresponding active defensins fused with sFvA20 from irrelevant lymphoma A20 sFv or PBS. Mice immunized with inactive pproDef2sFv38 do not survive. In contrast, significant protective immunity is elicited in mice immunized with pDef2sFv38 and pDef3sFv38. The survival closely correlates with the presence of functionally intact or active defensins which can act on immature DC or other APC via differentially expressing their receptors. Although Gen-gun bombarded DNA would target variety of skin cells including skin APC and LC, it is not sufficient to render self-tumor antigen (sFv) immunogenic because it required physical linkage of sFv with defensin moieties. No positive humoral response or survival is detected in mice immunized with DNA plasmids expressing free unlinked beta defensin or viral chemokine and sFv38.

Thus, the animal experiments clearly correlate with functional data from in vitro studies. Id-specific responses and tumor immunity is detected only when the defensin moiety in the fusion retains the functional properties of the respective defensin, while no immunity is observed when the defensin is replaced with a mutant, functionally inactive defensin. Furthermore, induction of chemotaxis to the site of vaccine injection or production is not sufficient to generate immunity, as demonstrated by the lack of humoral and anti-tumor immunity in mice immunized with defensin alone or with either a mixture of free, unlinked defensin and sFv or defensin fused with an irrelevant sFv.

Example 2

Six- to nine-week old female C3H/HeN mice are immunized intraperitoneally (i.p.) with 100 to 200 μg of the soluble protein in PBS and control immunogen Id38-KLH two times at two week intervals or are shaved and immunized by Accell gene delivery device (Agracetus, Inc., Middleton, WN) with 1μ gold particles carrying 1-3 μg plasmid DNA. Sera are collected by orbital bleeding two weeks after each vaccination. Serum anti-idiotypic (anti-Id) antibody levels are tested as described (111) over microtiter plates coated with 10 μg/ml native IgM 38c13. Two weeks after the last immunization, mice are inoculated with 2000 38c13 tumor cells i.p. Survival is determined, and significance with the respect to time to death, is assessed using BMDP IL software (BMDP statistical software, Los Angeles). Mice are observed daily for any signs of toxicity and date of death and animals surviving >80 days after tumor challenge are killed and reported as long-term survivors.

Mice are immunized either with a plasmid coding for Def2-scFv38, Def3-scFv38, HNP-1-scFv38, HNP-2-scFv38, HNP-3-scFv38, HBD1-scFv38, HBD2-scFv38, or a mixture of DNA constructs expressing unlinked scFv38 and vMIPIscFv20A (scFv38D+vMIPIscfv20AD).

Ten mice per group are immunized with two types of scFv38 fused to Def2, Def3, HNP-2, HBD1, or HBD2, differing only in orientation of variable genes in scFv. Control mice receive IgM-KLH (Id38-KLH) and the corresponding defensin fusion to A20 lymphoma scFv (IP10scFv20A). Ten mice per group are immunized i.d. with plasmid coding either for defensin fusion vaccine (Def2-scFv38, Def3-scFv38, HNP-1-scFv38, HNP-2-scFv38, HNP-3-scFv38, HBD1-scFv38, and HBD2-scFv38), or free scFv (scFv38D), or viral epitope preS2 fused scFv (PreS2scFv38D).

Effector CD8$^+$ and CD4$^+$ cells are depleted two weeks after the last immunization with three i.p. injections of 400 μg α-CD8 mAb 53.6.72, or α-CD4 mAb GK1.5 (both ammonium sulfate purified ascites, Biological Resource Branch, NCI-FCRDC) (32,34), or control rat IgG (Sigma). Control mice are immunized with plasmid expressing Def2, Def3, HNP-1, HNP-2, HNP-3, HBD1, or HBD2 fused to A20 scFv (MCP3scFv20AD).

Ten Balb/C mice per group are immunized i.p. twice with 100 μg of Def2, Def3, HNP-1, HNP-2, HNP-3, HBD1, or HBD2 fused with scFv20A protein in PBS and challenged i.p. with 10$^5$ A20 tumor cells. To determine the role of free versus linked defensin, defensin-scFv20A is co-injected with the same defensin fused to an irrelevant scFv38 (defensin-scFv20A+defensin-scFv38). Control mice are immunized with A20 IgM-KLH (Id20A-KLH).

Immunoassays and serum anti-idiotypic antibody. The assessments for correct folding of purified scFv38 and fusion scFv38 are determined by ELISA with mAbs and by inhibition assay with Id38-KLH sera (immunized with native IgM 38c13 conjugated to KLH). Briefly, microtiter plates (Nunc, Naperville, Ill.) are coated overnight at 4° C. with 10 μg/ml anti-c-myc mAb 9E10 in carbonate buffer (50 mM NaHCO$_3$, pH 9.0). The wells are blocked with 5% nonfat dry milk in PBS for 30 min. Plates are washed in 0.05% Triton X-100 in PBS, and serially diluted scFv (starting from 10 μg/ml in 50 μl 2% BSA/PBS) is applied, after which plates are incubated 40 min at room temperature. After washing, the wells are incubated with 50 μl of 1:300 diluted biotinylated anti-Id38 mAb in 2% BSA/PBS for 30 min at room temperature. Wells are washed and incubated with streptavidin-HRP conjugate (1:5000) in 2% BSA/PBS for 30 min at room temperature. Then, wells are washed and incubated with ABTS peroxidase substrate (KPL, Gaithersburg, Md.) and the absorbance at 405 nm is measured.

Inhibition assays are performed as described above, except plates are coated with 10 μg/ml of native IgM 38c13, then wells are incubated for 30 min at room temperature with a 1:2 dilution of positive Id38-KLH sera mixed with serially diluted purified scFv proteins starting from 50 μg/ml in 2% BSA/PBS. The bound antibodies from the sera are assayed by incubating wells for 30 min at room temperature with anti-mouse IgG-HRP mAb (Jackson).

Serum anti-idiotypic (anti-Id) antibody levels are tested as described (37). Briefly, mouse serum is serially diluted over microtiter plates coated with 10 μg/ml native IgM 38c13. Binding of antibodies in the serum to 38c13 IgM is detected by goat anti-mouse IgG-HRP. Serum anti-Id antibody levels are quantitated by comparing sera titration curves with a standard curve obtained with a known concentration of a mixture of purified monoclonal anti-Id antibodies. Antibody levels are expressed in g/ml of serum for individual mice. In each ELISA, sera obtained from mice immunized with control IgM-KLH are included as negative controls. Such sera never showed any titration binding activity on Id-38c13.

In vitro and in vivo chemotaxis assays. Single cell suspensions are prepared from spleens of untreated C3H/HeJ mice. Murine T cell enrichment columns (R&D System, Minneapolis, Minn.) are then used to prepare a purified murine T cell population via high-affinity negative selection according to the manufacturer's instructions. The isolation procedure typically yields over 89% CD3$^+$ T cells, as determined by FACS analysis. T cell migration in vitro is assessed by 48-well microchemotaxis chamber technique. Briefly, a 26 μl aliquot of the recombinant scFv fusion protein serially diluted in the chemotaxis medium (RPMI 1640, 1% BSA, 25 mM HEPES) is placed in the lower compartment and 50 μl of cell suspension (5×10$^6$ cells/ml) is placed in the upper compartment of the chamber. The two compartments are separated by a polycarbonate filter (5 μm pore size; Neuroprobe, Cabin John, Md.) coated with 10 μg/ml of fibronectin (Sigma, St. Luis, Mo.) and incubated overnight at 4° C. or for 2 hours at 37° C. The chemotaxis assay is performed at 37° C. for 2 hours. Then the filter is removed, fixed and stained with Diff-Quik (Harlew, Gibbstown, N.J.). The number of migrated cells in three high power fields (400×) is counted by light microscopy after coding the samples. The results are expressed as the mean±SE value of the migration in triplicate samples.

Migration of splenocytes and bone marrow-derived immature dendritic cells in vitro is assessed by the 48-well micro chemotaxis chamber technique as described (112).

In order to test in vivo effects on cell accumulation, C3H/HeN mice are injected s.c. with a single 10 µg dose of scFv fusion proteins. Portions of the skin from the site of injection are removed 72 hours after the injection, fixed in 10% neutral buffered formalin, embedded in paraffin, sectioned at 5 µm and stained with hematoxylin and eosin (H&E). Slides are evaluated microscopically without knowledge of the experimental treatment.

In vivo cellular infiltration into murine skin. The numbers of PMN and mononuclear (MN) cells infiltrated into murine skin are graded as following:—, no significant lesion; 1, mild; 2, moderate; 3 severe; F, focal; MF, multi focal. Mice are injected with 10 µg of Def2-scFv38, Def3-scFv38, HNP-1-scFv38, HNP-2-scFv38, HNP-3-scFv38, HBD1-scFv38, and HBD2-scFv38, or PBS, subcutaneously. After 72 h, the injection site is excised and examined histologically on coded slides to determine the extent of infiltration. The amount of endotoxin injected with samples is 0.5-1 units.

The traditional approach to enhance immunogenicity by cross linking to KLH is not effective. Several different approaches are used for the production of single chain antibody fragments from 38c13 cells (scFv38) in *E. coli*. Yield of scFv38 differ significantly depending on the method used. Production of scFv38 through a secretory path using a PelB leader sequence as a native protein is least efficient. The problem is solved when scFv38 is produced as insoluble "inclusion" bodies, which yield about 2-8 mg of refolded scFv per liter of the batch culture with greater than 90% purity. Folding properties of the produced scFv38 are monitored by either (i) inhibition assay with native Id38; or (ii) modified ELISA assay where scFv38 is captured through an anti-c-myc tag and detected with the biotinylated monoclonal anti-Id38 antibody (anti-Id38 mAb does not recognize linear or incorrectly folded epitope). These experiments demonstrate that scFv38, but not irrelevant scFv20A, specifically binds to anti-Id38c mAb and inhibits binding of the native Id38c to anti-Id38c mAb, 50% binding inhibition by 10-15 fold excess of scFv38. In addition, positive sera from Id38c-KLH immunized mice specifically recognizes purified scFv38. These data indicate that purified scFv38 is folded correctly and imitates the idiotype of the native antibody (Id38c) of B cell lymphoma 38c13.

Immunization experiments show that scFv38, similarly to the native Id38c IgM, is a poor immunogen. Attempts were made to convert scFv38 into a potent immunogen by chemical cross linking with KLH, in analogy to the native Id38c. However, in contrast to Id38-KLH, i.p. immunizations of syngeneic mice with 100 µg of scFv38-KLH did not elicit any anti-Id38c specific antibody response. This inability to induce anti-Id38 response correlates with the loss of ability to affect binding of anti-Id38 mAb (SIC5) to Id38c by samples containing scFv38-KLH, while a control sample of an equimolar mixture of non-cross linked scFv38 and KLH (scFv38+KLH) inhibited anti-Id38/Id38c binding similarly to pure scFv38. These data indicate that a fragile Id conformation of scFv38 is removed by KLH cross linking and that this traditional approach is not applicable for the enhancement of immunogenicity of scFv38.

Design and Production of Defensin Fused scFv38. Def2-scFv38, Def3-scFv38, HNP-1-scFv38, HNP-2-scFv38, HNP-3-scFv38, HBD1-scFv38, and HBD2-scFv38 are subcloned from the relevant cell lines by RT/PCR using specific primers as described herein and inserted in frame in front of the scFv38 DNA sequence. The resulting fusion genes are designated as Def2-scFv38, Def3-scFv38, HNP-1-scFv38, HNP-2-scFv38, HNP-3-scFv38, HBD1-scFv38, and HBD2-scFv38, respectively. In order to evaluate input of the immunoglobulin V chain specific orientation, two variants of fusion defensin-scFv genes are designed, one containing a $V_H$-$V_L$ and one containing a $V_L$-$V_H$ sequence, respectively designated as scFv38 MH and scFv38(INV)MH.

All fusion proteins used in these experiments are purified from inclusion bodies of *E. coli*, solubilized and refolded as described herein. A spacer sequence, as described herein, is introduced into the defensin fusion proteins and correct folding is tested for each recombinant protein.

The ability of Def2-scFv38, Def3-scFv38, HNP-1-scFv38, HNP-2-scFv38, HNP-3-scFv38, HBD1-scFv38, and HBD2-scFv38 proteins to induce chemotaxis in vivo in C3H/HeN mice is also tested. Mice are s.c. injected once with 10 µg of the fusion protein and after 72 hours, the skin around the site of injection is removed and analyzed as described herein.

Production of fusion polypeptides comprising a human defensin and a human tumor antigen or HIV antigen. To produce the fusion polypeptides of the present invention which comprise a defensin region and a human tumor antigen region or HIV antigen region, the following procedures are carried out: Tumor or viral antigen is cloned by PCR or RT/PCR from DNA or RNA of biopsy cells of a patient, using specific primer. The primers are made using standard methods for selecting and synthesizing primer sequences from analysis of known sequences of the genes of interest (e.g., from GenBank, Kabat Ig sequence database and other available genetic databases, as are known in the art). For example, lymphoma or myeloma-specific scFv is cloned by RT/PCR from the nucleic acid from a patient's lymphoma or myeloma biopsy cells or from nucleic acid from hybridoma cells expressing the patient's immunoglobulin. Several sets of primers are used to clone human variable (V) genes based on GenBank and Kabat IG sequence data. As in cloning murine scFv, human tumor V fragments are cloned and sequenced using a family-specific primer or primer mixture for leader and constant region sequences. Next, scFv is constructed using primers based on the sequence of each V gene cloned. These primers can have specific restriction endonuclease sites to facilitate routine cloning, or scFv is made by overlapping PCR, according to methods well known in the art. The vector expressing the fusion polypeptide can contain several unique restriction endonuclease sites (e.g., XhoI, BamHI) between the 3' end of the spacer sequence and the 5' end of the c-myc and six His tag sequences, or the 5' end of the polyA transcription terminator region (if a SmaI site is used), thus enabling routine cloning of any scFv, tumor antigen or viral antigen.

As described herein, nucleic acid encoding the defensin-tumor antigen fusion polypeptides of this invention is expressed in yeast (e.g., *Saccharomyces cerevisiae*; *Pichia pastoris*, etc.) or in mammalian cell culture, according to methods standard in the art. The proteins produced in these systems are affinity purified with anti-c-myc antibodies (e.g., 9E10; M5546, Sigma) or anti-poly-His antibodies (e.g., H1029, Sigma). Alternatively, immobilized metal chelate affinity chromatography (Ni-NTA resin, Qiagen) is used for purification of soluble or refolded fusion polypeptides.

Administration of fusion polypeptides to human subjects. Immunity and suppression of tumor growth in a human subject. To elicit a tumor cell growth-inhibiting response in a human subject, a fusion polypeptide comprising a defensin and a tumor antigen which is present in the human subject is administered to the subject subcutaneously in a dose ranging from 1 to 500 µg of the fusion polypeptide once weekly for about eight weeks or once monthly for about six months. Within the first month following the initial immunization, blood samples can be taken from the subject and analyzed to determine the effects of administration of the fusion polypeptide. Particularly, the presence in the subject's serum, of antibodies reactive with the tumor antigen in the fusion protein can be determined by ELISA, Western blotting or radioimmunoprecipitation, or other methods for detecting the formation of antigen/antibody complexes as would be standard practice for one of ordinary skill in the art of immunology. Also, a cellular immune response to the tumor antigen in the fusion polypeptide can be detected by peripheral blood lymphocyte (PBL) proliferation assays, PBL cytotoxicity assays, cytokine measurements, or other methods for detecting delayed type hypersensitivity and cellular immune response, as would be standard practice for one of ordinary skill in the art of immunology. Additionally, the kinetics of tumor growth and inhibition of tumor cell growth can be determined by monitoring the subject's clinical response, through physical examination, tumor measurement, x-ray analysis and biopsy. The exact dosage can be determined for a given subject by following the teachings as set forth herein, as would be standard practice for one of ordinary skill in the art of vaccine development.

Example 3

Using various chemokines and defensins, this example demonstrates that protective antitumor immunity can be obtained by targeting immature, but not mature DC. Thus, MIP-3α and β-defensins render otherwise non-immunogenic tumor antigens immunogenic and induce protective and therapeutic antitumor immunity. In contrast, immunizations with homeostatic chemokines SLC or SDF1β do not elicit antitumor immunity. While both humoral and cellular immune responses are useful for treatment of the more aggressive 38C13 tumor that expresses IgM primarily on its surface (Campbell, M. J., L. Esserman, N. E. Byars, A. C. Allison, and R. Levy. 1990. Idiotype vaccination against murine B cell lymphoma. Humoral and cellular requirements for the full expression of antitumor immunity. *J. Immunol.* 145:1029; Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253) cellular immunity is protective for slower growing A20 lymphoma, which largely secretes its idiotypic antigen. Thus, the breadth of the disclosed compositions and methods as a generally useful for vaccines was also made apparent by its ability to elicit for the first time eradication of established A20 lymphoma.

Materials and Methods

Fusion gene cloning and plasmid constructions. Cloning strategy for lymphoma specific $V_H$ and $V_L$ fragments from 38C13 (Bergmann Y. and Haimovich, J. 1977. Characterization of a carcinogen-induced murine B lymphocyte cell line of C3H/eb origin. *J. Immunol.* 7: 413) and A20 (Kim, K. J Kanellopoulos, Langevin C., Merwin, R. M., Sachs, D. H., and Asofsky, R. 1979. Establishment and characterization of BALB/c lymphoma lines with B cell properties. *J. Immunol.* 122(2): 549) cells as sFv38 and sFv20, respectively, with MCP-3 and IP-10 are described elsewhere (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). Genes for mature murine β-defensins were cloned from LPS (10 ng/ml) treated BALB/c mouse skin in frame to the 5'-end of sFv by RT/PCR from total RNA using specific primers as described previously (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). The following pairs of primers were used for β-defensin 2 (GeneBank #AJ011800) PRmDF2β-5' (ACCATGGAACTTGACCACTGCCACACC; SEQ ID NO:16) and PRmDF2β-3' (TGAATTCAAGATCTTTCATG-TACTTGCAACAGGGGTTGTT; SEQ ID NO:17) and for β-defensin 3 (GeneBank #AF092929) PRmDF3β-5' (AC-CATGGAAAAAATCAACAATCAGTAAGT-TGTTTGAGG; SEQ ID NO:18) and PRmDF3β-3' (CTC-GAGCTAGAATTCTTTTCTCTTGCAGCATTTGAGGAA A; SEQ ID NO:61). β-pro-defensin 2 gene was cloned for eukaryotic expression using PRproDF2β L-5' (AAAGCTTC-CACCATGAGGACTCTCTGCTCT; SEQ ID NO:19) and PRmDF2β-3', which contained native secretion signal sequence. SDF-1β (GeneBank #HSU16752) was cloned from 10 ng/ml LPS treated human monocytes using PRhSDF1β-5' (CTCTAGACACCATGAACGCCAAG-GTCGTGGTCGTGCTG; SEQ ID NO:20) and PRhSDF1β-3' (TGAATTCCATCTTGAACCTCTTGTTTAAAGCTTT; SEQ ID NO:21). Murine MIP-3α (GeneBank #AJ222694) was cloned from mixture of thymus and kidney cDNA using PRmMTP3α-5' (ACCATGGCAAGCAACTACGACTGT-TGCCTC; SEQ ID NO:22) and PRmMIP3α-3' (ATAGAAT-TCCATCTTCTTGACTCTTAGGCTGA; SEQ ID NO:23). Murine SLC (GeneBank #U88322) was recloned from the plasmid (gift of Dr. Shakhov, SAIC-Fredeick) using PRmSLC-5' (ACCATGGATGGAGGGGGACAGGACT-GCT; SEQ ID NO:24) and PRmSLC-3' (ATAGAATTCTC-CTCTTGAGGGCTGTGTCTGT; SEQ ID NO:25). All constructs were verified by DNA dideoxy-sequencing method (Amersham, USA) and purified using plasmid purification kit (Qiagen, Valencia, Calif.).

Recombinant fusion proteins purified as inclusion bodies after 8 hours of induction in Super-Broth (Digene Diagnostics, Inc., Beltsville, Md.) with 0.8 mM IPTG as described elsewhere (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253), and refolded according to Buchner et al (Buchner, J., Pastan, I., and Brinkmann, U. 1992. A method for increasing the yield of properly folded recombinant fusion proteins: single-chain immunotoxins from renaturation of bacterial inclusion bodies. *Anal. Biochem.* 205(2): 263). The refolded fusion proteins were purified by heparin-sepharose chromatography (Pharmacia Biotech, Uppsala, Sweden). The integrity and purity (greater than 90%) of recombinant proteins were tested by PAGE and by western blot hybridization with 9E10 anti c-myc mAb (Sigma). Correct folding of purified sFv38 proteins were determined by the ability to bind to anti-idiotype mAb S1C5 in ELISA (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). Briefly, serially diluted sFv were added to microtiter plates coated with 10 mg/ml anti c-myc mAb 9E10. After washing, plates were incubated with a 1:300 diluted biotin-labeled S1C5, followed with streptavidin-HRP (1:5000, Jackson Lab., Inc., Bar Harbor, Me.) and developed with ABTS peroxidase substrate (KPL, Gaithersburg, Md.). Proteins were biotinilated using EZ-Link Sulfo-NHS-LC-Biotin following manufacturer's protocol (Pierce).

Isolation of murine bone marrow derived dendritic cells (Fields, R. C., Osterholzer, J. J., Fuller, J. A., Thomas, E. K., Geraghty, P. J., and Mule, J. J. 1998. Comparative analysis of murine dendritic cells derived from spleen and bone marrow. *J. Immunother.* 21: 323). Briefly, bone marrow was collected from tibias and femurs of 4 to 6 months old BALB/c mice. Erythrocytes were lysed with ACK lysis buffer (BioWhittaker, Walkersville, Md.). CD8+, CD4+, B220+ and I-A$^b$ cells were depleted using a mixture of mAbs and rabbit complement. The mAbs were TIB-146 (anti-B220), TIB-150 (anti-CD8), TIB-207 (anti-CD4), TIB-229 (anti-I-A$^b$) obtained from ATCC. Cells were cultured in DC medium (RPMI 1640 containing 5% heat inactivated fetal bovine serum, 1% penicillin, streptomycin, 1% L-glutamine and 5×10$^{-5}$ 2-ME) containing 10 ng/mL each of murine IL-4 and GM-CSF (Pepro-tech). Adherent cells were harvested on day 4 and day 7 and used in subsequent experiments. DC were matured by TNFα (10 ng/ml, PharMingen), overnight in DC medium. iDC at day four—five cultivation were in general CD11+ (69%), B7.2+ and I-A$^{b+}$ (21%), B7.2$^-$ and I-A$^{b+}$ (18%), CD40+ (27%). Upon maturation the DC were CD11c+ (87%), B7.2+ and I-A$^{b+}$ (62%), B7.2$^-$ and I-A$^{b+}$ (3%), CD40+ (87%). The following mAb used in FACS: CD-11c-APC, MAC3-PE, Gr-1-FITC, B220-PE, Thy 1.2-FITC, I-A$^b$-FITC, B7.2-PE, CD40-PE (PharMingen).

In vitro chemotaxis assay: The migration of DC (50 ml, 10$^6$ cells/ml) was assessed using a 48-well microchemotaxis chamber (Neuro Probe, Cabin John, Mass.) with a 5-mm polycarbonate filter (Osmonics, Livermore, Calif.) as described (Falk, W., Goodwin, R. H. Jr, and Leonard, E. J. 1980. A 48-well micro chemotaxis assembly for rapid and accurate measurement of leukocyte migration. *J. Immunol Methods* 33(3): 239; Yang, D., Chen, Q., Stoll, S., Chen, X., Howard, O. M., and Oppenheim, J. J. 2000. Differential regulation of responsiveness to fMLP and C5a upon dendritic cell maturation: correlation with receptor expression. *J. Immunol* 165(5):2694). Cells were incubated at 37° C. in humidified air with 5% CO$_2$ for 1.5 h. DC migrating across the filter were counted using a Bioquant semiautomatic counting system. The results (as the mean±SE of triplicate samples) are presented as chemotactic index (C. I.) defined as the fold increase in the number of migrating cells in the presence of test factors over the spontaneous cell migration (in the absence of test factors). Human MIP-3α and MIP-3β were from PeproTech (Rocky Hill, N.J.).

Cell lines and mice. The carcinogen-induced, C3H 38C-13 B cell lymphoma is described by Bergmanm Y. and Haimovich, J. 1977. Characterization of a carcinogen-induced murine B lymphocyte cell line of C3H/eb origin. *J. Immunol.* 7: 413. The 38C-13 tumor secretes and expresses IgM (k) on the cell surface. The BALB/c A20 lymphoma (Kim, K. J., Kanellopoulos, Langevin C., Merwin, R. M., Sachs, D. H., and Asofsky, R. 1979. Establishment and characterization of BALB/c lymphoma lines with B cell properties. *J. Immunol.* 122(2): 549) was from the American Type Culture Collection (ATCC, Rockville, Md.) and expresses IgGk. Murine CCR6 expressing HEK293 cells (HEK293/CCR6) were obtained from Dr. Farber, J. (NIAID/NIH).

Flow cytometric analysis. Trypsinized 2.5×10$^6$ (HEK293/CCR6 or HEK293) cells/ml were incubated with 20 mg/ml biotinilated mMIP3asFv38 for 30 min on ice in PBS with 2% BSA (PBS/BSA) and 20% mouse sera. Cells were stained on ice for 30 min with 0.2 mg/ml Streptavidin-PE (Pharmingen) and fixed with 1% paraformaldehyde.

In vivo immunizations and tumor protection experiment. Animal care was provided in accordance with the procedures outlined in a Guide for the Care and Use of Laboratory Animals (NIH Publication No. 86-23, 1985). Six- to nine-week old female C3H/HeNCrlBR or BALB/c mice (Charles River Laboratories, Frederick, Md.) were used. Mice (10 per group) were immunized with Helios Gene Gun System (Bio-Rad, Hercules, Calif.) with 1-2 mg plasmid DNA three times every two weeks as described (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). Two weeks after the last immunization, mice were challenged i.p. with 2×10$^3$ or 2.5×10$^5$ 38C13 or A20 lymphoma cells, respectively, and followed for survival. Differences in survival between groups were determined by non-parametric logrank test (BMDP statistical software, Los Angeles). P-values refer to comparison with group immunized with DNA expressing the same chemokine or defensin fused with an irrelevant sFv, or sFv fused with mutant chemokine, unless specified.

Therapy of established tumor with DNA vaccine. Six- to nine-week old female BALB/c mice (ten per group) were challenged with 2.5×10$^5$ syngeneic A20 tumor cells. At day 1, 4, 8 and 18 these mice were gene-gun immunized with DNA plasmid (containing about 1-2 mg DNA per immunization) and mice followed for tumor progression.

Adoptive transfer experiments. BALB/c mice were gene gun immunized with 1-2 mg pMCP3sFv20 twice biweekly and splenocytes and sera were removed ten days after the last immunization. Ten BALB/c mice per group were i.p. injected in saline with 2.5×10$^5$ A20 tumor cells per mouse mixed with 2×10$^7$ splenocytes or sera from immune or mock treated mice and mice followed for tumor progression.

Results

Murine β-defensins and chemokines retain their functional integrity as fusion proteins with sFv and chemo-attract immature, but not mature, DC. First, a variety of chemokine and β-defensin fusion proteins were cloned and purified with sFv, a lymphoma Ig-derived non-immunogenic Fv from the two different B cell lymphomas 38C-13 and A20 (Table 1).

TABLE 1

Ligand-Antigen fusion constructs

| DNA vaccine name | Ligand: Defensin or chemokine | Antigen | Protein Name | Description |
| --- | --- | --- | --- | --- |
| Antigen alone | | | | |
| psFv38 | none | sFv38 | sFv38 | Single chain antibody fragment from 38C-13 lymphoma |
| psFv20 | none | sFv20 | sFv20 | Single chain antibody fragment from A20 lymphoma |
| Defensin fusions: | | | | |
| pmDF2βsFv38 | murine β-defensin 2 | sFv38 | mDF2βsFv38 | Murine β-defensin 2 fusion with sFv38 |
| pmDF3βsFv38 | murine β-defensin 3 | sFv38 | mDF3βsFv38 | Murine β-defensin 3 fusion with sFv38 |
| pproDF2βsFv38 | murine pro-β-defensin 2 | sFv38 | mproDF2βsFv38 | Murine pro-β-defensin 2 fusion with sFv38 |
| pmDF2βsFv20 | murine β-defensin 2 | sFv20 | mDF2βsFv20 | Murine β-defensin 2 fusion with sFv20 |
| pmSF3βsFv20 | murine β-defensin 3 | sFv20 | mDF3βsFv20 | Murine β-defensin 3 fusion with sFv20 |

TABLE 1-continued

Ligand-Antigen fusion constructs

| DNA vaccine name | Ligand: Defensin or chemokine | Antigen | Protein Name | Description |
|---|---|---|---|---|
| Inflammatory chemokine fusions: | | | | |
| pmMIP3αsFv38 | murine MIP3α | sFv38 | mMIP3αsFv38 | Murine MIP3α fused with sFv38 |
| pmMIP3αsFv20 | murine MIP3α | sFv20 | mMIP3αsFv20 | Murine MIP3α fused with sFv20 |
| pmIP10sFv38 | murine IP-10 | sFv38 | mIP10sFv38 | Murine IP-10 fused with sFv38 |
| pmIP10sFv20 | murine IP-10 | sFv20 | mIP10sFv20 | Murine IP-10 fused with sFv20 |
| pMCP3sFv38 | human MCP-3 | sFv38 | MCP3sFv38 | human MCP-3 fused with sFv38 |
| pMCP3sFv20 | human MCP-3 | sFv20 | MCP3sFv20 | human MCP-3 fused with sFv20 |
| Homeostatic chemokine fusions: | | | | |
| pmSLCsFv38 | murine SLC | sFv38 | mSLCsFv38 | murine SLC fused with sFv38 |
| pmSDF1βsFv38 | human SDF1β | sFv38 | SDF1βsFv38 | human SDF1β fused with sFv38 |
| Control fusions: | | | | |
| pmDF3βMuc1 | murine β-defensin 3 | Muc1 | mDF3βMuc1 | Murine β-defensin 2 fusion with Muc1 |
| phMCP3-EGFP | hMCP-3 | EGFP | hMCP3-EGFP | human MCP-3 fusion with EGFP |
| phMDC-EGFP | hMDC | EGFP | hMDC-EGFP | human MDC fusion with EGFP |
| pMC148MsFv38 | viral, MC148 | SFv38 | MC148MsFv38 | Viral MC148 fusion with sFv38 |
| Protein vaccine: | | | | |
| Ig38-KLH | None | Ig38 | Ig38-KLH | 38C-13 lymphoma derived IgM protein cross-linked with KLH |
| Ig20-KLH | None | Ig20 | Ig20-KLH | A20 lymphoma derived IgG2a protein cross-linked with KLH |

For example, sFv fusion proteins with murine inflammatory chemokine MIP-3α, murine β-defensin 2 and β-defensin 3 were designated mMIP3α sFv38, mDF2β sFv38 and mDF3β sFv38, or mMIP3α sFv20, mDF2β sFv20 and mDF3β sFv20, respectively. Similarly, sFv fusion proteins with homeostatic chemokines SLC and SDF1β were designated mSLCsFv38 and SDF1β sFv38, respectively. Control proteins contained either sFv fusions with mutant chemokine, generated by replacing the first Cys residue with Ser or by truncation of the amino-termini to abrogate a respective receptor binding, or an inactive form pro-defensin 2, β-defensin 2 with its pro-sequence (mproDF2β sFv38, Table 1). All fusion proteins had comparable idiotype folding, as tested by inhibition ELISA with monoclonal anti-Id antibodies, which bind only properly folded parental lymphoma Id.

The functional integrity of these proteins was tested by their ability to induce chemotaxis of murine APC and THP-1 cells and binding to the chemokine receptor transfected cells. CCR6 transfected, but not parental HEK293 cells specifically stained with biotinylated murine MIP3α fusion protein. Furthermore, as expected, chemokine fusion proteins, but not control mutant fusion proteins, induced chemotaxis of THP-1 cells or murine DC. Since human β-defensin 2 was reported to interact with CCR6, murine β-defensin fusion proteins was tested for their ability to induce chemotaxis of murine CCR6 transfected cells, HEK293/CCR6. These cells were chemoattracted by murine MIP3a (a ligand of CCR6) fusion protein (mMIP3α sFv38). Both fusion proteins β-defensin 2 and 3, but not fusion proteins β-defensin 2 containing pro-sequence (mproDF2β 2sFv38) or control viral chemokine (vMIP1MsFv38), chemo-attracted murine CCR6 expressing cells, in a dose dependent manner. A control parental cell line, HEK293, which does not express CCR6 was not attracted to these proteins. Next, we tested the ability of these proteins to attract murine bone marrow derived DC (which are known to express CCR6; Sallusto, F., Palermo, B., Lenig, D., Miettinen, M., Matikainen, S., Julkunen, I., Forster, R., Burgstahler, R., Lipp, M., and Lanzavecchia, A. 1999. Distinct patterns and kinetics of chemokine production regulate dendritic cell function. Eur. J. Immunol 29(5): 1617; Sallusto, F., P. Schaerli, P. Loetscher, C. Schaniel, D. Lenig, C. R. Mackay, S. Qin, and A. Lanzavecchia. 1998. Rapid and coordinated switch in chemokine receptor expression during dendritic cell maturation. Eur. J. Immunol 28:2760) was tested. The purity of murine bone marrow derived DC cells and their immature phenotype at day four of cultivation was confirmed by expressions of CD11c[+] and low levels of I-A, B7.2 and CD40 respectively (see Methods). Similarly to MIP3α, both β-defensin fusion proteins induced chemotaxis of immature DC in a dose dependent manner with peak activity at 10 ng/ml and 100 ng/ml for mDF2β sFv38 and mDF3bsFv38, respectively. The predominant immature phenotype of these DC was also supported by their ability to migrate to human MIP3α, a chemo-attractant specific for CCR6[+] immature DC (Dieu, M. C., Vanbervliet, B., Vicari, A., Bridon, J. M., Oldham, E., Ait-Yahia, S., Briere, F., Zlotnik, A., Lebecque, S., and Caux, C. 1998. Selective recruitment of immature and mature dendritic cells by distinct chemokines expressed in different anatomic sites. J. Exp. Med. 188(2): 373; Yang, D., Howard, O. M., Chen, Q., and Oppenheim, J. J. 1999. Cutting edge: immature dendritic cells generated from monocytes in the presence of TGF-beta 1 express functional C-C chemokine receptor 6. J. Immunol 163(4): 1737), and their limited ability to react to human MIP3β (Sallusto, F., Palermo, B., Lenig, D., Miettinen, M., Matikainen, S., Julkunen, I., Forster, R., Burgstahler, R., Lipp, M., and Lanzavecchia, A. 1999. Distinct patterns and kinetics of chemokine production regulate dendritic cell function. Eur. J. Immunol 29(5): 1617), a chemoattractant specific for CCR7[+] mature DC. In contrast, none of the defensin and MIP3α fusion proteins stimulated chemotaxis of TNF-induced mature DC, which migrated to MIP3β. Furthermore, control fusion protein with mutant MIP3a or mproDF2β sFv38 did not induce chemotaxis of any DC. Therefore, murine β-defensin 2 and 3 fusion proteins can specifically target iDC and induce their CCR6-mediated chemotaxis, similarly to MIP3α.

Effect of murine β-defensin or inflammatory chemokine fusion constructs on capacity of non-immunogenic tumor antigens to induce humoral immunity. Lymphoma idiotype alone is non-immunogenic in syngeneic mice. Similarly, DNA immunizations with lymphoma derived Fv or sFv alone, particularly from 38C13 and A20 lymphomas, do not induce immunity in syngeneic mice (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). Therefore, a fusion construct of inflammatory peptides, such as MIP3α or β-defensins, with these sFv antigens was used to demonstrate that it would induce specific immunity when administered as a DNA vaccine in mice. Ten mice per group were immunized by gene-gun with plasmids encoding fusion proteins consisting of mature forms of β-defensins (pmDF2β sFv38 and pmDF3β sFv38, respectively) or MIP3α (pmMIP3α sFv38). Control mice were immunized with DNA constructs encoding sFv fused with inactive pro-Defensin (pproDF2β sFv38), or mutated and inactive chemokines (pvMC148MsFv38). As will be discussed later, no antibody was generated when mice were immunized with 2 mg DNA expressing a mixture of plasmids containing unlinked sFv and murine β-defensin (pmDF3β Muc1+sFv38) or chemokine. In contrast, mice immunized with plasmids encoding sFv fusion proteins with murine β-defensins, MIP3α or SLC produced idiotype-specific antibody levels comparable to the levels induced by vaccination with tumor-derived intact Ig protein conjugated to KLH. However, control mice immunized with an inactive pro-β-defensin (pproDef2β sFv38) or mutant chemokine sFv fusion constructs (pvMC148MsFv38), or sFv38 alone did not produce any anti-Id antibody responses. Interestingly, the two types of β-defensins differed in their capacity to elicit antibody responses elicited, though both produced predominantly specific IgG1 antibodies, β-defensin 3 was superior to β-defensin 2 for induction of specific antibodies to every antigen tested.

β-defensin fusion vaccines elicit protective and therapeutic antitumor immunity. The vaccine protocol used to elicit protective antitumor immunity was as follows: first, immunizing mice with 2 mg DNA constructs three times with biweekly intervals, then, two weeks after the last immunization, challenging them with a 20-fold lethal dose of syngeneic tumor. No survival was observed in control groups immunized with PBS or plasmids encoding sFv38 fused with inactive pro-β-defensin-2 (pproDef2β sFv38), with irrelevant chemokine plasmid vaccines pMDC-EGFP or with mutant constructs pMC148MsFv38. In contrast, significant protective immunity was elicited in mice immunized with pmDF2β sFv38 or pmDF3β sFv38 (logrank P<0.001 and 0.004 as compared with pproDF2β sFv38 and pMC148MsFv38, respectively). The protection elicited with both β-defensin constructs was comparable to one induced by Ig-KLH protein vaccine, a prototype vaccine which consists of lymphoma derived IgM cross-linked with KLH, being successfully tested in phase III clinical trial (Bendandi, M., Gocke, C. D., Kobrin, C. B., Benko, F. A., Sternas, L. A., Pennington, R., Watson, T. M., Reynolds, C. W., Gause, B. L., Duffey, P. L., Jaffe, E. S., Creekmore, S. P., Longo, D. L., and Kwak, L. W. 1999. Complete molecular remissions induced by patient-specific vaccination plus granulocyte-monocyte colony-stimulating factor against lymphoma. *Nat. Med.* 5(10): 1171). Similarly, DNA immunizations with MIP3a fusions elicited potent tumor protection (pmMIP3α sFv38, logrank P<0.0001 as compared with pMC148MsFv38). In contrast, none of mice immunized with constructs encoding sFv fusion with homeostatic chemokine murine SLC were protected (pmSLCsFv38, logrank p*<0.02 compared with pmMIP3α sFv38), despite the fact that this SLC fusion construct generated anti-Id specific antibodies comparable to pmMIP3α sFv38 vaccinated group. Moreover, no immunity was detected in mice immunized with constructs expressing human SDF1β, which binds to murine CXCR4. Therefore, these data demonstrate that fusion constructs with defensins, which target immature DC, can render a non-immunogenic tumor antigen (sFv) immunogenic and elicit protective antitumor immunity, even for a very aggressive lymphoma, 38C13, which kills all control mice within 20 days post challenge.

Next, the fusion constructs were used to demonstrate treatment of an established tumor. The A20 model (Kim, K. J., Kanellopoulos, Langevin C., Merwin, R. M., Sachs, D. H., and Asofsky, R. 1979. Establishment and characterization of BALB/c lymphoma lines with B cell properties. *J. Immunol.* 122(2): 549), which is relatively slower growing, was used to demonstrate the therapeutic potency of the approach. The therapeutic efficacy of the DNA constructs was assessed. Ten mice per group tumor bearing mice immunized with 2 mg DNA vaccine expressing β-defensin 2 and 3 fusions with sFv20 (pmMIP3α sFv20, pmDF2β sFv20 and pmDF3β sFv20) starting one day after challenge with a lethal dose of A20 tumor, followed by three booster vaccinations. No survivors were observed in tumor bearing mice randomized to control treatment with the same β-defensin, but fused with sFv derived from the 38C-13 lymphoma (pmDF2β sFv38), suggesting that non-specific effects of β-defensins were not sufficient for tumor eradication. In contrast, a significant number of surviving mice was observed in the pmDF2β sFv20 treatment group (logrank P<0.002 compared with pmDF2β sFv38). It is notable that in this model, although the β-defensin 3 fusion vaccine also induced a superior specific antibody production, the vaccine was not able to elicit antitumor immunity. A superior antibody production also was generated by vaccinating with A20 lymphoma derived Ig-KLH protein (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253), though it was not sufficient to elicit both protective (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253) and therapeutic immunity in A20 model. Thus, these data suggest that induction of humoral immunity is not sufficient to eradicate A20 B cell lymphoma, and that fusions with inflammatory chemokines MCP-3 and MIP3α or β-defensin 2 induced specific cellular antitumor responses.

Requirement for chemokine receptor targeting with fusion constructs. Next it was demonstrated that β-defensin should be physically linked with sFv by immunizing with mixture of unlinked β-defensin and sFv. Ten mice per group immunized with a mixture of separate plasmids encoding β-defensin 3 (pmDF3β Muc1T) and sFv antigen (sFv38) failed to elicit a specific humoral response, thus, demonstrating a requirement for sFv to be physically linked to b-defensin. Furthermore, these mice challenged with lethal dose of syngeneic 38C13 tumor exhibited no protection. These data also suggest that chemokine receptor engagement with chemokine- or defensin-sFv fusion is essential for the induction of immunity, and it was not sufficient to simply attract APC, or induce inflammation at the site of production of sFv antigen, but that direct APC targeting with antigen fused to β-defensin or chemokine was required, presumably via the involvement of chemotactic receptors. To further demonstrate this, receptor-mediated immunity was inhibited by injection of the competing ligand. Ten per group C3H mice were immunized with either pmDF3α sFv38 alone or mixed with DNA encoding β-defensin fused with irrelevant antigen (pmDF3β Muc1T). Sera of mice immunized with a plasmid encoding sFv protein fused with murine β-defensin 3 by itself or in presence of an irrelevant plasmid contained about 300 mg/ml idiotype-specific antibodies on average, which was two-three fold higher than the levels induced by vaccination with tumor-derived intact Ig protein conjugated to KLH. However, much lower levels (5-15 mg/ml) of specific antibodies were detected in sera of mice co-immunized with pmDF3β sFv38 mixed competing pmDF3β Muc1T. Two weeks after the last immunization, all mice were challenged with 20-fold lethal dose of syngeneic 38C13 tumor. No survival was observed in control groups immunized with PBS or plasmid encoding β-defensin 3 fused with an irrelevant antigen (pmDF3β Muc1T). Similarly, no protection was detected in mice co-immunized with pmDF3β sFv38 and competing pmDF3β Muc1T (pmDF3β Muc1T/pmDF3β sFv38). In contrast, 40% of mice immunized with pmDF3β sFv38 were protected (Logrank P<0.001 compared with pmDF3β Muc1T). Therefore, these data support the view that immunity to non-immunogenic tumor antigens fused with defensins or chemokines depended on their ability to engage chemokine receptor(s).

Discussion

This example demonstrates that a non-immunogenic tumor antigen, lymphoma idiotype (Stevenson, F. K., Zhu, D., King, C. A., Ashworth, L. J., Kumar, S., and Hawkins, R. E. 1995. Idiotypic DNA vaccines against B-cell lymphoma. *Immunol. Rev.* 145: 211), is rendered immunogenic when genetically fused with defensins. This immunity is correlated with the ability of murine β-defensin 2 and 3 to induce chemotaxis of murine bone marrow derived immature, but not mature DC. Human β-defensin-2 binds to CCR6 preferentially expressed on iDC and resting memory T cells (Dieu, M. C., Vanbervliet, B., Vicari, A., Bridon, J. M., Oldham, E., Ait-Yahia, S., Briere, F., Zlotnik, A., Lebecque, S., and Caux, C. 1998. Selective recruitment of immature and mature dendritic cells by distinct chemokines expressed in different anatomic sites. *J. Exp. Med.* 188(2): 373; Yang, D., Howard, O. M., Chen, Q., and Oppenheim, J. J. 1999. Cutting edge: immature dendritic cells generated from monocytes in the presence of TGF-beta 1 express functional C-C chemokine receptor 6. *J. Immunol* 163(4): 1737).

Example 4

Methods

Fusion gene cloning and plasmid constructions. gp120 gene was cloned from the plasmid DNA containing portion of HIV-1 (isolate 89.6) in frame with IP-10 secretion signal sequence (pgp120) using primers PRM89.6ENV-5' (AAAGTCGACAAAGAAAAAACGTGGGTCACAATCT; SEQ ID NO:26) and PR89.6ENV-3' (ATTCCCGGGTTATTTTCTCTTTGCACTGTTCTTCTC; SEQ ID NO:27). Cloning strategy for lymphoma for chemokine genes has been reported elsewhere (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). Briefly, genes for mature human and murine chemokines, such as MCP-3 and IP-10, and defensins were cloned in frame to the 5'-end of gp120 by RT/PCR from total RNA using specific primers as described previously (Biragyn, A., Tani, K., Grimm, M. C., Weeks, S. D., and Kwak, L. W. 1999. Genetic fusion of chemokines to a self tumor antigen induces protective, T-cell dependent antitumor immunity. *Nature Biotechnology* 17: 253). For example: genes for human MDC (GeneBank #HSU83171) was cloned from LPS 10 ng/ml treated human monocytes using respectively pairs of primers PRhMDC-5' (CTCTAGACACCATG-GCTCGCCTACAGACTGCACT; SEQ ID NO:28) and PRhMDC-3' (TGAATTCTTGGCTCAGCTTAT-TGAGAATCA; SEQ ID NO:29); Murine β-defensin 2 (GeneBank #AJ011800) and β-defensin 3 (GeneBank #AF092929) genes were cloned from LPS (10 ng) Balb/c mouse skin using pairs of primers, respectively PRmDF2β-5' (ACCATGGAACTTGACCACTGCCACACC; SEQ ID NO:30) and PRmDF2β-3' (TGAATTCAAGATCTTTCATG-TACTTGCAACAGGGGTTGTT; SEQ ID NO:31) and PRmDF3β-5' (ACCATGGAAAAAATCAACAATCAG-TAAGTTGTTTGAGG; SEQ ID NO:32) and PRmDF3β-3' (CTCGAGCTAGAATTCTTTTCTCTTGCAG-CATTTGAGGAAA; SEQ ID NO:33). Similarly, murine β-pro-defensin 2 gene was cloned for eukaryotic expression using PrproDF2β L-5' (AAAGCTTCCACCATGAG-GACTCTCTGCTCT; SEQ ID NO:34) and PRmDF2β-3', which contained native secretion signal sequence. gp120 was fused in frame with coding sequences from murine β-defensin 2 or 3, hMDC and hMCP3 to generate DNA constructs pmDF2β gp120, pmDF3β gp120, phMDCgp120 and phMCP3gp120, respectively. Chemokine and defensins have been fused with gp120 through a spacer sequence NDAQAPKS (SEQ ID NO:35). To generate constructs encoding mutant chemokines, the first Cys residue was replaced to Ser for all chemokines, except for hMCP-3 and hMDC where the amino-terminus up to the second Cys residue were truncated. All constructs were verified by DNA dideoxy-sequencing method, using T7 sequenase kit (Amersham, USA) and purified using Qiagen plasmid purification kit (Qiagen, Valencia, Calif.).

In vitro chemotaxis assay: The chemotactic migration of murine dendritic cells was assessed using a 48-well microchemotaxis chamber technique as previously described (Falk, W., Goodwin, R. H. Jr, and Leonard, E. J. 1980. A 48-well micro chemotaxis assembly for rapid and accurate measurement of leukocyte migration. *J. Immunol Methods* 33(3): 239; Yang, D., Chen, Q., Stoll, S., Chen, X., Howard, 0. M., and Oppenheim, J. J. 2000. Differential regulation of responsiveness to fMLP and C5a upon dendritic cell maturation: correlation with receptor expression. *J. Immunol.* 165(5):2694). Briefly, different concentrations of 26 ml chemotactic factors or aliquots of sFv fusion protein, serially diluted in chemotaxis medium (RPMI 1640, 1% BSA, 25 mM HEPES), were placed in the lower compartment of the chamber (Neuro Probe, Cabin John, Mass.), and 50 ml of dendritic cells ($10^6$ cells/ml) were added to wells of the upper compartment. The lower and upper compartments were separated by a 5-mm polycarbonate filter (Osmonics, Livermore, Calif.). After incubation at 37° C. in humidified air with 5% $CO_2$ for 1.5 h, the filters were removed, scraped, and stained. Dendritic cells migrating across the filter were counted with the use of a Bioquant semiautomatic counting system. The results are presented as chemotactic index (C. I.) defined as the fold increase in the number of migrating cells in the presence of test factors over the spontaneous cell migration (in the absence of test factors). The results are expressed as the mean±SE of triplicate samples. MIP-3α and MIP-3β were purchased from PeproTech (Rocky Hill, N.J.).

HIV-1 env antibody and CTL assays. Five BALB/c female mice per group were immunized with DNA plasmids four times using gene-gun. Two weeks after the last immunization, HIV-1 89.6 env specific CTL was assessed in spleens and Peyer's patches as described elsewhere (Belyakov, I. M., Derby, M. A., Ahlers, J. D., Kelsall, B. L., Earl, P., Moss, B., Strober, W., and Berzofsky, J. A. 1998. Mucosal immunization with HIV-1 peptide vaccine induces mucosal and systemic cytotoxic T lymphocytes and protective immunity in mice against intrarectal recombinant HIV-vaccinia challenge. *Proc. Natl. Acad. Sci. U.S.A* 95(4): 1709). Briefly, immune cells from spleen or Peyer's patch were cultured at $5 \times 10^6$ per/milliliter in 24-well culture plates in complete T cell medium (CTM): RPMI 1640 containing 10% fetal bovine serum, 2 mM L-glutamine, penicillin (100 U/ml), streptomycin (100 mg/ml), and $5 \times 10^{-5}$M 2-mercaptoethanol. Three days later 10% concanavalin A supernatant was added as a source of IL-2 (T-STIM, Collaborative Biomedical Products, Bedford, Mass.). Spleen or Peyer's patch cells were stimulated in vitro with P18-89.6A9 peptide (IGPGRAFYA; SEQ ID NO:36) (Belyakov, I. M., Wyatt, L. S., Ahlers, J. D., Earl, P., Pendleton, C. D., Kelsall, B. L., Strober, W., Moss, B., and Berzofsky, J. A. 1998. Induction of a mucosal cytotoxic T-lymphocyte response by intrarectal immunization with a replication-deficient recombinant vaccinia virus expressing human immunodeficiency virus 89.6 envelope protein. *J. Virol.* 72(10): 8264) for a 7-day culture periods before assay. Cytolytic activity of CTL lines was measured by a 4-hour assay with $^{51}$Cr-labeled P815 cell targets. For testing the peptide specificity of CTL, $^{51}$Cr-labeled P815 targets were pulsed for 2 hours with peptide at the beginning of the assay or left unpulsed as controls. The percent specific $^{51}$Cr release was calculated as 100×(experimental release−spontaneous release)/(maximum release−spontaneous release). Maximum release was determined from supernatants of cells that were lysed by addition of 5% Triton-X 100. Spontaneous release was determined from target cells incubated without added effector cells (Belyakov, I. M., Derby, M. A., Ahlers, J. D., Kelsall, B. L., Earl, P., Moss, B., Strober, W., and Berzofsky, J. A. 1998. Mucosal immunization with HIV-1 peptide vaccine induces mucosal and systemic cytotoxic T lymphocytes and protective immunity in mice against intrarectal recombinant HIV-vaccinia challenge. *Proc. Natl. Acad. Sci. U.S.A* 95(4): 1709).

Serum anti-env antibodies assessed by ELISA on 5 mg/ml gp120 protein from isolate 89.6 produced in vaccinia virus coated 96-well plate. The bound antibodies were detected by goat anti-mouse Ig-HRP mAb (Caltag) and developed with ABTS peroxidase substrate (KPL, Gaithersburg, Md.).

In vivo immunizations. Animal care was provided in accordance with the procedures outlined in a Guide for the Care and Use of Laboratory Animals (NIH Publication No. 86-23, 1985). Six- to nine-week old female BALB/c mice (Charles River Laboratories, Frederick, Md.) were immunized with Helios Gene Gun System (Bio-Rad, Hercules, Calif.) with plasmid DNA four times every two weeks. The abdominal area of mice was shaved, and 1 m gold particles (Bio-Rad, Hercules, Calif.) carrying 1-3 mg DNA were injected at 400 psi.

Results and Discussion.

Mammalian expression plasmid vectors were constructed by cloning gp120 alone (pgp120), or as fusion constructs of gp120 with β-Defensin 2 or 3, human MDC or MCP-3 (pmDF2β gp120, pmDF3β gp120, pMDCgp120 and pMCP3gp120, respectively, Table 2). All constructs expressed equivalent amounts of gp120 when transfected transiently in 293 cells. Purified fusion proteins with proinflammatory chemokines or murine β-defensins generally retained chemokine functional integrity, such as chemo-attraction of murine bone-marrow derived immature, but not mature DC (see Example 3).

TABLE 2

Ligand-Antigen fusion constructs

| DNA vaccine name | Ligand: Defensin or chemokine | Antigen | Description |
|---|---|---|---|
| Antigen alone | | | |
| pgp120 | none | gp120 | HIV-1 gp120, 89.6. |
| Defensin fusion: | | | |
| pmDF2βgp120 | murine β-defensin 2 | gp120 | Murine β-defensin 2 fusion with gp120 |
| Chemokine fusions: | | | |
| pMCP3gp120 | hMCP-3 | gp120 | human MCP-3 fusion with gp120 |
| pMDCgp120 | hMDC | gp120 | human MDC fusion with gp120 |

BALB/c mice were immunized four times biweekly using a gene gun with DNA plasmids encoding gp120 alone, or fusion constructs of gp120 with β-Defensin 2 or 3, human MDC or MCP-3 (pgp120, pmDF2β gp120, pmDF3β gp120, pMDCgp120 and pMCP3gp120, respectively). Two weeks after the last immunization, sera from these mice were tested for α-gp120 antibodies using recombinant gp120 produced in Vaccinia. As expected, control mice immunized with DNA encoding gp120 alone did not induce any anti-gp120 antibody (Putkonen, P., Quesada-Rolander, M., Leandersson, A. C., Schwartz, S., Thorstensson, R., Okuda, K., Wahren, B., and Hinkula, J. 1998. Immune responses but no protection against SHIV by gene-gun delivery of HIV-1 DNA followed by recombinant subunit protein boosts. *Virology* 250(2): 293). In contrast, mice immunized with pmDF2β gp120, pmDF3β gp120, phMDCgp120 and phMCP3gp120 fusions all produced high titers of env-specific antibodies. These data suggest that the inability of gp120 to elicit humoral immunity was circumvented by fusion to either proinflammatory chemokines or β-defensins.

These DNA fusions were used to induce anti-gp120 cellular responses. Spleen cells from mice immunized with β-Defensin 2 or MCP-3 fusion constructs demonstrated significant lysis of P815 target cells pulsed with HIV-1 89.6 A9 peptide (pmDF2β gp120 and phMCP3g120, respectively, pulsed (*) vs. unpulsed targets). In contrast, no CTL were detected in mice immunized with pgp120 alone or PBS. These data thus demonstrate that immunizations with DNA plasmids encoding gp120 fused with proinflammatory chemokines or β-defensins induced significant gp120 V3-loop specific systemic CTL. Mice immunized with DNA encoding gp120 fused with MCP3- or β-defensin 2 elicited significant CTL activity in Peyer's patches, suggesting that these vaccines also induced mucosal immunity. This data indicate that DNA immunizations in the skin can induce mucosal immunity in addition to systemic immunity, a feature that had not been demonstrated prior to the disclosed compositions.

In addition to targeting gp120 to professional APC, expressed fusion proteins may induce expression of co-stimulatory molecules and production of pro-inflammatory cytokines by various subsets of immature DC in vivo. Moreover, Th1 or Th2 cells could be differentially attracted by chemokines, thus modulating immunity. For example, MCP-1 stimulates IL-4 production (Karpus, W. J., N. W. Lukacs, K. J. Kennedy, W. S. Smith, S. D. Hurst, and T. A. Barrett. 1997. Differential CC chemokine-induced enhancement of T helper cell cytokine production. *J. Immunol* 158: 4129) and thereby induces control Th2 polarization (Gu, L., S. Tseng, R. M. Horner, C. Tam, M. Loda, and B. J. Rollins. 2000. Control of TH2 polarization by the chemokine monocyte chemoattractant protein-1. *Nature* 404:407). Moreover, MDC has been reported to selectively chemo-attract Th2 cells towards APC (Imai, T., M. Nagira, S. Takagi, M. Kakizaki, M. Nishimura, J. Wang, P. W. Gray, K. Matsushima, and O. Yoshie. 1999. Selective recruitment of CCR4-bearing Th2 cells toward antigen-presenting cells by the CC chemokines thymus and activation-regulated chemokine and macrophage-derived chemokine. *Int. Immunol* 11:81). Comparison of MDC fusion vaccines to fusions with MCP-3, which binds multiple receptors, such as CCR1-4 expressed on variety of APC, demonstrated that each vaccine construct induced α-gp120 antibody production. However, the highest yield was observed in sera of mice immunized with MDC fusions, which unlike to the MCP-3 or β-defensin 2 fusion constructs, failed to induce α-gp120 CTL. In concordance, non-immunogenic tumor antigens fused with MDC did not induce therapeutic antitumor immunity in murine tumor models, despite production of high levels of specific antibody. In contrast, tumor antigen fusion constructs with both MCP-3 and β-defensin 2 induced moderate antibody production and significant therapeutic antitumor immunity (see Example 3). Therefore, these data show that preferential immunity may be elicited by differential use of chemokines or defensin. Thus, the disclosed compositions and methods represent a very efficient and simple approach to generate systemic and mucosal immunity. These results also stand in contrast to the widely accepted view that DNA vaccinations alone cannot induce anti-gp120 HIV-1 responses without additional protein or recombinant viral vaccine boosts (Hanke, T., Samuel, R. V., Blanchard, T. J., Neumann, V. C., Allen, T. M., Boyson, J. E., Sharpe, S. A., Cook, N., Smith, G. L., Watkins, D. I., Cranage, M. P., and McMichael, A. J. 1999. Effective induction of simian immunodeficiency virus-specific cytotoxic T lymphocytes in macaques by using a multiepitope gene and DNA prime-modified vaccinia virus Ankara boost vaccination regimen. *J. Virol.* 73(9): 7524; Putkonen, P., Quesada-Rolander, M., Leandersson, A. C., Schwartz, S., Thorstensson, R., Okuda, K., Wahren, B., and Hinkula, J. 1998. Immune responses but no protection against SHIV by gene-gun delivery of HIV-1 DNA followed by recombinant subunit protein boosts. *Virology* 250(2): 293).

Example 5

This example demonstrates that antigens elicit effective immunity when they are targeted to APC, particularly iDC, via chemokine receptors as fusions with proinflammatory chemokines factors. Moreover, this example demonstrates that proinflammatory factors such as murine β-defensins induce chemotaxis of immature, but not mature, DC and, thus, can serve effectively as an carrier for targeting antigens to APC. Non-immunogenic tumor antigens or xenogeneic HIV gp120 antigen were rendered effectively immunogenic when immunized as fusion with murine β-defensin 2. This example also demonstrates the use of xenogeneic human and viral chemokines such as Kaposi's sarcoma virus derived chemokine analogues of human MIP-1s, designated vMIP1 and vMIP2 (Nicholas, J., V. R. Ruvolo, W. H. Burns, G. Sandford, X. Wan, D. Ciufo, S. B. Hendrickson, H. G. Guo, G. S. Hayward, and M. S. Reitz. 1997. Kaposi's sarcoma-associated human herpesvirus-8 encodes homologues of macrophage inflammatory protein-1 and interleukin-6. *Nat. Med.* 3:(3)287-292), which bind multiple receptors on murine cells and which might circumvent the potential development of autoimmunity against host chemokine carriers (Luster, A. D. 1998. Chemokines—chemotactic cytokines that mediate inflammation. *N. Engl. J. Med.* 338:(7)436-445; Pelchen-Matthews, A., N. Signoret, P. J. Klasse, A. Fraile-Ramos, and M. Marsh. 1999. Chemokine receptor trafficking and viral replication. *Immunol Rev.* 168:33-49:33-49). In addition, using a pair of viral chemokines that bind to CCR8, the agonist vMIP1 (Endres, M. J., C. G. Garlisi, H. Xiao, L. Shan, and J. A. Hedrick. 1999. The Kaposi's sarcoma-related herpesvirus (KSHV)-encoded chemokine vMIP-I is a specific agonist for the CC chemokine receptor (CCR)8. *J. Exp. Med.* 189:(12)1993-1998) and antagonist MC148, expressed by Molluscum contagiosum virus (MCV) (Luttichau, H. R., J. Stine, T. P. Boesen, A. H. Johnsen, D. Chantry, J. Gerstoft, and T. W. Schwartz. 2000. A highly selective CC chemokine receptor (CCR)8 antagonist encoded by the poxvirus molluscum contagiosum *J. Exp. Med.* 191:(1)171-180), we demonstrate that antigen targeting alone in the absence of chemotaxis is sufficient for induction of immunity.

Methods

Fusion gene cloning and plasmid constructions. Cloning strategy for lymphoma specific $V_H$ and $V_L$ fragments from 38C13 (Bergmanm Y. and J. Haimovich. 1977. Characterization of a carcinogen-induced murine B lymphocyte cell line of C3H/eb origin. *J. Immunol.* 7:413-417) and A20 (Kim, K. J., L. C. Kanellopoulos, R. M. Merwin, D. H. Sachs, and R. Asofsky. 1979. Establishment and characterization of BALB/c lymphoma lines with B cell properties. *J. Immunol.* 122:(2)549-554) cells as sFv38 and sFv20, respectively, has been reported elsewhere (Biragyn, A., K. Tani, M. C. Grimm, S. D. Weeks, and L. W. Kwak. 1999. Genetic fusion of chemokines to a self tumor antigen induces protective, T-cell dependent antitumor immunity. *Nature Biotechnology* 17:253-258). Genes for mature human and murine chemokines and defensins were cloned in frame to the 5'-end of sFv by RT/PCR from total RNA using specific primers as described previously (Biragyn, A., K. Tani, M. C. Grimm, S. D. Weeks, and L. W. Kwak. 1999. Genetic fusion of chemokines to a self tumor antigen induces protective, T-cell dependent antitumor immunity. *Nature Biotechnology* 17:253-258). For example: genes for human MDC (GeneBank #HSU83171) and SDF-1β (GeneBank #HSU16752) were cloned from LPS 10 ng/ml treated human monocytes using respectively pairs of primers PRhMDC-5' (CTCTAGACACCATGGCTCGCCTACAGACTGCACT; SEQ ID NO:37) and PRhMDC-3' (TGAATTCTTGGCT-CAGCTTATTGAGAATCA; SEQ ID NO:38); and PRhSDF1β-5' (CTCTAGACACCATGAACGCCAAG-GTCGTGGTCGTGCTG; SEQ ID NO:39) and PRhSDF1β-3' (TGAATTCCATCTTGAACCTCTTGTTTAAAGCTTT; SEQ ID NO:40). Murine β-defensin 2 (GeneBank #AJ011800) and β-defensin 3 (GeneBank #AF092929) genes were cloned from LPS (10 ng) Balb/c mouse skin using pairs of primers, respectively PRmDF2β-5' (ACCATGGAACT-TGACCACTGCCACACC; SEQ ID NO:41) and PRmDF2β-3' (TGAATTCAAGATCTTTCATGTACTTGCAACA GGG GTTGTT; SEQ ID NO:42) and PRmDF3β-5' (ACCATG-GAAAAAATCAACAATCAGTAAGTTGTTTGAGG; SEQ ID NO:43) and PRmDF3β-3' (CTCGAGCTAGAAT-TCTTTTCTCTTGCAGCATTTGAGGAAA; SEQ ID NO:44). Similarly, murine β-pro-defensin 2 gene was cloned for eukaryotic expression using PrproDF2βL-5' (AAAGCT-TCCACCATGAGGACTCTCTGCTCT; SEQ ID NO:45)

and PRmDF2β-3', which contained native secretion signal sequence. For bacterial expression, the signal sequence was removed using PRmDF2β-5' (ACCATGGCTGTTG-GAAGTTTAAAAAGTATTGGA; SEQ ID NO:46) and PRmDF2β-3'. Viral chemokine genes vMIP-I (GeneBank #KSU74585) and vMIP-II (GeneBank #KSU67775) were cloned from BCBL-1 lymphoma cell line infected with HHV-8 (NIH AIDS Research & Ref. Reag. Program), using pairs of primers, respectively PRvMIP1L-5' (TAAGCTTC-CACCATGGCCCCCGTCCACGTTTTATGCT; SEQ ID NO:47) and PRvMIP1-3' (TGAATTCAGCTATGGCAG-GCAGCCGCTGCATCAGCTGCCT; SEQ ID NO:48) and PRvMIP1IL-5' (TAAGCTTCACCATGGACAC-CAAGGGCATCCTGCTCGT; SEQ ID NO:49) and PRvMIP1I-3' (TGAATTCGCGAGCAGTGACTGGTAAT-TGCTGCAT; SEQ ID NO:50). Mature sequences of vMIP-I and vMIP-II for expression in bacterial system were cloned using the following pairs of primers: PRvMIP1M-5' (AC-CATGGCGGGGTCACTCGTGTCGTACA; SEQ ID NO:51) and PRO/BPI-3' and PRvMIP2M-5' (ACCATGG-GAGCGTCCTGGCATAGA; SEQ ID NO:52) and PRvMIP1I-3'. MC148 chemokine gene (GeneBank #U96749) was cloned from plasmid DNA containing a portion of Moluscum contagiosum virus type 1 genome (Damon, I., P. M. Murphy, and B. Moss. 1998. Broad spectrum chemokine antagonistic activity of a human poxvirus chemokine homolog. *Proc. Natl. Acad. Sci. U.S.A* 95:(11) 6403-6407) using pairs of primers PRMC148L-5' (AAAGCTAGCACCATGAGGGGCGGAGACGTCTTC; SEQ ID NO:53) and PRMC148-3' (AGAATTCCA-GAGACTCGCACCCGGACCATAT; SEQ ID NO:54) and PRMC148M-5' (ACCATGGCACTCGCGAGACGGAAAT-GTTGTTTGAAT; SEQ ID NO:55) and PRMC148-3', respectively for eukaryotic and bacterial expression. The carboxy-terminus of sFv was fused in frame with a tag sequence coding c-myc peptide AEEQKLISEEDLA (SEQ ID NO:56) and six His, respectively. Chemokine and defensins have been fused with sFv through a spacer sequence NDAQAPKS (SEQ ID NO:57). To generate constructs encoding mutant chemokines, the first Cys residue was replaced to Ser for all chemokines, except for hMCP-3 and hMDC where the amino-terminus up to the second Cys residue were truncated. Bacterial expression vectors contained only genes encoding mature peptide genes, while constructs for DNA vaccination were fused in frame to a leader sequence of IP-10 in pCMVE/AB, except for constructs designed for pMDCsFv38 and pSDF1βsFv38 plasmids, which contained their native signal sequences. All constructs were verified by DNA dideoxy-sequencing method, using T7 sequenase kit (Amersham, USA) and purified using Qiagen plasmid purification kit (Qiagen, Valencia, Calif.).

For the second model, gp120 gene was cloned from the plasmid DNA containing portion of HIV-1 (isolate 89.6) in frame with IP-10 secretion signal sequence (pgp120) using primers PRM89.6ENV-5' (AAAGTCGACAAA-GAAAAAACGTGG GTCACAATCT; SEQ ID NO:58) and PR89.6ENV-3' (ATTCCCGGGTTATTTTTCTCTTTG-CACTGTTCTTCTC; SEQ ID NO:59). Similarly, gp120 was fused in frame with coding sequences from murine β-defensin 2, hMDC and hMCP3 to generate DNA constructs pmDF2βgp120, phMDCgp120, phMCP3gp120, respectively.

Recombinant fusion proteins purified as inclusion bodies after 8 hours of induction in Super-Broth (Digene Diagnostics, Inc., Beltsville, Md.) with 0.8 mM IPTG in the presence of 150 μg/ml carbenicillin and 50 μg/ml ampicillin at 30° C., and refolded according to Buchner, et al (Buchner, J., I. Pastan, and U. Brinkmann. 1992. A method for increasing the yield of properly folded recombinant fusion proteins: single-chain immunotoxins from renaturation of bacterial inclusion bodies. *Anal. Biochem.* 205:(2)263-270) with modifications (Biragyn, A., K. Tani, M. C. Grimm, S. D. Weeks, and L. W. Kwak. 1999. Genetic fusion of chemokines to a self tumor antigen induces protective, T-cell dependent antitumor immunity. *Nature Biotechnology* 17:253-258) from BL21 (DE3) cells (Invitrogen, Milford, Mass.). The refolded fusion proteins were purified by heparin-sepharose chromatography (Pharmacia Biotech, Uppsala, Sweden). The integrity and purity of recombinant proteins were tested by PAGE under reducing conditions and by western blot hybridization with 9E10 anti-c-myc mAb (Sigma). Purification usually yielded soluble protein with greater than 90% purity. Correct folding of purified sFv38 proteins were determined by the ability to bind to anti-idiotype mAb S1C5 by ELISA (Biragyn, A., K. Tani, M. C. Grimm, S. D. Weeks, and L. W. Kwak. 1999. Genetic fusion of chemokines to a self tumor antigen induces protective, T-cell dependent antitumor immunity. *Nature Biotechnology* 17:253-258). Briefly, serially diluted sFv were added to microtiter plates coated with 10 μg/ml anti-c-myc mAb 9E10. After washing, plates were incubated with a 1:300 diluting of biotinylated S1C5. Plates were washed, incubated with streptavidin-HRP (1:5000, Jackson Immuno research Lab., Inc., Bar harbor, ME) and developed with ABTS peroxidase substrate (KPL, Gaithersburg, Md.).

Isolation of murine bone marrow derived dendritic cells. Murine bone marrow derived DC were isolated as described elsewhere (Fields, R. C., J. J. Osterholzer, J. A. Fuller, E. K. Thomas, P. J. Geraghty, and J. J. Mule. 1998. Comparative analysis of murine dendritic cells derived from spleen and bone marrow. *J. Immunother.* 21:(5)323-339). Briefly, bone marrow was collected from tibias and femurs of 4 to 6 months old BALB/c mice by flushing with PBS using a 10 mL syringe with a 27 gauge needle. Erytrocytes were lysed by treatment with ACK lysis buffer (BioWhittaker, Walkersville, Md.). Cells expressing CD8, CD4, B220 and I-A$^b$ were depleted using a mixture of mAbs and rabbit complement. The mAbs were TIB-146 (anti-B220), TIB-150 (anti-CD8), TIB-207 (anti-CD4), TIB-229 (anti-I-A$^b$) obtained from ATCC. Cells were then resuspended with DC medium (RPMI 1640 containing 5% heat inactivated fetal bovine serum, 1% penicillin streptomycin, 1% L-glutamine and 5×10$^{-5}$2-ME) supplemented with 10 ng/mL recombinant murine IL-4 and 10 ng/mL recombinant murine GM-CSF (Peprotech) and cultured in 6 well plates (7×10$^5$ cells/mL, 5 mL/well). On day two, 200 μl DC medium containing 10 ng/mL of both IL-4 and GM-CSF were added to each well. Then, at day four, 5 μl of DC medium containing cytokines were added to each well after non-adherent cells were removed, and cells were cultured for additional 4 days. Cells were harvested on day 4 and day 7 and used in subsequent experiments.

In vitro chemotaxis assay: The chemotactic migration of murine dendritic cells was assessed using a 48-well microchemotaxis chamber technique as previously described (Falk, W., R. H. J. Goodwin, and E. J. Leonard. 1980. A 48-well micro chemotaxis assembly for rapid and accurate measurement of leukocyte migration. *J. Immunol Methods* 33:(3)239-247; Yang, D., Q. Chen, S. Stoll, X. Chen, O. M. Howard, and J. J. Oppenheim. 2000. Differential regulation of responsiveness to fMLP and C5a upon dendritic cell maturation: correlation with receptor expression. *J. Immunol.* 165:(5)2694-2702). Briefly, different concentrations of 26 ml chemotactic factors or aliquots of sFv fusion protein, serially diluted in chemotaxis medium (RPMI 1640, 1% BSA, 25 mM HEPES), were placed in the lower compartment of the chamber (Neuro Probe, Cabin John, Mass.), and 50 µl of dendritic cells ($10^6$ cells/ml) were added to wells of the upper compartment. The lower and upper compartments were separated by a 5-µm polycarbonate filter (Osmonics, Livermore, Calif.). After incubation at 37° C. in humidified air with 5% $CO_2$ for 1.5 h, the filters were removed, scraped, and stained. Dendritic cells migrating across the filter were counted with the use of a Bioquant semiautomatic counting system. The results are presented as chemotactic index (C. I.) defined as the fold increase in the number of migrating cells in the presence of test factors over the spontaneous cell migration (in the absence of test factors). The results are expressed as the mean±SE of triplicate samples. MIP-3α and MIP-3β were purchased from PeproTech (Rocky Hill, N.J.).

Chemokine receptor binding assay. Binding assays were performed by using a single concentration of radio-labeled MIP-1β or SDF-1α (human $[^{125}\text{-I}]$-$[\text{Leu}^3, \text{Gly}^{47}]$-MIP-1β and human $[^{125}\text{I}]$-SDF-1α, 2200 Ci/mmol, NEN Life Science Products Inc., Boston, Mass.) in the presence of increasing concentrations of unlabeled ligands (MIP-1β and SDF-1α obtained from PeproTech, Rocky Hill, N.J.). Human HEK293 cells transfected with CCR5 at $1\times10^6$/sample were suspended in 200 µl binding medium composed of RPMI1640, 1 mg/ml BSA, 25 mM HEPES, and 0.05% sodium azide, and incubated in duplicates at room temperature for 40 min. After incubation, the cells were pelleted through a 10% sucrose/PBS cushion and the radioactivity associated with cell pellets was determined in a γ-counter (Clinigamma-Pharmacia, Gaithersburg, Md.). The binding data were then analyzed with a Macintosh computer program LIGAND (P. Munson, Division of Computer Research and Technology, NIH, Bethesda, Md.). The degree of competition for binding by unlabeled chemokines was calculated as follows: % competition for binding=1−(cpm obtained in the presence of unlabeled ligand/cpm obtained in the absence of unlabeled ligand)×100%.

HIV-I env antibody and CTL assays. Five BALB/c female mice per group were gene-gun immunized with DNA plasmids four times using gene-gun. Two weeks after the last immunization, HIV-1 89.6 env specific CTL was assessed in spleens and Peyer's patches as described elsewhere (Belyakov, I. M., M. A. Derby, J. D. Ahlers, B. L. Kelsall, P. Earl, B. Moss, W. Strober, and J. A. Berzofsky. 1998. Mucosal immunization with HIV-1 peptide vaccine induces mucosal and systemic cytotoxic T lymphocytes and protective immunity in mice against intrarectal recombinant HIV-vaccinia challenge. *Proc. Natl. Acad. Sci. U.S.A* 95:(4)1709-1714). Briefly, immune cells from spleen or Peyer's patch were cultured at $5\times10^6$ per/milliliter in 24-well culture plates in complete T cell medium (CTM): RPMI 1640 containing 10% fetal bovine serum, 2 mM L-glutamine, penicillin (100 U/ml), streptomycin (100 mg/ml), and $5\times10^{-5}$ M 2-mercaptoethanol. Three days later 10% concanavalin A supernatant was added as a source of IL-2 (T-STIM, Collaborative Biomedical Products, Bedford, Mass.). Spleen or Peyer's patch cells were stimulated in vitro with P18-89.6A9 peptide (IGPGRAFYA; SEQ ID NO:60) (Belyakov, I. M., L. S. Wyatt, J. D. Ahlers, P. Earl, C. D. Pendleton, B. L. Kelsall, W. Strober, B. Moss, and J. A. Berzofsky. 1998. Induction of a mucosal cytotoxic T-lymphocyte response by intrarectal immunization with a replication-deficient recombinant vaccinia virus expressing human immunodeficiency virus 89.6 envelope protein. *J. Virol.* 72:(10)8264-8272) for a 7-day culture periods before assay. Cytolytic activity of CTL lines was measured by a 4-hour assay with $^{51}$Cr-labeled P815 cell targets. For testing the peptide specificity of CTL, $^{51}$Cr-labeled P815 targets were pulsed for 2 hours with peptide at the beginning of the assay or left unpulsed as controls. The percent specific $^{51}$Cr release was calculated as 100×(experimental release−spontaneous release)/(maximum release−spontaneous release). Maximum release was determined from supernatants of cells that were lysed by addition of 5% Triton-X 100. Spontaneous release was determined from target cells incubated without added effector cells (Belyakov, I. M., M. A. Derby, J. D. Ahlers, B. L. Kelsall, P. Earl, B. Moss, W. Strober, and J. A. Berzofsky. 1998. Mucosal immunization with HIV-1 peptide vaccine induces mucosal and systemic cytotoxic T lymphocytes and protective immunity in mice against intrarectal recombinant HIV-vaccinia challenge. *Proc. Natl. Acad. Sci. U.S.A* 95:(4)1709-1714).

Serum anti-env antibodies assessed by ELISA on 5 µg/ml gp120 protein from isolate 89.6 produced in vaccinia virus coated 96-well plate. The bound antibodies were detected by goat anti-mouse Ig-HRP mAb (Caltag) and developed with ABTS peroxidase substrate (KPL, Gaithersburg, Md.).

Tumor cell lines and mice. The carcinogen-induced, C3H 38C-13 B cell lymphoma (Bergmanm Y. and J. Haimovich. 1977. Characterization of a carcinogen-induced murine B lymphocyte cell line of C3H/eb origin. J. Immunol. 7:413-417) was obtained from R. Levy (Stanford, Calif.). The 38C-13 tumor secretes and expresses IgM (κ) on the cell surface. Inoculation of as few as $10^2$ 38C-13 tumor cells i.p. into normal syngeneic mice results in progressive tumor growth and death of the host with a median survival time of only two weeks. Mice surviving past 60 days from tumor challenge are long-term survivors. The BALB/c A20 lymphoma (Kim, K. J., L. C. Kanellopoulos, R. M. Merwin, D. H. Sachs, and R. Asofsky. 1979. Establishment and characterization of BALB/c lymphoma lines with B cell properties. *J. Immunol.* 122:(2)549-554) was obtained from the American Type Culture Collection (Rockville, Md.) and expresses IgGk. 38C-13 and A20 cells from a common frozen stock were passaged in vitro 3 days before use in RPMI 1640 supplemented with 100 U/ml of penicillin and streptomycin, $2\times10^{-5}$M 2-mercaptoethanol, and heat inactivated 10% fetal bovine serum (Gibco BRL, Gaithersburg, Md.).

In vivo immunizations and tumor protection experiment. Animal care was provided in accordance with the procedures outlined in a Guide for the Care and Use of Laboratory Animals (NIH Publication No. 86-23, 1985). Six- to nine-week old female C3H/HeNCrlBR or BALB/c mice (Charles River Laboratories, Frederick, Md.) were used. Syngeneic C3H/HeN or BalbC mice (10 per group) were immunized with Helios Gene Gun System (Bio-Rad, Hercules, Calif.) with plasmid DNA three times every two weeks. The abdominal area of mice was shaved, and 1µ gold particles (Bio-Rad, Hercules, Calif.) carrying 1-3 µg DNA were injected at 400 psi. Two weeks after the last immunization, mice were challenged i.p. with 2000 38C-13 lymphoma cells from a single preparation of tumor and followed for survival. Differences in survival between groups were determined by non-parametric logrank test (BMDP statistical software, Los Angeles). P-values refer to comparison with group immunized with DNA expressing the same chemokine or defensin fused with an irrelevant sFv, or sFv fused with mutant chemokine, unless specified.

Therapy of established tumor with DNA vaccine. Six- to nine-week old female BALB/c mice (ten per group) were challenged with $2.5\times10^5$ syngeneic A20 tumor cells. At day 1, 4, 8 and 18 these mice were gene-gun immunized with DNA plasmid (containing about 1-2 µg DNA per immunization) and mice followed for tumor progression.

Results

Property of constructs: murine β-defensins and viral chemokines retain their functional integrity when produced as fusion proteins with sFv. First, a variety of chemokine and β-defensin fusion proteins with sFv, a lymphoma Ig-derived non-immunogenic Fv, were cloned and purified (Table 3). The functional integrity of these proteins were tested by the ability to induce chemotaxis of murine APC and THP-1 cells. As expected, chemokine fusion proteins induced dose-dependent chemotaxis. THP-1 cells were chemo-attracted to vMIP1, human MCP-3, and SDF-1β fusion proteins, but not to the fusion with antagonist chemokine vMIP2, vMIP2sFv38. Control mutant fusion proteins generated for the each chemokine by replacing the first Cys residue by Ser or by truncation of the amino-termini, as expected, did not induce chemotaxis of THP-1 cells or murine DC. Furthermore, vMIP2 fusion proteins were tested for their ability to bind to their respective receptor(-s). vMIP2sFv38 could displace labeled MIP1β and SDF1α in a dose dependent manner from CCR5 and CXCR4 transfected cell lines, respectively.

In contrast, no displacement was detected by vMIP2MsFv38 fusion protein, which contained a replacement Cys/Ser mutation in vMIP2 or by control sFv protein alone.

Since human β-defensin 2 was reported to act via CCR6, murine β-defensin fusion proteins were assayed for their ability to induce chemotaxis of different subsets of murine cells. β-defensin fusion proteins induced chemotaxis of murine bone marrow derived iDC in a dose dependent manner with peak activity at 10 ng/ml and 100 ng/ml for Def2βsFv38 and Def3βsFv38, respectively. The immature phenotype of these DC (see Methods) was also supported by their ability to migrate to human MIP3α, a chemo-attractant specific for CCR6+ immature DC (Dieu, M. C., B. Vanbervliet, A. Vicari, J. M. Bridon, E. Oldham, S. Ait-Yahia, F. Briere, A. Zlotnik, S. Lebecque, and C. Caux. 1998. Selective recruitment of immature and mature dendritic cells by distinct chemokines expressed in different anatomic sites. *J. Exp. Med.* 188:(2)373-386; Yang, D., O. M. Howard, Q. Chen, and J. J. Oppenheim. 1999. Cutting edge: immature dendritic cells generated from monocytes in the presence of TGF-beta

TABLE 3

| | | | | |
|---|---|---|---|---|
| Ligand-Antigen fusion constructs | | | | |
| DNA vaccine name | Ligand: Defensin or chemokine | Antigen | Protein Name | Description |
| *Antigen alone* | | | | |
| psFv38 | none | sFv38 | sFv38 | Single chain antibody fragment from 38C-13 lymphoma |
| psFv20 | none | sFv20 | sFv20 | Single chain antibody fragment from A20 lymphoma |
| pgp120 | none | gp120 | gp120 | gp120 antigen (HIV-1, isolate 89.6) |
| *Defensin fusions:* | | | | |
| pmDF2βsFv38 | murine β-defensin 2 | sFv38 | mDF2βsFv38 | Murine β-defensin 2 fusion with sFv38 |
| pmDF2βgp120 | murine β-defensin 2 | gp120 | mDF2βgp120 | Murine β-defensin 2 fusion with gp120 (HIV-1, 89.6) |
| pmDF3βsFv38 | murine β-defensin 3 | sFv38 | mDF3βsFv38 | Murine β-defensin 3 fusion with sFv38 |
| pproDF2βsFv38 | murine pro-β-defensin 2 | sFv38 | mproDF2βsFv38 | Murine pro-β-defensin 2 fusion with sFv38 |
| *Viral chemokine Fusions:* | | | | |
| pvMIP2sFv38 | viral MIP2 | sFv38 | vMIP2sFv38 | Viral MIP2 fusion with sFv38 |
| pvMIP1sFv38 | viral MIP1 | sFv38 | vMIP1sFv38 | Viral MIP1 fusion with sFv38 |
| pMC148sFv38 | MC148 | sFv38 | MC148sFv38 | Viral MC148 fusion with sFv38 |
| *Pro-inflammatory Chemokine fusions:* | | | | |
| phMCP3sFv38 | Human MCP-3 | sFv38 | hMCP3sFv38 | Human MCP-3 fusion with sFv38 |
| phMCP3sFv20 | Human MCP-3 | sFv20 | hMCP3sFv20 | Human MCP-3 fusion with sFv20 |
| phMCP3gp120 | Human MCP-3 | gp120 | hMCP3gp120 | Human MCP-3 fusion with gp120 (HIV-1, isolate 89.6) |
| phMDCsFv38 | Human MDC | sFv38 | hMDCsFv38 | Human MDC fusion with sFv38 |
| phMDCsFv20 | Human MDC | sFv20 | hMDCsFv20 | Human MDC fusion with sFv20 |
| phMDCgp120 | Human MDC | gp120 | hMDCgp120 | Human MDC fusion with gp120 (HIV-1, isolate 89.6) |
| phSDF1βsFv38 | Human SDF-1β | sFv38 | hSDF1βsFv38 | Human SDF1-β fusion with sFv38 |
| *Mutant chemokine fusions:* | | | | |
| pvMIP2MsFv38 | Mutant vMIP2 | sFv38 | vMIP2MsFv38 | Mutant vMIP2 fusion with sFv38 |
| pvMIP1MsFv38 | Mutant vMIP1 | sFv38 | vMIP1MsFv38 | Mutant vMIP1 fusion with sFv38 |
| phMCP3MsFv38 | Mutant hMCP-3 | sFv38 | hMCP3MsFv38 | Mutant human MCP-3 fusion with sFv38 |
| phMDCMsFv38 | Mutant hMDC | sFv38 | hMDCMsFv38 | Mutant human MDC fusion with sFv38 |
| *Control fusions:* | | | | |
| pmDF3βMuc1 | β-defensin 3 | Muc-1 | mDF3βMuc1 | Murine β-defensin 3 fusion with 80 aa hMuc-1 peptide |
| phMCP3-EGFP | Human MCP-3 | EGFP | hMCP3-EGFP | Human MCP-3 fusion with EGFP protein |
| phMDC-EGFP | Human MDC | EGFP | hMDC-EGFP | Huma MDC fusion with EGFP protein |
| *Protein vaccine:* | | | | |
| Ig38-KLH | None | Ig38 | Ig38-KLH | 38C-13 lymphoma derived IgM protein cross-linked with KLH |
| Ig20-KLH | none | Ig20 | Ig20-KLH | A20 lymphoma derived IgG2a protein cross-linked with KLH |

1 express functional C-C chemokine receptor 6. *J. Immunol* 163:(4)1737-1741), and their inability to react to human MIP3β (Sallusto, F., B. Palermo, D. Lenig, M. Miettinen, S. Matikainen, I. Julkunen, R. Forster, R. Burgstahler, M. Lipp, and A. Lanzavecchia. 1999. Distinct patterns and kinetics of chemokine production regulate dendritic cell function. *Eur. J. Immunol* 29:(5)1617-1625), a chemo-attractant specific for CCR7+ mature DC. None of the defensin fusion proteins stimulated chemotaxis of mature DC, which migrated to MIP3β. Control fusion protein proDef2βsFv38 did not induce chemotaxis of any DC. Therefore, murine β-defensin 2 and 3 fusion proteins can specifically target immature DC. Furthermore, sFv fusion with β-defensin and xenogeneic human or viral chemokines does not disrupt their functional chemokine properties.

Murine β-defensin, xenogeneic proinflammatory and viral chemokine fusion constructs render non-immunogenic tumor antigen immunogenic. Next, these fusion proteins were used to induce specific immunity against non-immunogenic sFv38 when administered as a DNA vaccine in mice. Ten mice per group were immunized by gene-gun with plasmids encoding fusion proteins with mature β-defensins, pDef2βsFv38 and pDef3βsFv38, respectively, or with human or viral chemokines, pSDF1βsFv38, pMDCsFv38, pvMIP1sFv38 or pvMIP2sFv38. Control mice were immunized with DNA constructs encoding sFv fused with inactive pro-Defensin (pproDef2βsFv38), or mutated chemokines (phMCP3MsFv38, pMDCMsFv38, pMIP1MsFv38 and pvMIP2MsFv38). Mice immunized with plasmids encoding sFv fusion proteins with both murine β-defensins, murine MCP-3, human MDC or viral chemokines induced significant idiotype-specific antibodies which were comparable to the levels induced by vaccination with tumor-derived intact Ig protein conjugated to KLH. In contrast, control mice immunized with an inactive pro-β-defensin (pproDef2βsFv38) or mutant chemokine sFv fusion constructs (hpMCP3MsFv38, pMDCMsFv38 and pvMIP2MsFv38), or sFv38 alone did not produce any anti-Id antibody responses. Moreover, a mixture of separate plasmids encoding β-defensin 3 (pmDF3βMuc1T) and sFv antigen (sFv38) failed to elicit a specific humoral response, demonstrating a requirement for sFv to be physically linked to β-defensin or chemokine moiety. Therefore, non-immunogenic sFv was rendered immunogenic by fusion with mature murine β-defensins, syngeneic murine, xenogeneic human or viral chemokines. These results also suggest that it was not sufficient to simply attract APC to the site of production of sFv, but that direct APC targeting with self-antigen fused to β-defensin or chemokine was required. Thus, induction of anti-Id antibodies by sFv fusion proteins appeared to involve receptor-mediated binding and delivery of antigen to APC. Vaccination elicited anti-Id antibodies of various isotypes, suggesting activation of different effector cells by different pro-inflammatory moieties. All carriers induced specific IgG1 antibodies. However, MDC containing vaccines also elicited high titers of IgG2b and IgG3, while fusion constructs with β-defensin-3 and vMIP2 elicited high titers of IgG2b but little IgG3, and little IgG2b or IgG3, respectively.

Two weeks after the last of three serial immunizations, mice were challenged with a 20-fold lethal dose of syngeneic tumor. No survival was observed in control groups immunized with PBS or plasmids encoding sFv38 fused with inactive pro-(3-defensin-2 (pproDef2βsFv38), MDC alone (pMDC-EGFP), or with mutant constructs pMDCMsFv38, pvMIP2MsFv38, pvMIP1MsFv38. Moreover, no protection was observed in mice immunized with DNA encoding a mixture of unlinked functionally active β-defensin or chemokine with sFv. In contrast, significant protective immunity was elicited in mice immunized with pDef2βsFv38 and pDef3βsFv38 (logrank P<0.001 as compared with pproDef2βsFv38 and pMIP2MsFv38, respectively). Similarly, pMDCsFv38, pvMIP2sFv38 and pvMIP1sFv38 immunized mice demonstrated statistically significantly prolonged survival (logrank P<0.001 as compared with pMDC-EGFP and mutant pvMIP2MsFv38 and pvMIP1MsFv38, respectively). Therefore, β-defensins and xenogeneic human and viral chemokines can render a non-immunogenic self-tumor antigen (sFv) immunogenic and elicit specific antitumor immunity. These data also suggest that chemokine receptor engagement with chemokine- or defensin-sFv fusion is useful for the induction of immunity.

Requirement for secretion but not for chemotaxis for induction of immune responses. Additional constructs were used for testing in vivo. Mice were immunized with MCP-3 fusion constructs with or without a secretory leader sequence (pMCP3sFv38 and pMCP3sFv38-w/o-SL, respectively). High levels of Id-specific antibodies were detected in mice immunized with pMCP3sFv38, containing an intact secretory leader; however, no antibodies were elicited in mice immunized with pMCP3sFv38-w/o-SL. Furthermore, tumor protection was elicited only in those mice immunized with pMCP3sFv38, but not with pMCP3sFv38-w/o-SL (logrank P<0.001). In addition, no protection was detected in mice immunized with DNA expressing a secretable but mutated MCP-3 fusion protein, which could not bind the respective receptor (pMCP3MsFv38). These data are consistent with immunity being induced by APC which took up (via chemokine receptor) a functionally active chemokine fusion protein which was secreted from bystander cells, rather than by APC directly being transduced by gene gun immunization.

It was determined whether activation of receptor-mediated chemotaxis was required for eliciting immune responses, or whether receptor binding alone was sufficient. Immune responses of a selective pair of agonist (vMIP1) (Endres, M. J., C. G. Garlisi, H. Xiao, L. Shan, and J. A. Hedrick. 1999. The Kaposi's sarcoma-related herpesvirus (KSHV)-encoded chemokine vMIP-I is a specific agonist for the CC chemokine receptor (CCR)8. *J. Exp. Med.* 189:(12)1993-1998) and antagonist (MC148) (Luttichau, H. R., J. Stine, T. P. Boesen, A. H. Johnsen, D. Chantry, J. Gerstoft, and T. W. Schwartz. 2000. A highly selective CC chemokine receptor (CCR)8 antagonist encoded by the poxvirus molluscum contagiosum. *J. Exp. Med.* 191:(1)171-180) chemokines, which bind to CCR8, were compared to immune responses in mice immunized with plasmids encoding pvMIP1 and MC148 fusion proteins, respectively (pMIP1sFv38 and pMC148sFv38). Mice immunized with either of these chemokine fusion constructs produced comparable levels of specific antibodies. Moreover, significant tumor protection was detected in both groups of mice challenged with a high dose of 38C-13 cells (logrank P<0.001 for pMC148sFv38 and P<0.01 for pvMIP1sFv38, respectively, compared with control pvMIP1MsFv38). These data suggest that chemokine receptor binding alone, in the absence of subsequent signaling for chemotaxis, is sufficient to induce immunity.

Discussion

This example demonstrates that use of proinflammatory factors of innate and adaptive immunity such as β-defensins 2 and 3 and viral chemokines (Luster, A. D. 1998. Chemokines—chemotactic cytokines that mediate inflammation. *N. Engl. J. Med.* 338:(7)436-445) can help to elicit strong immune responses both against a model non-immunogenic tumor antigen, lymphoma idiotype (Stevenson, F. K., D. Zhu, C. A. King, L. J. Ashworth, S. Kumar, and R. E. Hawkins.

1995. Idiotypic DNA vaccines against B-cell lymphoma. *Immunol. Rev.* 145:211-228), and viral antigen, HIV gp120. The appeal of this approach was based not only on the ability of these mediators of innate and adaptive immunity to target surface receptors on APC, particularly on iDC (Yang, D., O. Chertov, S. N. Bykovskaia, Q. Chen, M. J. Buffo, J. Shogan, M. Anderson, J. M. Schroder, J. M. Wang, O. M. Howard, and J. J. Oppenheim. 1999. Beta-defensins: linking innate and adaptive immunity through dendritic and T cell CCR6. Science 286:(5439)525-528), presumably resulting in increased uptake of antigen, but possibly also to induce of expression of co-stimulatory molecules and, in turn, production of other pro-inflammatory cytokines and factors. This example demonstrates that both murine β-defensin 2 and 3 efficiently induced chemotaxis of immature, but not mature, murine bone marrow derived DC, suggesting that a β-defensin specific receptor(s) is expressed on immature DC.

Example 6

As an example of how the vaccine of this invention can be administered to a patient to treat cancer or to treat or prevent HIV infection (with the additional administration of adjuvants, such as immunostimulatory cytokines, if desired), the following is a complete protocol for a clinical trial describing the administration of Id-KLH and GM-CSF to patients to treat follicular lymphoma. The same study design can be employed for the administration of the defensin-tumor antigen fusion polypeptide or the defensin-viral antigen fusion polypeptide of the present invention or nucleic acids encoding the fusion polypeptides of this invention, with appropriate modifications, as would be apparent to one of skill in the art. In particular, studies to test the efficacy of HIV vaccines are well known in the art and the clinical protocol described herein can be readily modified by one of skill in the art as appropriate to test the efficacy of the HIV fusion polypeptide or HIV fusion polypeptide-encoding nucleic acid of this invention according to well known protocols for testing HIV vaccines (126,127).
Background and Rationale
Immunoglobulin (Ig) molecules are composed of heavy and light chains, which possess highly specific variable regions at their amino termini. The variable regions of heavy and light chains combine to form the unique antigen recognition site of the Ig protein. These variable regions contain determinants that can themselves be recognized as antigens, or idiotopes. B-cell malignancies are composed of clonal proliferations of cells synthesizing a single antibody molecule with unique variable regions in the heavy and light chains. B-cell lymphomas are neoplasms of mature resting and reactive lymphocytes which generally express synthesized Ig at the cell surface. The idiotypic determinants of the surface Ig of a B-cell lymphoma can thus serve as a tumor-specific marker for the malignant clone.

Studies in experimental animals, as well as in man, have demonstrated the utility of the Ig idiotype as a tumor-specific antigen for the study of the biology of B-cell lymphoma in vitro and as a target for passive immunotherapy in vivo (1, 2, 3). Furthermore, active immunization against idiotypic determinants on malignant B cells has been demonstrated to produce resistance to tumor growth in a number of syngeneic experimental tumor models, as well as specific anti-tumor therapy against established tumors (4-13). These results, taken together, provided the rationale for testing autologous tumor-derived idiotypic surface Ig (Id) as a therapeutic "vaccine" against human B-cell lymphoma. Furthermore, preclinical studies in subhuman primates demonstrated that optimal immunization with human lymphoma-derived Id required conjugation of the protein to an immunogenic protein carrier (keyhole limpet hemocyanin; KLH) and emulsification in an adjuvant (14).

Guided by these observations, nine patients with B-cell lymphoma were immunized with autologous Id protein (15). These patients received no anti-tumor therapy during the time of the study. They were either in complete remission or in a state of minimal residual disease following conventional chemotherapy. In addition, three patients with rapidly progressive recurrent lymphoma were enrolled in a separate safety study; all three required reinstitution of chemotherapy shortly after enrollment, did not complete the immunization series, and were not studied further. They received intramuscular injections of 0.5 mg of Id conjugated to KLH at 0, 2, 6, 10 and 14 weeks, followed by two booster injections at 24 and 28 weeks. Patients in the first trial (five patients) received Id-KLH alone for the first three immunizations, then Id-KLH emulsified in a Pluronic polymer-based adjuvant vehicle formulation for all subsequent immunizations. Because no idiotype-specific immune responses were observed prior to the addition of the adjuvant to the program in this first group of patients, patients in the second trial (four patients) received the entire series of immunizations with this adjuvant. All patients were analyzed for idiotype-specific antibody production and peripheral blood mononuclear cell (PBMC) proliferative responses in vitro immediately before each immunization and at one to two month intervals following the last immunization. The KLH carrier provided a convenient internal control for immunocompetence of the patients and all patients demonstrated both humoral and PBMC proliferative responses to the KLH protein, with the exception of one patient, who demonstrated only the latter. Seven of the nine patients demonstrated either a humoral (n=2) or a cell-mediated (n=4) anti-idiotypic immunological response, or both (n=1).

Anti-idiotypic antibody responses were detected by analysis of pro- and hyper-immune sera in either direct, or competition, ELISA. The immunization with autologous Id protein induced significant titers of anti-idiotypic antibody that either directly bound or inhibited the binding of a murine anti-idiotype monoclonal antibody (anti Id mAb) to Id on the plate. The specificity of the humoral response for the Ig idiotype was demonstrated by the lack of significant binding of hyperimmune serum to a panel of isotype-matched human Igs of unrelated idiotype, or by the lack of significant inhibition of a panel of heterologous Id-anti-Id systems, respectively. Peak humoral responses were obtained after the fifth immunization and persisted for at least nine months. The anti-idiotypic antibody produced by patient 1 was affinity-purified and shown to contain heterogeneous light chains as well as immunoglobulin G heavy chains. This patient's antibody titer was successfully boosted with a single administration of Id-KLH in adjuvant after a decline of the humoral response after 15 months.

Cellular immune responses were measured by the proliferation of PBMC to KLH and to autologous Id separately at concentrations ranging from 1-100 μg per milliliter of soluble protein in five day in vitro cultures. None of the pre-immune PBMC demonstrated any preexisting proliferation to autologous Id above that to culture medium alone. Hyperimmune PBMC from all patients demonstrated strong proliferative responses to the KLH carrier. Of primary interest, significant hyperimmune proliferative responses to Id were detected in five patients. Although their responses were of lower magnitude than parallel responses to KLH, patients 3, 4, 6, 8 and 9 were classified as responders on the basis of reproducible increases in counts-per minute (cpm) $^3$H-thymidine incorporation in wells containing Id, compared with medium alone, that were sustained over multiple time points. Patients demonstrating occasional increases in cpm in wells containing Id compared with medium alone were classified as non-responders (patients 1 and 5).

Flow cytometry analysis of cultures demonstrating proliferation to Id revealed a predominance of cells staining positively for CD4 (>95%), suggesting the phenotype of the responding cell subpopulation. These cultures could be successfully expanded for approximately four weeks by stimulation alternatively with interleukin-2 (IL-2) and Id-pulsed autologous irradiated PBMC as antigen-presenting cells. Specificity of the responses for Ig idiotype was confirmed by the lack of significant proliferation to an isotype-matched human Ig of unrelated idiotype compared with medium alone. Such idiotype-specific PBMC proliferative responses were observed only after the addition of the adjuvant to the program and also persisted for at least 9-14 months.

The ability of the idiotype-specific humoral response to bind autologous tumor cells was also tested. This was shown by the inhibition of binding of a labeled murine anti-idiotype mAb to tumor cells from a pre-treatment lymph-node specimen from patient 8 by hyperimmune, but not by pre-immune, serum from this patient. In addition, affinity purified anti-idiotypic antibodies from the hyperimmune sera of the two other patients who demonstrated idiotype specific humoral responses were demonstrated by flow cytometry to bind autologous tumor.

All patients were also closely monitored for disease activity with physical examinations and routine laboratory and radiographic studies. Of the two patients with measurable tumor at the initiation of Id immunization, one (patient 1) experienced complete regression of a single 2.5 cm left submandibular lymph node, and the other (patient 4) experienced complete regression of a 4.5 cm cutaneous lymphomatous mass on the right arm. This clinical response in patient 4 correlated with an Id-specific, PBMC proliferative response in vivo. Correlating with the duration of their immunological responses, the clinical responses in both patients have continued at 24 and 10 months, respectively, after completion of the immunization series. Moreover, with a median follow up time of 10 months, the only case of tumor recurrence among those patients who were in remission and completed the immunization series occurred in patient 5, who was one of the two patients who failed to demonstrate an idiotype-specific immunological response.

Toxicity was minimal in all twelve patients. All patients experienced transient local reactions characterized by mild erythema, induration, and discomfort, without skin breakdown, at the injection sites. Splitting the components of the vaccine (Id-KLH and adjuvant) in one patient who had experienced a moderate local reaction and in another patient who had experienced a moderate systemic reaction, characterized by fever, rigors and diffuse arthralgias, established the adjuvant as the component associated with these reactions. Both of these moderate reactions resolved completely after 24-48 hours. The only laboratory abnormality associated with Id immunization was a mild elevation (less than twice the normal value) of serum creatine phosphokinase 24 hours after immunization in an occasional case.

These results demonstrate that patients with B-cell lymphoma can be induced to make sustained idiotype-specific immune responses by active immunization with purified autologous tumor-derived surface Ig. They show that autologous Id, made immunogenic by conjugation to KLH, can serve as an immunogen (antigen) to elicit host immunological responses. The induction of low levels of idiotype-specific immunity was demonstrated in the setting of minimal tumor burden following conventional chemotherapy. These results, taken together with the induction of relatively stronger immune responses to the KLH carrier, and exogenous antigen, suggest that chemotherapy-induced immunosuppression is not an obstacle to active immunotherapy administered adjunctively to cytoreductive drug therapy in this manner.

This initial study also established the requirement for an immunological adjuvant, as no Id-specific responses were observed prior to the addition of an adjuvant to the program The objective of further clinical trials using tumor derived Id as a therapeutic vaccine is to further optimize the immunogenicity of this vaccine. To this end, this study will focus on the use of novel immunological adjuvants which are 1) more potent and 2) more effective in the induction of cell-mediated immune responses, compared with the pluronic polymer-based adjuvant used in the study.

The 38C13 B cell tumor is used as a model system to screen promising immunological adjuvants. A number of these have included cytokines and among these, GM-CSF has emerged as a promising adjuvant for idiotypic Ig antigen. In these experiments (10 mice per group), syngeneic mice were immunized with 50 µg Id-KLH derived from the tumor, either alone or in combination with GM-CSF mixed together with the antigen and administered subcutaneously. Three additional daily doses of GM-CSF were administered s.c. as close to the original site of immunization as possible. Mice immunized with an irrelevant Id-KLH (4C5 IgM) served as negative controls for the vaccine. Two weeks after this single immunization, all mice were challenged with a single preparation of 38C13 tumor cells ($5 \times 10^3$ cells i.p.) and followed for survival. The results demonstrated that the augmented survival benefit afforded by immunization with relevant Id-KLH alone can be significantly enhanced by the addition of GM-CSF at either the 100 or 10,000 unit dose. The loss of this protective effect at a higher dose of GM-CSF of 50,000 units was also observed. These data suggest that GM-CSF may have a potent adjuvant effect in vivo for Id-KLH antigen, especially at relatively low doses.

The follicular lymphomas are follicular small cleaved cell (FSC) and follicular mixed lymphoma (FM). Stage I and II patients comprise only 10% to 15% of all cases of follicular lymphomas and are best managed with radiation therapy. Eight-five percent of patients with follicular lymphomas present with stage III or IV disease. The optimal management of these patients remains controversial and has generally followed two divergent approaches (16, 17). One is an aggressive approach, which has included radiation therapy, combination chemotherapy, or combined modality therapy and the other is a conservative approach that involves no initial treatment followed by a single-agent chemotherapy or involved-field radiotherapy when required (18; 19). Most forms of systemic therapy have the capacity to produce high complete response rates. However, they have failed to produce long-term disease-free survival or to prolong overall survival; thus, it has become clear that the vast majority of patients with this disease will relapse and die of their lymphoma, despite its usually indolent course.

The NCI study (MB-110, BRMP 8903) begun in 1978, is a prospective randomized study comparing these two distinct approaches to the management of stage III or IV indolent histology lymphoma. Most patients were randomized between no initial therapy or aggressive combined modality therapy with ProMACE/MOPP flexitherapy followed by low dose (2400cGy) total nodal irradiation. Among the 149 patients treated thus far, 125 (84%) were randomized; 62 to watch and wait (W & W) and 63 to aggressive treatment. Among the 62 patients on the watch and wait arm, 29 continue to be observed for periods up to 10+ years. The median time to cross over to aggressive therapy is 23 months.

It is apparent that patients in whom therapy is initiated after the development of symptoms have a significantly lower complete response rate to therapy than patients randomized to receive the same therapy at diagnosis (74% vs 40%, $P_2$=0.0039). The complete responder (CR) rate of patients randomized to initial aggressive treatment is comparable to those obtained in patients with advanced-stage intermediate grade lymphoma receiving the same treatment. The CR rate in indolent lymphoma does not appear to be significantly higher than what can be achieved with other combination regimens. For patients randomized to watch and wait, median follow-up of CRs is shorter because of the delay in initiating treatment. However, the median duration of remission has not been reached at five years and 57% of patients are projected to be disease-free>8 years and 44% are projected to be in a CR at 12 years. The disease-free survival curves are not significantly different between the two arms. Thus, allowing the patient to reach a greater tumor burden before instituting systemic therapy reduces the likelihood of obtaining a CR, but once achieved, CRs are comparably durable to those obtained from primary aggressive therapy. The lengthening of the remission duration, however, has not resulted in a survival advantage for patients randomized to receive primary aggressive chemotherapy. Furthermore, even though a minority of complete responders have relapsed, the probability of relapse appears to be continuous over time, and the vast majority of patients are expected to eventually succumb to their disease.

Thus, even immediate aggressive therapy has not resulted in improved survival. Therefore, although patients diagnosed with follicular lymphoma enjoy relatively longer survival times compared with patients with solid tumors, follicular lymphoma remains an incurable disease. Novel experimental therapies designed to improve the durability of the remissions already effectively induced by chemotherapy are justified.

Summary of Treatment Plan

The goal is to treat patients with follicular lymphomas to complete remission or maximal response with ProMACE chemotherapy. After the completion of chemotherapy, in an effort to reduce the relapse rate (by eradicating microscopic disease resistant to chemotherapy), patients will receive an autologous Id vaccine administered in combination with GM-CSF.

The goal of this study is to evaluate the ability of the Id vaccine to clear the bone marrow of malignant cells detectable by pathologic (morphologic) examination or molecular examination (polymerase chain reaction, PCR) in patients with PCR amplifiable translocations. All patients have serial bone marrow and peripheral blood samples collected to search for clonal abnormalities by PCR. Patients are followed after vaccine therapy and their remission status correlated with clinical vs. molecular determinations of response. There should be three categories of complete responders: those who had a clinical complete response before the vaccine but had an abnormal clone by PCR that cleared after the vaccine; those with a clinical CR before the vaccine who were also PCR negative before the vaccine; and those who achieved a clinical complete response but had PCR positive marrows before and after the vaccine. It is a goal of this study to assess whether "molecular complete responses" can be achieved using the vaccine in patients following chemotherapy.

Objectives

The objectives of this trial are to:

To induce cellular and humoral immunity against the unique idiotype expressed on the surface of patients' B-cell lymphomas.

To determine the ability of Id immunization to eradicate bcl-2 positive tumor cells from the bone marrow as detected by PCR.

As a secondary objective, to determine the more biologically active of the two GM-CSF doses as an adjuvant, as measured by the endpoints in the above objectives.

To determine the impact of Id immunization on disease free survival of patients achieving a CR with chemotherapy.

Patient Selection

Patient Sample

A. Sample size, approximately 42 patients

B. Sex distribution: male and female

C. Age: patients must be ≧18 years old

Eligibility Criteria

Patient must meet all of the following eligibility criteria:

A. Tissue diagnosis of: follicular small cleaved cell, or follicular mixed lymphoma with surface IgM, IgG or IgA phenotype with a monoclonal heavy and light chain. Pathology slides must be submitted to the NIH Pathology Department for review.

B. Stage III or IV lymphoma.

C. Only previously untreated patients are eligible.

D. Previous treatment with radiation alone (less than TBI) is permissible.

E. A single peripheral lymph node of at least 2 cm size accessible for biopsy/harvest.

F. Karnfsky status ≧70%.

G. Life expectancy of >one year.

H. Serum creatinine ≦1.5 mg/dl unless felt to be secondary to lymphoma.

I. Bilirubin ≦1.5 mg/dl unless felt to be secondary to lymphoma or Gilbert's disease. SGOT/SGPT<3.5× upper limit of normal.

J. Ability to give informed consent. Ability to return to clinic for adequate follow-up for the period that the protocol requires.

Patient Exclusion Criteria

The presence of any exclusion criteria (listed below) will prohibit entry into study:

A. Prior total body irradiation.

B. Presence of antibodies to HIV, hepatitis B surface antigen or other active infectious process.

C. Pregnancy or lactation. Fertile men and women must plan to use effective contraception. A beta-HCG level will be obtained in women of childbearing potential.

D. Patients with previous or concomitant malignancy, regardless of site, except curatively treated squamous or basal cell carcinoma of the skin, or effectively treated carcinoma in situ of the cervix.

E. Patient unwilling to give informed consent.

F. Failure to meet any of the eligibility criteria described above.

G. Any medical or psychiatric condition that in the opinion of the protocol chairman would compromise the patient's ability to tolerate this treatment.

H. Patient with CNS lymphoma (current or previously treated) will not be eligible.

Clinical Evaluation

Complete history and physical examination.

CBC, diff., platelet count.

Serum chemistry, $β_2$-microglobulin.

PT/PTT

Quantitative immunoglobulins, serum protein electrophoresis, immunoelectrophoresis.

HIV antibody, HBsAg.
Urinalysis.
Serum β-HCG in women of child-bearing potential.
EKG and MUGA.
5 TT for serum storage.
Leukapheresis to obtain $3 \times 10^9$ lymphocytes. These samples will be used for baseline studies of T-call activation and response to Id.

Tumor Biopsy—prior to therapy, all patients must undergo biopsy/harvest of a clinically involved peripheral lymph node to obtain tissue for morphological classification, immunophenotypic characterization, determination of immunoglobulin gene rearrangements, bcl-2 translocation, cytogenetics, and to provide starting material for an Id vaccine. The sample should be at least 2 cm in size. Only patients with tumors that are surface immunoglobulin positive with a monoclonal heavy and light chain will be accepted as study candidates. Use standard lymphoma vaccine biopsy orders (see protocol below). Leftover tumor biopsy samples may be used for basic studies of lymphoma biology in vitro. Such future studies may be done without re-consenting the subjects only if the studies involve risks already outlined in the original consent form.

CXR—PA and LAT.
CT scan of abdomen and pelvis.
Lymphangiogram, unless contraindicated by massive pedal edema, severe chronic lung disease, ethiodal sensitivity (Note: sensitivity to other iodine compounds, e.g., renografin, are relative, but not absolute contraindications).

Other tests (CT chest, ultrasound, liver scan, bone scan, upper and lower GI series, IVP, MRI) should be performed as needed to evaluate all disease sites adequately.

Examination of pleural fluid or ascites when present.
Bilateral bone marrow aspirates and biopsies—In addition to the normal aspirate and biopsy, 5 cc of marrow will be aspirated from each side into 0.5 ml of PFH for PCR analysis. The procedure should be performed in the usual manner with a biopsy performed first. Then a small volume (0.5-1 cc) can be aspirated for the smear and clot tube. A separate Rosenthal needle with bevel should be used for the aspirate. The 5 cc sample for PCR can be obtained from the same site as the initial aspirate.

CT scan of the head and lumbar puncture with CSF analysis if clinically indicated.

Patient Registration
Patients will be registered prior to the initiation of therapy at which time eligibility criteria will be reviewed. Stratification and randomization are described in detail below (see Statistical considerations).

Study Design

| ProMACE | | |
|---|---|---|
| Day 0 | Day 7 | Day 28 |
| Cyclophosphamide 650 mg/m² IV | Cyclophosphamide 650 mg/m² IV | Next cycle begins |
| Doxorubicin 25 mg/m² IV | Doxorubicin 25 mg/m² IV | |
| Etoposide VP-16 120 mg/m² IV | Etoposide BP-16 120 mg/m² IV | |

Prednisone 60 mg/m² po qd x 14 (days 0 to 13)
Bactrim one double strength tablet po BID throughout therapy All patients will be treated until a complete remission is obtained and two additional cycles of chemotherapy have been given, or until disease has been stable for two cycles of chemotherapy, or progressive disease develops. A minimum of six cycles will be given to each complete responder before therapy is discontinued. Patients with more than 90% PR or a full CR will be continued on the vaccination part of the protocol. Patients with less than 90% PR or progressive disease will be taken off of the study.

Postinduction Therapy—Three to six months (or whenever a customized GMP vaccine is available, up to a maximum period of 12 months) after the completion of chemotherapy, all patients in whom either a complete clinical remission or minimal disease status ($\geq$90% partial response) has been achieved will receive a series of five injections of a vaccine consisting of 0.5 mg autologous tumor derived immunoglobulin (Id) conjugated to KLH. The vaccine will be administered together with GM-CSF as an immunological adjuvant. Both the vaccine and GM-CSF will be administered subcutaneously according to the following schedule:

Schedule:
At 0, 1, 2, 3 and 5 months
Id-KLH (0.5 mg s.c.) day 0
adjuvant (s.c.) days 0-3
Cohort 1: GM-CSF 500 mcg/m²/d s.c. for 4 days
Cohort 2: GM-CSF 100 mcg/m²/d s.c. for 4 days The sites of injection will be rotated between the upper and lower extremities. Each dose of vaccine or GM-CSF will be split equally between the two upper or lower extremities. All GM-CSF injections will be given in close proximity to the vaccination site, as close to the exact site of injection as possible. If local reactions to GM-CSF are severe, GM-CSF injections may be given elsewhere. Patients will be observed in the clinic for two hours following Id-KLH and/or GM-CSF administration. During the observation period, vital signs will be taken every 15 minutes during the first hour and every 30 minutes during the second hour.

Supportive Care
G-CSF 5 mcg/kg/d SC may be used in all patients who are hospitalized for the treatment of febrile neutropenia, regardless of how long the neutropenia persists.

Grading and Management of Toxicity
Chemotherapy: Dose modification of chemotherapy will be based on the granulocyte count done at the time of drug administration (day 0 or 7 of each cycle). The percentage of drugs administered may be further modified based on toxicity in prior cycles (see below). If the granulocyte count is <1200, and the patient is due for day 0 drugs, delay day 0 for one week until appropriate parameters are met. In general, delays of up to one week are preferable to starting G-CSF. If after a one week delay, appropriate parameters are still not met, then G-CSF may be started as above. Also, in general, delays of up to one week are preferable to dose reductions. Full doses of all drugs should be given on time if blood count suppression is due to bone marrow involvement with disease.

Dose Modification for Hematologic Toxicity

| IF GRANULOCYTE COUNT IS: On Day 0 | THEN DOSE AS FOLLOWS: |
|---|---|
| $\geq$1200 | 100% all drugs |
| $\leq$1200 | Day 0 Delay |

For neutrophil nadir <500 or platelet count <25,000 on previous cycle, 75% of cyclophosphamide, doxorubicin, and etoposide should be considered. For neutrophil nadir (day 21 counts)>750 on a previous cycle, dose escalation of cyclophosphamide, doxorubicin, and etoposide by 10-20% should be prescribed.

| IF PLATELET COUNT IS: | THEN DOSE AS FOLLOWS: |
|---|---|
| >100,000 | 100% of all drugs |
| 50-99,999 | 100% Prednisone |
| | 75% Etoposide |
| | 50% Cyclophosphamide, Doxorubicin |
| <50,000 | Delay |

Dose Modification for Non-Hematologic Toxicity

Assessment of non-hematologic toxicity will be graded according to the CRB/DCS/NCI Common Toxicity Criteria. Chemotherapy will be withheld in patients experiencing grade 2 or greater non-hematologic toxicity until the patient has completely recovered from the toxicity. For nausea/vomiting 2: grade 2, drug therapy should be continued with non-steroid antiemetics.

Doxorubicin dosage should be adjusted as follows in the presence of the following LFT abnormalities:

| % Dose | Bilirubin | SGOT |
|---|---|---|
| 100 | <1.5 mg/dl | <75 U |
| 50 | 1.5-2.9 mg/dl | 75-150 U |
| 25 | 3.0-5.9 mg/dl | 151-300 U |
| 0 | ≧6.0 mg/dl | >300 U |

Immunotherapy

Id-KLH Vaccine

Based on previous experience with autologous Id-KLH vaccines, little or no toxicity is expected from the Id-KLH component of the vaccine (15). Nevertheless, any local skin reactions will be carefully noted and scored for erythema, induration, pain and disruption of the barrier surface. If any patient has a reaction suggestive of sensitization, the vaccine may be split into its component parts; specifically, the patient will be tested with Id-KLH alone and then GM-CSF alone. Toxicities will be graded according to the CRBINCI/DCS common toxicity criteria.

GM-CSF

Anticipated toxicities from GM-CSF administration in this dose range are expected to be mild based on previous experience. Potential toxicities include fever, chills, myalgias, arthralgias, nausea, vomiting, diarrhea, dyspnea, tachycardia, arrhythmias, elevation of liver function tests, elevation of BUN and creatinine. However, local skin reactions, such as erythema and induration, may be observed and will be carefully noted. Attempts will be made to maintain these patients as outpatients. For grade IV fever (not responsive to Indocin or Tylenol), or grade III vomiting (unresponsive to therapy), GM-CSF will be held until toxicity is less than grade II and will be restarted at 50% of the original dose level for the rest of that weekly injection cycle and for subsequent cycles. For neurologic toxicity that affects daily function (unable to carry on simple routine duties, or grade II in the toxicity grading scale), hold treatment until symptoms resolve, then reduce GM-CSF by 50%. If symptoms persist, the adjuvant should be removed for subsequent immunizations. Patients with grade III neurotoxicity will be removed from the study.

For well-documented evidence of cardiac toxicity (i.e., grade III, including evidence of ischemia or ventricular arrhythmia, but not supraventricular tachycardia or atrial fibrillation controlled by digoxin or calcium channel blocking agents), the adjuvant will be removed for subsequent immunizations.

Asymptomatic elevations in serum bilirubin and creatinine (not resulting in hyperkalemia) will be tolerated. For SGOT or SGPT >10× normal, GM-CSF will be held until values return to <5× normal, then resumed at 50% of the GM-CSF dose for all remaining doses.

Fever and chills associated with vaccine administration and/or GM-CSF will be treated with TYLENOL and/or DEMEROL. The use of non-steroidal antiinflammatory drugs and/or steroids should be avoided. Should non-steroidals or steroids be required for unrelated medical conditions for a course exceeding 2 weeks, the patient will be taken off of the study.

Adverse Drug Reactions

All toxicities and adverse events will be recorded on the study flow sheet and appropriately graded as to severity and cause. Toxicities that are related to the underlying disease should be clearly differentiated from drug toxicities.

Adverse drug reactions related to chemotherapy will be submitted based on guidelines for commercial drugs.

Reports of adverse reactions to Id-KLH and GM-CSF will be made using the Division of Cancer Treatment Common Toxicity Criteria for reference according to the guidelines published by the DCT, NCI. These guidelines can be summarized as follows:

A. Report by telephone to IDB within 24 hours (301) 230-2330
  1. All life-threatening events (grade 4, except for grade 4 myelosuppression) which may be due to administration of the investigational drug(s),
  2. All fatal events (grade 5),
  3. All first occurrences of any previously unknown toxicity (regardless of grade).
B. A written report should follow within 10 working days.
C. All adverse drug reactions will also be reported in writing to the NCI Institutional Review Board within 10 working days.
D. All adverse drug reactions will also be reported to the FDA in accordance with Federal regulations.
E. Data will be submitted at least every two weeks.

Study Parameters

During Chemotherapy
  Weekly: CBC, diff. platelets; except day 14, i.e. CBC on day 0, 7, 21, and 28.
  Beginning of each cycle: Chem 20, CXR, LAG follow-up (KUB), CT scans (only after 4 cycles, then every 2 cycles).
  Bilateral bone marrow aspirate and biopsy after four cycles and every additional two cycles thereafter. Include 5 cc of aspirate in PFH from each side for PCR analysis.

At Maximal Response to Chemotherapy
  If residual disease is obvious, record measurements and perform bone marrows as above.
  For complete responders, complete restaging should be performed. This should include all studies that were positive at initial staging evaluation with the exception of repeat thoracotomy or laparotomy. Bilateral bone marrows should be performed as above.

During Vaccine Therapy
  If residual disease is obvious, record measurements and perform bone marrows as above.
  PT-PTT day 0
  UA, $\beta_2$ microglobulin day 0 of each immunization.
  Leukapheresis is performed on the day of initiation of vaccine therapy (prior to the first cycle only) to obtain pre-vaccine lymphocytes for storage. Five tiger top tubes are drawn at this time to obtain serum for storage.

Two tiger top tubes and peripheral blood (60 cc in PHI) are collected on day 0 of each monthly cycle, for preparation of serum and lymphocytes, respectively.

Skin Biopsy is obtained near a planned immunization site on day 0 prior to the first cycle (baseline sample) and again on day 1, 2, or 3 of cycle 3 at an active site of erythema and/or induration as close to the original biopsy site as possible.

DTH—Delayed type hypersensitivity test (DTH) to autologous idiotype protein is performed during cycle 4 and again following completion of the immunization regimen, i.e., during or after cycle 5. The DTH-test is performed by intradermal injection of 0.5 mg of idiotype protein in 0.1-0.2 ml of NS. To ascertain the specificity of a positive reaction, 0.5 mg of a heterologous isotype matched Id-protein (from another patient on the same study) in the same volume will be used as a negative control. The control idiotypes used on these two occasions will be from two different patients, also in the study, in order to minimize the possibility of eliciting an immunologic response against a particular irrelevant idiotype. A skin biopsy will also be obtained at the site of the intradermal injection of idiotype protein and at the control site, one to three days, after the intradermal injections.

Fine needle aspiration or core biopsy (with or without CT guidance) of any enlarged lymph node draining the vaccination sites is performed to obtain lymphocytes for in vitro assays.

At Discontinuation of Vaccine

Restaging as described for Chemotherapy (see "At Maximal Response to Chemotherapy," above).

Bilateral bone marrow aspirates and biopsies at completion of therapy and every six months for two years after completing therapy and yearly thereafter.

10 cc of serum for storage and 60 cc of peripheral blood in PFH is collected at completion of therapy and every three months for a year.

Specimen Processing and Immunological Assays

Lymph Node Harvest/Biopsy

Each lymph node biopsy will be divided as follows: (a) one-third of the specimen will be sent in saline to the Hematopathology Section, Laboratory of Pathology, NIH. Biopsies are processed for routine histopathy and for immunophenotypic characterization, particularly with respect to monotypic heavy and light chain expression; and (b) two-thirds of the specimen is sent in sterile saline in a sterile container to Clinical Immunology Services, NCIFCRDC, where it is processed into a single-cell suspension and cryopreserved.

Blood and Bone Marrow Samples

All peripheral blood and bone marrow aspirate samples are sent in an expedited manner to Clinical Immunology Services, NCI-FCRDC. Tiger top tubes are spun down and serum divided into 1 ml aliquots for frozen storage. Peripheral blood mononuclear cells (PBMC) are isolated prior to freezing by Ficoll-hypaque centrifugation using standard protocols.

Assay for Serum Antibody

In a direct enzyme-linked immunosorbent assay (ELISA), preimmune and hyperimmune serum samples from each patient are diluted over wells of a microtiter plate that are coated with either autologous immunoglobulin idiotype or a panel of isotype-matched human tumor immunoglobulins of unrelated idiotype. Bound antibody is detected with horseradish peroxidase-goat antihuman light-chain antibodies directed against the light chain not present in the immunoglobulin idiotype (Caltag Laboratories, South San Francisco).

Assay for Idiotype-Specific Proliferative Response

Whenever feasible, fresh PBMC, isolated above, are used on the same day they are obtained. Stored frozen PBMC are available as a back-up. PBMC are washed and plated at a concentration of $4 \times 10^5$ cells per well in Iscove's modified Dulbecco's medium (IMDM) with 1 percent human AB7 serum (IMDM-1 percent AB). KLH, autologous immunoglobulin idiotype, or a panel of isotype matched immunoglobulins of irrelevant idiotypes at concentrations of 0 to 100 µg per milliliter in IMDM-1 percent AB preparation are added in triplicate. After the cells are incubated for three days at 37° C. in an atmosphere containing 5 percent carbon dioxide, they are transferred to a preparation of IMDM and 5 percent fetal-calf serum containing recombinant interleukin-2 (30 Upper milliliter). The plates are incubated for two days and pulsed for 16 to 20 hours with $^3$H-labeled thymidine (1 µCi per well). Data are expressed as mean (±SEM) counts per minute of [$^3$H]thymidine incorporation.

Initial five-day cultures of PBMCs established as described above are expanded in IMDM-5 percent fetal-calf serum containing interleukin-2 (30 Upper milliliter). Harvested cells are replaced in IMDM-1 percent AB containing autologous immunoglobulin idiotype and fresh irradiated (5000 R) autologous PBMCs ($4 \times 10^5$ cells per well) as antigen-presenting cells for five days, before pulsing with $^3$[H]thymidine.

Cytotoxicity Assays

The potential cytotoxicity of PBMC cultured with Id as above, or with irradiated fresh cryopreserved tumor cells, is assayed against either autologous lymphoblastoid cell lines (LBL) pulsed with Id or fresh cryopreserved tumor targets. Autologous LBL pulsed with soluble antigen have been used successfully as targets to detect gp 160-specific cytotoxic T-lymphocytes (20). Historically, the inability to establish long-term cultures of follicular lymphoma has hindered their availability as targets. However, two recent reports have described the use of fresh cryopreserved lymphoma cell targets, with levels of spontaneous incorporated radioisotope release in the acceptable range of <35% (21-22). Standard four hour $^{51}$Cr release, as well as 18-24 hour $^{111}$In release assays are used.

Autologous LBL are prepared from pre-immune PBMC by the AIDS Monitoring Laboratory, NCI-FDRDC, using published methods.

Monitoring of T-Cell Receptor (TCR) Status

Pre-chemotherapy and pre- and postimmunization serum samples are assayed for TCR status by Western blot assay. Approximately $7 \times 10^6$ purified T-cells from PBMC are lysed for 5 minutes at 4° C. in lysis buffer (25 mM Tris, pH 7.4 [Sigma Chemical Co., St Louis, Mo.], 300 mM NaCl, 0.05% Triton X-100, 1 mM Na orthovanadate, 10 µg/ml aprotinin, 10 µg/ml leupeptin, 10 mM nitrophenol-guanidine benzoate [NPGB] and 5 mM EDTA). The lysates are centrifuged at 12,000 rpm at 4° C. for 5 minutes and supernatant is removed with a micropipettor, making sure the nuclear pellet is not disturbed. A sample of the supernatant is then used to quantitate protein using the BCA protein assay (Pierce, Rockford, Ill.). The rest of the lysate is boiled with 3× reducing sample buffer for 5 minutes and placed on ice before its use in Western blot.

Varying concentrations of cellular lysate ranging between 1 and 30 µg are electrophoresed in 14% Tris-glycine gels (Novex Experimental Technology, Calif.) under reducing conditions and then transferred to Imobilon-p PVDF transfer membranes (Millipore Co., Bedford, Mass.). The membranes are incubated with a 5% solution of non-fat dried milk for one hour and then blotted for one hour at room temperature with anti-TCRζ anti-serum (Onco-Zeta 1, OncoTherapeutics, Cranbury, N.J.) at a 1:2000 dilution. The membranes are washed with TBS-T buffer [1 M Tris base, 5M NaCl, 0.1% Tween 20 (pH 7.5)] and incubated with anti-rabbit or anti-mouse Ig horseradish peroxidase (Amersham, Buckinghamshire, UK). After washing with TBS-T, the membranes are developed with the chemiluminescence kit ECL (Amersham, UK) for 1-5 minutes. X-OMAT AR film (Kodak Co., Rochester, N.Y.) is used to detect the chemiluminescence.

PCR Amplification of Rearranged bcl-2

Nested oligonucleotide amplification is performed at the MBR or mcr of the bcl-2/$Ig_H$ hybrid gene using previously published methods (23). Briefly, samples containing 1 µg of genomic DNA are initially amplified for 25 cycles in a final volume of 50 µg containing 50 mmol/L KCl, 10 mmol/L Tris HCL, 2.25 mmol/L $MgCl_2$, 200 mmol/L oligonucleotide primers, 200 mmol/L each of dGTP, dCTP, dTTP and dATP, and 1.5 U Tag polymerase (Cetus, Emeryville, Calif.). Reamplification of an aliquot of product is performed for 30 cycles in a final volume of 50 µl using identical conditions to the original amplification, with oligonucleotide primers internal to the original primers. Aliquots of the final product are analyzed by gel electrophoresis in 4% agarose gels containing ethidium bromide and visualized under UV light. DNA is Southern blotted onto Zeta-probe blotting membrane (Bio-Rad. Richmond, Calif.) and bcl-2-specific DNA is detected by hybridization with oligonucleotide probes radiolabeled with $^{32}P(ATP)$ using T4 polynucleotide kinase.

Removal of Patients from Protocol Therapy

Patients will be removed from protocol for any of the following reasons:
  Unacceptable toxicity (as defined above).
  The patient declines further therapy.
  The patient experiences progressive lymphoma.
  It is deemed in the best interest of the patient. In this instance,
  The Principal Investigator should be notified.
  The reasons for withdrawal should be noted in the flow sheet.

Response Criteria

Patients will be reevaluated for tumor response after every two cycles of chemotherapy using the following criteria:

Complete Response—disappearance of all clinical and laboratory (excluding PCR) signs and symptoms of active disease for a minimum of one month.
  Partial Response—a 50% or greater reduction in the size of the lesions as defined by the sum of the products of the longest perpendicular diameters of all measured lesions lasting for a minimum of one month. No lesions may increase in size and no new lesions may appear.
  Minimal Residual Response—a $\geq 90\%$ partial response. For most patients in this category, this will mean $\leq 10\%$ residual bone marrow involvement by lymphoma.
  Progressive Disease—an increase of 25% or more in the sum of the products of the longest perpendicular diameters of all measured indicator lesions compared to the smallest previous measurement or the appearance of a new lesion.

Drug Formulation and Toxicity Data

Cyclophosphamide (CTX. Cytoxan)-NSC #26271
    Source and Pharmacology—CTX is an alkylating agent, related to nitrogen mustard, which is biochemically inert until it is metabolized to its active components by the liver phosphoramidases. It is non-phase-specific. The drug is excreted exclusively by the kidney after parenteral administration.
    Formulation and Stability—CTX is supplied as a 100, 200, 500, 1000 mg and a 2 gram lyophilized powder with 75 mg mannitol per 100 mg (anhydrous) cyclophosphamide. The vials are stored at room temperature (59-86° F.) and reconstituted with sterile water for injection to yield a final concentration of 20 mg/ml as described in the package insert. Reconstituted cyclophosphamide is stable for at least 6 days under refrigeration and for 24 hours at room temperature. Reconstituted drug and diluted solutions should be stored under refrigeration.
    Supplier—Commercially available.
    Route of Administration—The cyclophosphamide used in this regimen is given IV over 30 minutes and is diluted in 100 cc of either $D_5W$ or NSS.
    Toxicity—Toxicities described with cyclophosphamide include nausea, vomiting, myelosuppression, gonadal failure in both males and females, alopecia, interstitial pneumonitis, pulmonary fibrosis. hemorrhagic cystitis, cardiac events (cardiomyopathy), syndrome of inappropriate antidiuretic hormone secretion (SIADH) and rarely, anaphylaxis.
  Prednisone (Deltasone. Meticorten, Liquid Pred) NSC#10023
    Source and Pharmacology—Prednisone is the synthetic congener of hydrocortisone, the natural adrenal hormone. It binds with steroid receptors on the nuclear membrane, blocks mitosis, and inhibits protein synthesis. It kills primarily during the S-phase of the cell cycle. It is catabolized in the liver and excreted in the urine. Peak blood levels occur within two hours after oral intake. Plasma half-life is 3-6 hours. (Biologic half-life is 12-30 hours.)

| Cortisone | 25 | |
|---|---|---|
| Hydrocortisone | 20 | Equivalent |
| Prednisone | 5 | strength in mg |
| Decadron | 0.75 | |

Formulation and Stability—Available in 1, 2.5, 5, 10, 20 and 50 mg tablets; 5 mg/5 ml liquid.
    Supplier—Prednisone is commercially available.
    Route of Administration—PO; NOTE: May cause GI upset; take with meals or snacks. Take in the morning prior to 9 a.m.
    Toxicity—Toxicities described with prednisone include fluid and electrolyte changes, edema, hypertension, hyperglycemia, gastritis, osteoporosis, myopathy, behavioral and mood changes, poor wound healing, and Cushing's syndrome (moon face, buffalo hump, central obesity, acne, hirsutism and striae).
  VP-16 (Etoposide.VePesid) NSC#141540
    Source and Pharmacology—VP-16 is a semisynthetic derivative of podophyllotoxin which inhibits topoisomerase II and functions as mitotic inhibitor, but does not bind microtubules. Its main effect appears to be in the S and $G_2$-phase of the cell cycle. The mean terminal half-life is 11.5 hours, with a range of 3 to 15 hours. It is primarily excreted in the urine.
    Formulation and Stability—VP-16 is supplied in vials containing either 100 or 500 mg of etoposide (20 mg/ml) in a polyethylene vehicle. VP-16 is diluted in either 500 cc of 5% dextrose or 0.9% Sodium Chloride Injection. Diluted solutions (concentrations of 0.2, 0.4 mg/ml and 1 mg/ml) are stable for 96, 48 hours and 2 hours, respectively at room temperature under normal room fluorescent light in both glass and plastic containers. Do not refrigerate etoposide-containing solutions.
    Supplier—VP-16 is commercially available.

Route of Administration—Etoposide is administered as an IV infusion over 60 minutes.

Toxicity—Toxicities described with etoposide administration include myelosuppression (neutropenia), nausea, vomiting, mucositis, allergic reactions characterized by anaphylactic symptoms and hypotension and alopecia.

Doxorubricin (Adriamycin) NSC #123127

Source and Pharmacology—Doxorubicin is an anthracycline antibiotic isolated from cultures of Streptomyces peucetius. It binds to DNA and inhibits nucleic acid synthesis, with its major lethal effect occurring during the S-phase of the cell cycle. Since it is primarily excreted by the liver, any liver impairment may enhance toxicity. Some of the drug has a very short $\alpha$ T½ of <20 minutes and a $\beta$½ of 17 hours. Animal studies indicate cytotoxic levels persist in tissue for as long as 24 hours. Biliary excretion also is a source of elimination for Doxorubicin; therefore, patients with hyperbilirubinemia/cholestasis caused by something other than lymphoma should have dosage modification.

Formulation and stability—Doxorubicin is available as a freeze-dried powder in 10, 50 and 150 mg vials. The drug is stored at room temperature, protected from light, and is reconstituted with sodium chloride 0.9% (NSS) to yield a final concentration of 5 mg/ml. The reconstituted solution is stable for 7 days at room temperature (15-30° C.) or if stored under refrigeration (2-8° C.).

Supplier—Doxorubicin is commercially available.

Route of Administration—Doxorubicin is given as a slow IV injection over 5-7 minutes through an established line with a free flowing IV.

Special precautions: Avoid extravasation and local contact with skin or conjunctiva.

Toxicity—Toxicities described with doxorubicin administration include myelosuppression, nausea, vomiting, mucositis, stomatitis, alopecia. diarrhea, facial flushing, dose-related congestive cardiomyopathy, arrhythmias, vein streaking (hypersensitivity reaction), radiation-recall dermatitis, local cellulitis, vesication and tissue necrosis upon extravasation (SQ and dermal necrosis).

ID-KLH Vaccine

Source—Idiotype protein from the individual B cell lymphomas is obtained from tissue culture, purified, and covalently coupled to keyhole limpet hemocyanin (KLH) as previously described. Each batch is produced according to Good Manufacturing Practices standards and tested for sterility, endotoxin contamination, and general safety prior to its use in any patient. The preparation and quality control/quality assurance testing of the Id-KLH conjugate is performed by TSI Washington under CRB contract. The IND for the Id-KLH vaccine will be held by the Drug Regulatory Affairs Section, CTEP.

How supplied—Formulated product for subcutaneous administration contains 0.5 mg of Id and KLH each per ml of normal saline. Id-KLH is supplied as a 1 ml vial.

Storage—Prior to administration, Id-KLH is stored at −20° C.

Administration—After thawing and gentle agitation, the vial contents are drawn up using an 18-gauge needle on a syringe. After the entire contents have been drawn up, the 18-gauge needle is replaced by a 25-gauge needle for injection. This procedure is important to ensure that all particulates (normal components of this vaccine) are obtained from the vial.

Toxicity—Toxicities described with Id-KLH vaccine administration include local site reactions (erythema, induration, swelling and tenderness), fever, chills, rash, myalgias and arthralgias. Mild elevations in creatinine phosphokinase (CPK) have been observed.

GM-CSF (Sargramostim: NSC #613795; BB-IND 2632

Source and Pharmacology—The GM-CSF used in this study is glycosylated, recombinant human GM-CSF. This GM-CSF is an altered form of the native molecule; the position 23 arginine has been replaced with a leucine to facilitate expression of the protein in yeast (Saccharomyces cerevisiae).

Formulation and Stability—The GM-CSF is formulated as a white lyophilized cake and is provided in vials containing 500 µg of the GM-CSF protein as well as 10.0 mg of sucrose, 40.0 mg of mannitol, and 1.2 mg of Tris (Trimethamine).

To prepare a vial of GM-CSF for direct subcutaneous use, aseptically inject 1.0 ml of Sterile Water for Injection, USP, into the vial to dissolve the lyophilized cake. The diluent should be directed against the side of the vial to avoid excess foaming. Avoid vigorous agitation of the vial; do not shake. This yields a solution containing 500 µg/ml. The unreconstituted material should be kept refrigerated at 2-8° C. and is stable for at least eighteen months. Once reconstituted, the solution is stable for at least 24 hours at 2-8° C. or at 18-25° C. Because the product does not contain a preservative, vials should be treated as unit-dose containers; reconstituted solution should be held at 2-8° C. and discarded after no more than six hours. Do not freeze GM-CSF.

Supplier. Manufactured by Immunex.

Route of Administration—The appropriate total dose is withdrawn into and administered from a plastic tuberculin syringe. The GM-CSF is injected subcutaneously as close as possible to the Id-KLH injection site. All GM-CSF doses for each patient are administered by the nursing staff in the outpatient unit.

Toxicity—Toxicities described in patients receiving GM-CSF include: fever, chills, diaphoresis, myalgias, fatigue, malaise, headache, dizziness, dyspnea, bronchospasm, pleural effusion, anorexia, indigestion, nausea, vomiting, diarrhea, injection site tenderness, urticaria, rash, pruritus, hypersensitivity reaction, bone pain, thromboembolic events, phlebitis, hypotension, peripheral edema, leukocytosis, thrombocytosis or thrombocytopenia, hepatic enzyme abnormalities, and bilirubin elevation. The first administration of GM-CSF has provoked a syndrome of dyspnea and hypotension within two hours after GM-CSF injection in a single patient receiving yeast-derived GM-CSF; this type of reaction has more frequently been observed in patients receiving GM-CSF produced in E. coli. One report of a vascular leak-like syndrome occurring after autologous bone marrow transplant in a patient receiving continuous IV infusion of GM-CSF has been recorded.

Unconjugated Lymphoma Immunoglobulin Idiotype (for Intradermal Skin Testing) NSC#684151

Source—The patient-specific purified idiotype protein, previously produced according to GMP standards as described above, is vialed as a separate product by TSI Washington Laboratories and will be supplied by CTEP, DCT, NCI. This vialed product is tested separately for sterility, endotoxin, and mycoplasma, according to IND specifications previously discussed with the FDA.

Each vial of patient-specific unconjugated idiotype will be labeled to include the following information:

Purified sterile immunoglobulin idiotype
patient-specific lot
final volume and concentration of product
patient-specific immunoglobulin subtype
storage conditions
fill date
patient identification (first name/last initial)

How Supplied—This product is available as a solution containing 0.2-0.3 ml of unconjugated idiotype diluted in sodium chloride 0.9%. The solution is contained inside a sterile vial. The final solution contains 0.5 mg of patient-specific immunoglobulin idiotype protein. Intact vials are stored at −20° C.

Toxicity—The toxicities associated with administration of unconjugated Id protein are anticipated to be identical to those described with the Id-KLH vaccine.

The safety issues regarding the injection of heterologous idiotype protein isolated from other patients' B-cell tumors have already been fully addressed in CRB #9407 (NCI T94-0085; Active immunization of Healthy Sibling Marrow Transplant Donors With Myeloma-derived Idiotype) and are felt to be minimal, because of the highly purified nature of the protein.

Briefly, an immune response of any consequence to the isotype matched idiotype used as a negative control during the second skin test is not likely, based on:

1. The isotype matched idiotype will only be administered once and is not conjugated to a carrier protein. These minimize the chance of eliciting a sustained immune response to the protein.
2. Any immune response specifically directed against the idiotype (i.e., variable region) on the control idiotype protein is not likely to cross-react with host cells and is therefore not likely to be of any consequence.
3. An autoimmune response against constant region or allotype determinants shared between the idiotype of the patient's own tumor and that of the control idiotype tumor is theoretically possible. However no evidence of such autoimmune responses have been observed either in vivo or in vitro during the course of immunization of sibling bone marrow transplant donors with purified myeloma protein.

Furthermore, a safety precedent exists for immunizing patients with material derived from tumor cells from other patients. For example, in attempting to develop immune responses against metastatic melanomas, patients were immunized with 1) intact melanoma cells; 2) shed antigens fractionated by detergent treatment and ultracentrifugation; 3) melanoma cells infected with vaccinia virus and melanoma cells freeze thawed and mechanically disrupted, all using a pool of allogeneic melanoma cell lines (24-28).

Bactrim will be supplied by the Clinical Center.

Filgrastim (G-CSF)/Neupogen

Source and Pharmacology—The G-CSF to be used in this study is the recombinant methionyl human granulocyte-colony stimulating factor (r-methi-HuG-CSF). G-CSF is a hematopoietic growth factor with effects on both immature bone marrow progenitors and mature myeloid cells. It acts by supporting growth of human bone marrow derived colony forming units and enhancing neutrophil growth and proliferation.

Formulation and Stability—The G-CSF is formulated as a clear, sterile solution and is provided in vials at a final concentration of 300 mcg/ml. The commercial vials are available in 300 and 480 mcg sizes. The intact vials are stored under refrigeration (2-8° C.) prior to use and must not be frozen and are stable at this temperature for at least one year.

Supplier—Manufactured by Amgen; supplied by the Clinical Center.

Route of Administration—The appropriate total dose is withdrawn into and administered from a plastic tuberculin syringe. The G-CSF is injected as a subcutaneous injection. The patient or other care-giver is instructed on proper injection technique.

Toxicities—Toxicities described with G-CSF include: transient bone pain (sternal/pelvic) myalgias, fatigue, mild elevations in uric acid, LDH and alkaline phosphate, fluid retention, transient hypotension, local inflammation at injection site, rarely cutaneous vasculitis, rarely pericardial effusion and rare anaphylactic reactions with first dose.

Statistical Considerations

Statistical issues to be addressed include identification of significant endpoints, sample size determination, power considerations, stratification, randomization and design.

The design of this study is viewed primarily within the framework of a Single Arm Phase II trial. However, as the purpose is also to investigate possible differences between GM-CSF doses as adjuvants, it incorporates design elements characteristic of a Multiple Arm Phase II or a randomized Phase III trial. Statistical methods that are appropriate to both single and double arm designs are described.

Patients receive combination chemotherapy to best response followed by Id-KLH combined with GM-CSF. Several outcome measures (endpoints) are evaluated in order to meet the objectives of this study. They include:

1) The clinical complete response rate (in contradistinction to the molecular or PCR response rate) of all patients to ProMACE—a percentage indicated by the disappearance of all clinical and laboratory signs and symptoms of active disease, excluding PCR, for a minimum of one month.

2) The Polymerase Chain Reaction (PCR) response rate (molecular-complete response rate)—the percentage of patients who, having achieved a clinical complete response still remain PCR (+) at the end of chemotherapy, and who then become PCR (−) with the administration of immunotherapy.

3) Disease Free Survival Rate—computed by Kaplan-Meier curves and related survival measures.

The PCR response rate is taken as the primary outcome variable of interest to ascertain the following: (1) to determine the ability of Id immunization to eradicate bcl-2 positive tumor cells from the bone marrow and; (2) to identify the more biologically active of the two doses of GM-CSF. In this endeavor, the plan is to accrue 42 patients. It is estimated that approximately 38 (90%) of these patients will be bcl-2 (+) and thus evaluable for molecular response rate. The other four patients may still be evaluable for a molecular response rate based on Ig gene amplification using allele-specific (CDR3) primers by PCR. From previous experience with ProMACE-based regimens, it is estimated that 32 (85%) of these patients will achieve either a complete response (complete clinical response, CCR) or a partial response in which a >90% partial remission has been obtained (high partial response, HPR). The accuracy of these estimates are of some interest. For the 42 (90%) patients anticipated to be bcl-2 (+), lower and upper 95% confidence intervals are 77% and 96%. For the 38 (85%) patients anticipated to achieve either a complete clinical response or a high partial response, the lower and upper confidence intervals are 70% and 93%.

Patients are stratified on the basis of their ProMACE treatment performance as either a complete clinical responder (CCR) or as a high partial responder (HPR). It is not known exactly what percentage of these 32 patients will be CCRs and what percentage will be HPR'S. Hence a block size of four (4) is used in the randomization scheme to assure a reasonably balanced allocation to each dose group. Given the patients allocation stratum, he (she) is randomly assigned to one of the adjuvant groups according to the envelope method (29). Specifically, a block of four assignments is placed in four separate envelopes. The block of four is placed in one of the two allocation strata, say CCR. Another block of four is placed in the other allocation strata, say CCR. Another block of four is placed in the other allocation stratum, HPR. When a patient is to be randomized, a call is made to the biostatistician who, after being informed of the patients status as either a CCR or an HPR, randomly draws an envelope from the appropriate stratum to determine the patients dose group assignment. After the four envelopes pertinent to a particular stratum have been exhausted, the next batch of four envelopes is made available for use. This procedure is continued until a total of 32 patients have been assigned to the two dose groups.

For example, it is estimated that 50-80 percent of pathological complete responders will fall into the CCR category. If 75% of 32, or 24 patients were to be classified as CCRs, six blocks of four envelopes would be required to randomly assign 12 patients to cohort 1 and 12 patients to cohort 2. A similar procedure would occur concurrently with the 8 patients classified as HPRs. Two blocks of four envelopes would be required to randomly assign 4 patients to cohort 1 and 4 patients to cohort 2. At no time could the number of patients in each dose group differ by more than four.

At the time of data analysis, approximately 16 subjects will comprise each dose group and a test for the difference in PCR response rates between the two groups will be conducted. By hypothesis, neither dose group is predicted to have a higher PCR response rate than the other; hence, a two-tailed test is appropriate. Power calculations show that, with the groups limited to 1 6 patients, the difference in PCR response rates will have to be large (30, 31). For example, to detect a difference at the $\alpha=0.05$ level of significance with power $(1-\beta)$ equal to 80%, the response rates must differ by 55%; with power equal to 50%, the response rates must differ by 50%. In the event that no significant difference is detected, the subjects will be pooled and the overall PCR response rate will be assessed. With a total of 32 CCRs and HPRs treated with vaccine, the width of a two-tailed 95% confidence interval for a response rate of 50% will not exceed 17 percentage points. If the actual response rate is higher or lower than 50%, the confidence interval will be smaller.

Disease-free survival distributions are estimated by the Kaplan-Meier (product-limit) method and dose groups are compared using the log rank test. If no dose group differences are detected, the subjects from both groups are pooled and the Kaplan-Meier estimate of the survivorship function and related functions are evaluated. If suggested by the data analysis, parametric distributions (e.g., Weibull, log-normal) are fit as well (32, 33).

Research ethics: Subjects from [both genders and] all racial/ethnic groups are eligible for this study if they meet the eligibility criteria outlined above. To date, there is not information that suggests that differences in grud metabolism or disease response would be expected in one group compared to another. Efforts are made to extend accrual to a representative population, but in this preliminary study, a balance must be struck between patient safety considerations and limitations on the number of individuals exposed to potentially toxic and/or ineffective treatments on the one hand and the need to explore gender and ethnic aspects of clinical research on the other hand. If differences in outcome that correlate to gender or to ethnic identity are noted, accrual can be expanded or a follow-up study can be written to investigate those differences more fully. Alternatively, substantial scientific data exist demonstrating that there is no significant difference in outcome between genders or various ethnic groups.

Records to be Kept and Quality Assurance

Consent form: The original signed informed consent documents will be kept with the patient's other study documentation (e.g., the research chart). A copy of the informed consent document will also be retained by the Data Management Section.

The Clinical Coordinator, Data Management Section, will ascertain the dates of the IRB approvals before registering the first patient.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

REFERENCES

1. Stevenson G T, Stevenson F K. Antibody to molecularly defined antigen confined to a tumor cell surface. *Nature*, 1975, 254:714-6.
2. Stevenson G T, Elliott E V, Stevenson F K. Idiotypic determinants on the surface Immunoglobulin of neoplastic lymphocytes: a therapeutic target. *Fed Proc*, 1977, 36:2268-71.
3. Miller P A, Maloney D G, Warnke R, Levy R. Treatment of B cell lymphoma with monoclonal anti-idiotypic antibody. *N Engl J Med*, 1982, 306; 517-22.
4. Sirisinha S, Eisen H N. Autoimmune-like antibodies to the ligand-binding sites of myeloma proteins. *Proc Natl Acad Sci USA*, 1971, 68:3130-5.
5. Jorgensen T, Gaudemack G, Hannestad K. Immunization with the light chain and the VL domain of the isologous myeloma protein 315 inhibits growth of mouse plasmacytoma MOPC-315. *Scand J Immunol*, 1980, 11:29-35.

6. Daley M J, Gebel H M, Lynch R G. Idiotype-specific transplantation resistance to MOPC-315: Abrogation by post-immunization thymectomy. *J Immunol,* 1978, 120: 1620-4.
7. Bridges S H. Participation of the humoral immune system in the myeloma-specific transplantation resistance. *J Immunol,* 1978, 121:479-83.
8. Freedman P M, Autry J R, Tokuda S, Williams R C, Jr. Tumor immunity induced by preimmunization with BALB/c mouse myeloma protein. *J Natl Cancer Inst.* 1976, 56:735-740.
9. Sugai S, Palmer D W, Taial N. Witz I P. Protective and cellular immune responses to idiotypic determinants on cells from a spontaneous lymphoma of NZB/NZWF1 mice. *J Exp Med,* 1974, 140:1547-58.
10. Stevenson F K, Gordon J. Immunization with idiotypic immunoglobulin protects against development of B lymphocytic leukemia, but emerging tumor cells can evade antibody attack by modulation. *J Immunol,* 1983, 130:970-973.
11. George A J T, Tutt A L, Stevenson F K. Anti-idiotypic mechanisms involved in the suppression of a mouse B cell lymphoma, BCL. *J Immunol,* 1987, 138:628-634.
12. Kaminski M S, Kitamura K, Maloney D G, Levy R. Idiotype vaccination against murine B cell lymphoma. Inhibition of tumor immunity by free idiotype protein. *J Immunol,* 1987, 138:1289-1296.
13. Kwak L W, Campbell M J, Zelonetz A D, Levy R. Combined syngeneic bone marrow transplantation and immunotherapy of a murine B-cell lymphoma: Active immunization with tumor-derived idiotypic immunoglobulin. *Blood,* 1990, 76:2411-2417.
14. Campbell M J, Esserman L. Byars N E, Allison A C, Levy R. Development of a new therapeutic approach to B cell malignancy: the induction of immunity by the host against cell surface receptor on the tumor. *Int Rev Immunol,* 1989, 4:251-70.
15. Kwak L W, Campbell M J, Czervwinski D K, Hart S, Miller R A, Levy R. Induction of immune responses in patients with B cell lymphoma against the surface immunoglobulin idiotype expressed by their tumors. *N Engl J Med,* 1992, 327:1209-1215.
16. Longo D L-Young R C, DeVita V T. What is so good about the "good prognosis" lymphoma? In Williams C G, Whithouse J M A (eds): *Recent Advances in Clinical Oncol* Edinburgh, Churchill-Livingstone, pp. 223-231, 1982.
17. Portlock C S. "Good risk" non-Hodgkin's lymphomas. Approaches to management. *Sem Hematol,* 1980. 20:25-34.
18. Portlock C S, Rosenberg S A. No initial therapy for stage III and IV non-Hodgkin's lymphomas of favorable histologic types. *Ann Intern Med,* 1979, 90:10-13.
19. Horning S J, Rosenberg S A. The natural history of initially untreated low-grade non-Hodgkin's lymphomas. *N Engl. J. Med,* 1984, 311:147-51.
20. Orentas R J. Hildreth J E K, Obah E, Polydefkis M. Smith G E, Clements M L, Siliciano R F. Induction of CD4+ human cytolytic T cells specific for HIV-infected cells by a gp 160 subunit vaccine. *Science,* 1990, 248:1234-6.
21. Schwartzentruber D J, Stetter-Stevenson M. Rosenberg S A, Topalian S L. Tumor infiltrating lymphocytes derived from select B-cell lymphomas secrete granulocyte-macrophage colony-stimulating factor and tumor necrosis factor-α in response to autologous tumor stimulation. *Blood,* 1993, 82:1204-11.
22. Schlegal P G. Schmidt-Wolf G, Schmidt-Wolf G H, Kwak L W, Blume K G, Chao N J. Lymphokine-activated killer cell activity against autologous lymphoma cells following bone marrow transplantation. *Cancer Res.* 1993.
23. Gribben J G, Freedman A S, Neuberg D, Roy D C, Blake K W, Woo S D, Grossard M L, Rabinow S N, Coral F, Freeman G J, Ritz J, Nadler L M. Immunologic purging of marrow assessed by PCR before autologous bone marrow transplantation for B-cell lymphoma. *N Engl J Med,* 1991, 325:1525.
24. Morton D L, et al. Annals New York Academy of Sciences. Polyvalent melanoma vaccine improves survival of patients with metastatic melanoma. 120; 1993.
25. Bystryn J C. Annals New York Academy of Sciences. Immunogenicity and clinical activity of a polyvalent melanoma antigen vaccine prepared from shed antigens. 190; 1993.
26. Wallack M K. Annals NewYork Academy of Sciences. Clinical trials with VMo for melanoma. 178; 1993.
27. Hershey P. Annals NewYork Academy of Sciences. Evaluation of vaccinia viral lysates as therapeutic vaccines in the treatment of melanoma. 167; 1993.
28. Mitchell M S et al. Annals New York Academy of Sciences. Active specific immunotherapy of melanoma with allogeneic cell lysates. 153; 1993.
29. Lesser M L. Design and implementation of clinical trials. In: Statistics in Medical Research—Methods and Issues with Applications in Cancer Research. Ed: Mike V and Stanley K F, New York, Wiley. 1982.
30. Gehan E A, Schneiderman M A: Experimental Design of Clinical Trials, in Holland J F and Frei E, Ill, eds. *Cancer Medicine* (2nd ed.). Lea and Febinger, Philadelphia, 531-553, 1982.
31. Gail M, Gart J J: The Determination of Sample Sizes for Use with the Exact Conditional Test in 2×2 Comparative Trials. *Biometrics,* 29, 441-448, 1973.
32. Lee E T: *Statistical Methods for Survival Data Analysis,* Wiley, New York, 1992.
33. Kalbfleisch J D, Prentice R L: *The Statistical Analysis of Failure Time Data,* New York, Wiley, 1980.
34. *Current protocols in immunology.* J. E. Coligan, A. D. Kruisbeek. D. H. Margulies, E. M. Sgevach and W. Strober, Eds. (J. Wiley & Sons, Inc., New York, 1994), p. 3-4.1.
35. B. A. Ben, et al, *J. Immunol.* 158, 5927 (1997).
36. Bergmann Y., J. Haimovich, Characterization of a carcinogen-induced murine B lymphocyte cell line of C3H/eb origin. *J. Immunol.* (1977). 7: 413
37. Kwak et al. 1991. Transfer of specific immunity to B-cell lymphoma with syngeneic bone marrow in mice. *Blood* 78:2768-2772.
38. E-Blasi, et al. *Nature* 318, 667 (1985).
39. R. Bonecchi, et al. *J. Exp. Med.* 187, 129 (1998).
40. J. Buchner, I. Pastan, U. Binkmann, *Anal. Biochem.* 205, 263 (1992).
41. E. C. Butcher, *Cell* 67, 1033 (1991).
42. M. J. Campbell, et al, *J. Immunol.* 139. 2825 (1987).
43. M. J. Campbell, L. Esserman. N. E. Byars, A. C. Alison, R. Levy, Idiotype vaccination against murine B cell lymphoma. Humoral and cellular requirements for the full expression of antitumor immunity. *J. Immunol.* (1998) 145 (3):1029-1036.
44. H. L. Davis et al. *Vaccine* 15, 849 (1997).
45. D. Dilloo et al. *Nature Medicine* 2, 1090 (1998).
46. R. J. Dyke, H. McBride, A. J. George, T. J. Hamblin, F. K. Stevenson, *Cell Immunol* 132, 70 (1991).
47. W. J. Fairbrother, N-J-Skelton, Chemoattractant ligands and their receptors., R. Horuk, Ed. (CRC, Boca Raton, N.Y., London, Tokyo, 1996), p. 55.
48. A. Haelens, et al. *Immunobiology* 195, 499 (1996).

49. I. Hakim, S. Levy, R. Levy, *J. Immunol* 157, 5503 (1996).
50. J. S. Huston, H. Oppermann, inventors, Targeted multifunctional proteins. USA. wo88 09344. (198).
51. K. J. Kim, L. C. Kanellopoulos, R. M. Merwin, D. H. Sachs, R. Asofsky, *J. Immunol.* 122, 549 (1979).
52. L. W. Kwak et al. *N. Engl. J. Med.* 327, 1209 (1992).
53. L. W. Kwak, et al. *Lancet* 345, 1016 (1995).
54. L. W. Kwak, H. A. Young, R. W. Pennington, S. D. Weeks, Proc. Natl. Acad. Sci. U.S.A. 93, 10972 (1996).
55. M. Loetscher et al., *J. Exp. Med.* 184, 963 (1995).
56. P. Loetscher, M. Seitz, L. I. Clark, M. Baggiolini, B. Moser, *J. Immunol.* 156, 322 (1996).
57. A. D. Luster, P. Leder, *J. Exp. Med.* 178, 1057 (1993).
58. A. D. Luster, *N. Eng. J. Med,* 338, 436 (1998).
59. B. J, Rollins, *Blood* 90, 909 (1997).
60. Y. Sato et al. *Science* 273, 352 (1996).
61. J. M. Schroder, *J. Invest. Dermatol.* 105, 20S (1995).
62. R. Solary et al, *J. Biol. Chem.* 272, 9617 (1997).
63. M. B. Spellerberg et al., *J. Immunol.* 159, 1885 (1997).
64. F. K. Stevenson et al., *Immunol. Rev.* 146. 211 (1996).
65. R. M. Strieter et al., *J. Biol. Chem.* 270, 27348 (1995).
66. C. J. Talpas, D. A. Walz, L. Lee, *Biochim. Biophys. Acta* 1078, 208 (1991).
67. Y. Tanaka, D. H. Adams, S. Shaw, *Immunol Today* 14, 111 (1993)
68. G. J. Weiner, H. M. Liu, J. E, Wooldridge, C. E. Dahle, A. M. Krieg, *Proc. Nat. Acad. Sci. U.S.A.* 94, 10833 (1997)
69. C. Winkler, et al, *Science* 279, 389 (1998).
70. M. Yokoyama, D. F. Hassett, J. Zhang, J. L. Whitton. *Vaccine* 15, 553 (1997).
71. Finn et al., 1995. *Immunological Reviews* 145:61-88; "Partially purified tumor antigen vaccines" In: *Biologic Therapy of Cancer: Principles and Practice,* 2nd ed. Edited by DeVita et al., J. B. Lippincott Co., 1995).
72. Old, L. J. "Cancer immunology: The search for specificity," GHA Clowes Memorial Lecture. *Cancer Res.* 41:361-375, 1981.
73. Livingston, P. In: *Biologic Therapy of Cancer: Principles and Practice,* 2nd ed. Edited by DeVita et al., J. B. Lippincott Co., 1995.
74. Harlow & Lane, *Antibodies, A Laboratory Manual*, Cold Spring Harbor Laboratory, Cold Spring Harbor, N.Y., 1988.
75. Baggioni, M., et al., 1994. IL-8 and related chemotactic cytokines-CXC and CC chemokines. *Adv. Immunol.* 55:97-179.
76. Garcia-Zepeda, E. A., et al., 1996. Human monocyte chemoattractant protein (MCP)-4 is a novel chemokine with activities on monocytes, eosinophils and basophils induced in allergic and nonallergic inflammation that signals through the CC chemokine receptors (CCR)-2 and -3. *J. Immunol.* 157:5613-5626.
77. Clark-Lewis et al., 1991. Structure-activity relationship of IL-8 determined using chemically synthesized analogs: critical role of $NH_2$-terminal residues and evidence for uncoupling neutrophil chemotaxis, exocytosis and receptor binding. *J. Biol. Chem.* 266:128-134.
78. Weber, M., et al., 1996. Deletion of the $NH_2$-terminal residue converts MCP-1 from an activator of basophil mediator release to an eosinophil chemoattractant. *J. Exp. Med.* 183:681-685.
79. *The Oncogene Handbook*, T. Curran, E. P. Reddy, and A. Salka (ed.), Elsevier Science Publishers, The Netherlands (1988).
80. Dayhoff et al., in *Atlas of Protein Sequence and Structure* 1978, Nat'l Biomed. Res. Found., Washington, D.C.
81. Sambrook et al., Molecular Cloning: A Laboratory Manual, 2d. edition, Cold Spring Harbor Laboratory, Cold Spring Harbor, N.Y., 1989.
82. Brake et al., "Alpha-factor-directed synthesis and secretion of mature foreign proteins in *Saccharomyces cerevisiae*," PNAS 82:4642-4646, 1984.
83. U.S. Pat. No. 4,704,362.
84. *Remington's Pharmaceutical Sciences* (Martin, E. W., ed., latest edition, Mack Publishing Co., Easton, Pa.).
85. Harlow and Lane, *Antibodies, A Laboratory Manual*, Cold Spring Harbor Laboratory, Cold Spring Harbor, N.Y., 1988).
86. "Immunologic Studies in Humans," *Current Protocols in Immunology*, J. E. Coligan et al., eds. John Wiley & Sons, New York, 1991.
87. Yamamoto et al., "Highly sensitive qualitative and quantitative detection of reverse transcriptase activity: optimization, validation and comparative analysis of other detection systems." *J. Virol. Meth.* 61:135-143, 1996.
88. Kageyama, S. et al., "An improved method for the detection of HIV antigen in the blood of carriers," *J. Virol. Meth.* 22:125-131, 1988.
89. Ho, D. D. et al., "Quantitation of human immunodeficiency virus type 1 in the blood of infected persons," *N. Eng. J. Med.* 321:1621-1625, 1988.
90. Piatak, M. et al., "High levels of HIV-1 in plasma during all stages of infection determined by competitive PCR," *Science* 259:1749-1754, 1993.
91. Mulder, T. et al., "Rapid and simple PCR assay for quantitation of human immunodeficiency virus type 1 RNA in plasma: Application to acute retroviral infection," *J. Clin. Microbiol.* 32:292-300, 1994.
92. Arnon, R. (Ed.) *Synthetic Vaccines* I:83-92, CRC Press, Inc., Boca Raton, Fla., 1987.
93. Willis et al., *Gene* 128:79-83, 1993.
94. Jellis et al., *Gene* 137:63-68, 1993.
95. Barbas et al., *PNAS* 89:4457-4461, 1992.
96. Pastan et al. "A retrovirus carrying an MDR1 cDNA confers multidrug resistance and polarized expression of P-glycoprotein in MDCK cells." *Proc. Nat. Acad. Sci.* 85:4486 (1988).
97. Miller et al. "Redesign of retrovirus packaging cell lines to avoid recombination leading to helper virus production." *Mol. Cell. Biol.* 6:2895 (1986).
98. Mitani et al. "Transduction of human bone marrow by adenoviral vector." *Human Gene Therapy* 5:941-948 (1994)).
99. Goodman et al. "Recombinant adeno-associated virus-mediated gene transfer into hematopoietic progenitor cells." *Blood* 84:1492-1500 (1994))
100. Naidini et al. "In vivo gene delivery and stable transduction of nondividing cells by a lentiviral vector." *Science* 272:263-267 (1996))
101. Agrawal et al. "Cell-cycle kinetics and VSV-G pseudotyped retrovirus mediated gene transfer in blood-derived $CD34^+$ cells." *Exp. Hematol.* 24:738-747 (1996)).
102. Schwarzenberger et al. "Targeted gene transfer to human hematopoietic progenitor cell lines through the c-kit receptor." *Blood* 87:472-478 (1996)).
103. Fields, et al. (1990) Virology, Raven Press, New York).
104. Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985-1001.

105. Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229-242.
106. Bergman, Y. & Haimovich, J. Characterization of a carcinogen-induced murine B lymphocyte cell line of C3H/eB origin. *Eur. J. Immunol.* 7, 413-417, 1977.
107. Kim, K. J., Kanelloupolos-Langevin, C. Merwin, R. M., Sachs, D. H. & Asofsky, R. Establishment and characterization of BALB/c lymphoma lines with B cell properties. *J. Immunol.* 122, 549-554, 1979.
108. Huston, J. S., Levinson, D., Mudgett-Hunter, M., Tai, M. S., Novotny, J., Margolies, M. N., Ridge, R. J., Bruccoleri, R. E., Haber, E., Crea R., & Opperman, H. Protein engineering of antibody binding sites: Recovery of specific activity in an anti-digoxin single-chain Fv analogue produced in *Escherichia coli*. *Proc. Natl. Acad. Sci. USA* 85, 5879-5883, 1988.
109. Blasi, E., Matthieson, B. J. & Varesio, L. Selective immortalization of murine macrophages from fresh bone marrow by a raf/myc recombinant murine retrovirus. *Nature* 318, 667-670, 1985.
110. Buchner, J., Pastan, I. & Brinkmann, U. A method for increasing the yield of properly folded recombinant fusion proteins: Single-chain immunotoxins from renaturation of bacterial inclusion bodies. *Analytical Biochem.* 205, 263-270, 1992.
111. Kwak, L. W., Young, H. A., Pennington, R. W., & Weeks, S. W. Vaccination with syngeneic, lymphoma-derived immunoglobulin idiotype combined with granulocyte/macrophage colony-stimulating factor primes mice for a protective T-cell response. *Proc. Natl. Acad. Sci. USA* 93, 10972-10977, 1996.
112. Falk, W., Goodwin, R. H., & Leonard, E. J. A 48-well micro chemotaxis assembly for rapid and accurate measurement of leukocyte migration. *J. Immunol. Methods* 33, 239-247, 1980.
113. Solari, R., Offord, R. E., Remy, S., Aubry, J. P., Wells, T. N. C., Whitehorn, E., Oung, T., & Proudfoot, A. E. I. Receptor-mediated endocytosis of CC-chemokines. *J. Biol. Chem.* 272, 9617-9620, 1997.
114. Feltquate, D. M., Heaney, S., Webster, R. G., & Robinson, H. L. Different T helper cell types and antibody isotypes generated by saline and gene gun DNA immunization. *J. Immunol.* 158, 2278-2284, 1997.
115. Kwak, L. W., Campbell, M. J., Czerwinski, D. K., Hart, S., Miller, R. A., & Levy, R. Induction of immune responses in patients with B-cell lymphoma against the surface-immunoglobulin idiotype expressed by their tumors. *N. Engl. J. Med.* 327, 1209-1215, 1992.
116. Kaminski, M. S., Kitamura, K., Maloney, D. G. & Levy, R. Idiotype vaccination against murine B cell lymphoma, inhibition of tumor immunity by free idiotype protein. *J. Immunol.* 138, 1289-1296, 1987.
117. Stevenson, G. T. & Stevenson, F. K. Antibody to a molecularly-defined antigen confined to a tumor cell surface. *Nature* 254, 714-716, 1975.
118. Xu, L. L., McVicar, D. W., Ben-Baruch, A., Kuhns, D. B., Johnston, J., Oppenheim, J. J. & Wang, J. M. Monocyte chemotactic protein-3 (MCP3) interacts with multiple leukocyte receptors: binding and signaling of MCP3 through shared as well as unique receptors on monocytes and neutrophils. *Eur. J. Immunol.* 25, 2612-2617, 1995.
119. Gong, J. H., Uguccioni, M., Dewald, B., Baggiolini, M. & Clark-Lewis, I. RANTES and MCP-3 antagonists bind multiple chemokine receptors. *J. Biol. Chem.* 271, 10521-10527, 1996.
120. Clore et al. 1990.
121. Lodi et al. 1994.
122. Skelton et al. 1995.
123. Fairbrother et al. 1994.
124. Horuk R, 1996.
125. Bergman and Haimovich, 1977. Characterization of a carcinogen-induced murine B lymphocyte cell line of C3H/eB origin. *Eur. J. Immunol.* 7:413-417.
126. Emini et al. 1992. Prevention of HIV-1 infection in chimpanzees by gp120 V3 domain-specific monoclonal antibody. *Nature*, 355:728-730.
127. Yarchoan et al. 1990. The National Cancer Institute Phase I Study of 2',3'-Dideoxyinosine Administration in Adults with AIDS or AIDS-related Complex: Analysis of Activity and Toxicity Profiles. *Reviews of Infectious Diseases*, 12(5):S522-S533.
128. Tani et al. 2000. Defensins act as potent adjuvants that promote cellular and humoral immune responses in mice to a lymphoma idiotype and carrier antigens. *International Immunology* 12(5): 691-700.
129. Yang et al. Oct. 15, 1999. β-Defensins: Linking innate and adaptive immunity through dendritic and T cell CCR6. *Science* 286: 525-528.
130. van Wetering et al. December 1999. Defensins: key players or bystanders in infection, injury, and repair in the lung? *J. Allergy Clin. Immunol.* 104(6): 1131-1138.

---

The invention claimed is:
1. A composition comprising:
   (1) a fusion polypeptide comprising a defensin and an antigen, wherein the antigen is either a viral antigen or a tumor antigen; and
   (2) an adjuvant.
2. The composition of claim 1, wherein the fusion protein comprises a viral antigen.
3. The composition of claim 1, wherein the viral antigen is a human immunodeficiency virus (HIV) antigen.
4. The composition of claim 3, wherein the human immunodeficiency virus antigen is gp160, gp120, gp41, or an immunogenic fragment thereof.
5. The composition of claim 4, wherein the human immunodeficiency viral antigen is gp120.
6. The composition of claim 3, wherein the viral antigen comprises the V3 loop of gp120.
7. The composition of claim 1, wherein the adjuvant comprises a cytokine.
8. The composition of claim 1, wherein the adjuvant comprises two or more cytokines.
9. The composition of claim 1, wherein the adjuvant comprises granulocyte macrophage colony stimulating factor (GM-CSF), interleukin-2, interleukin-12, interferon gamma, interleukin-4, tumor necrosis factor alpha, inerleukin-1, hematopoietic factor flt3L, CD40 ligand (CD40L).
10. The composition of claim 1, further comprising a liposome.
11. The composition of claim 1, wherein the defensin is an alpha defensin or a beta defensin.
12. The composition of claim 1, wherein the defensin is a beta defensin selected from the group consisting of human beta defensin 1 (HBD1) and human beta defensin 2 (HBD2), or wherein the defensin is an alpha defensin selected from the group consisting of HNP-1, HNP-2, and HNP-3.
13. The composition of claim 2, wherein the defensin is a beta defensin selected from the group consisting of HBD1 and HBD2, or an alpha defensin selected from the group consisting of HNP-1, HNP-2, and HNP-3.
14. The composition of claim 12, wherein the beta defensin is human beta defensin 2 (HBD2).
15. The composition of claim 1, wherein the antigen is a tumor antigen.
16. The composition of claim 15, wherein the tumor antigen is human epithelial cell mucin (Muc-1), p53, carcinoembryonic antigen (CEA), raf oncogene product GD2, GD3, GM2, MAGE-1, MAGE-3, tyrosinase, gp75, Melan-A/Mart-1, ap100, HER2/neu, Epstein Bar Virus LMP1 and 2, human papilloma virus F1, prostatic serum antigen (PSA), alpha-fetoprotein (AFP), CO17-1A, GA733, gp72, human papillomavirus E7, proteinase 3, Wilm's tumor antigen-1, telomerase, melanoma gangliosides, an antibody produced by a B cell tumor or a fragment thereof, an epitope of the idiotype of the antibody, a malignant B cell antigen receptor, a malignant B cell immunoglobulin idiotype, a variable region of an immunoglobulin, a complementarity determining region (CDR) of an immunoglobulin, a variable region of a T cell receptor or a hypervariable region of a T cell receptor.
17. An expression vector comprising a nucleic acid encoding a fusion polypeptide comprising (a) a defensin and a viral antigen or (b) a defensin and a tumor antigen, wherein the vector comprises a promoter operably linked to the nucleic acid encoding the fusion polypeptide.
18. The expression vector of claim 17, wherein the promoter is the lactose promoter, the tryptophan promoter, a beta-lactamase promoter, a phase lambda promoter or a cytomegalovirus promoter.
19. The expression vector of claim 17, wherein the vector is a cytomegalovirus vector or a plasmid vector.
20. A method of producing an immune response in a subject, comprising administering to the subject an effective amount of the composition of claim 1, thereby producing the immune response in the subject.
21. The method of claim 20, wherein the immune response is a T cell immune response.
22. The method of claim 20, wherein fusion polypeptide comprises a viral antigen, and wherein the viral antigen is a human immunodeficiency virus (HIV) antigen.
23. The method of claim 22, wherein the subject is infected with HIV.
24. The method of claim 22, wherein the human immunodeficiency virus antigen comprises the V3 loop of gp120.
25. The method of claim 20, wherein the fusion polypeptide comprises a tumor antigen.
26. The method of claim 20, wherein the defensin is a beta defensin selected from the group consisting of HBD1 and HBD2, or an alpha defensin selected from the group consisting of HNP-1, HNP-2, and HNP-3.
27. The method of claim 26, wherein the defensin is a beta defensin.
28. The method of claim 20, wherein the adjuvant comprises a cytokine.
29. The method of claim 28, wherein the cytokine is granulocyte macrophage colony stimulating factor.
30. The method of claim 20, wherein the antigen is a B cell lymphoma antigen, and wherein the cytokine is granulocyte macrophage colony stimulating factor.

* * * * *